US008034365B2

(12) United States Patent
Baluca

(10) Patent No.: US 8,034,365 B2
(45) Date of Patent: Oct. 11, 2011

(54) N-SUBSTITUTED MONOMERS AND POLYMERS

(75) Inventor: Ernest G Baluca, San Diego, CA (US)

(73) Assignee: Reva Medical, Inc., San Diego, CA (US)

( * ) Notice: Subject to any disclaimer, the term of this patent is extended or adjusted under 35 U.S.C. 154(b) by 1029 days.

(21) Appl. No.: 11/873,362

(22) Filed: Oct. 16, 2007

(65) Prior Publication Data

US 2008/0112999 A1    May 15, 2008

Related U.S. Application Data

(60) Provisional application No. 60/852,471, filed on Oct. 17, 2006.

(51) Int. Cl.
- *A61L 27/54* (2006.01)
- *A61L 27/58* (2006.01)
- *C08G 65/40* (2006.01)
- *A61F 2/82* (2006.01)

(52) U.S. Cl. ......... 424/426; 523/113; 424/423; 528/211

(58) Field of Classification Search .............. None
See application file for complete search history.

(56) References Cited

U.S. PATENT DOCUMENTS

| | | |
|---|---|---|
| 3,598,859 A | 8/1971 | Yates et al. |
| 4,638,045 A | 1/1987 | Kohn et al. |
| 4,733,665 A | 3/1988 | Palmaz |
| 4,740,207 A | 4/1988 | Kreamer |
| 4,748,982 A | 6/1988 | Horzenwski |
| 4,762,129 A | 8/1988 | Bonzel |
| 4,863,735 A | 9/1989 | Kohn et al. |
| 4,877,030 A | 10/1989 | Beck et al. |
| 4,954,126 A | 9/1990 | Wallstein |
| 4,980,449 A | 12/1990 | Kohn et al. |
| 5,007,926 A | 4/1991 | Berbushire |
| 5,040,548 A | 8/1991 | Yock |
| 5,059,211 A | 10/1991 | Stack et al. |
| 5,061,273 A | 10/1991 | Yock |
| 5,092,877 A | 3/1992 | Pinchuk |
| 5,099,060 A | 3/1992 | Kohn et al. |
| 5,108,416 A | 4/1992 | Ryan et al. |
| 5,140,094 A | 8/1992 | Kohn et al. |
| 5,151,100 A | 9/1992 | Abele et al. |
| 5,158,548 A | 10/1992 | Lau et al. |
| 5,192,307 A | 3/1993 | Wall |
| 5,194,570 A | 3/1993 | Kohn et al. |
| 5,197,987 A | 3/1993 | Kohn et al. |
| 5,198,507 A | 3/1993 | Kohn et al. |
| 5,230,349 A | 7/1993 | Lanberg |
| 5,232,445 A | 8/1993 | Bonzel |
| 5,242,399 A | 9/1993 | Lau et al. |
| 5,242,997 A | 9/1993 | Kohn et al. |
| 5,263,991 A | 11/1993 | Willey et al. |
| 5,264,537 A | 11/1993 | Kohn et al. |
| 5,300,085 A | 4/1994 | Yock |
| 5,306,286 A | 4/1994 | Stack et al. |
| 5,344,426 A | 9/1994 | Lau et al. |
| 5,350,395 A | 9/1994 | Yock |
| 5,423,321 A | 6/1995 | Fontenot |
| 5,441,515 A | 8/1995 | Khosravi et al. |
| 5,443,477 A | 8/1995 | Marin et al. |
| 5,443,500 A | 8/1995 | Sigwart |
| 5,445,646 A | 8/1995 | Euteneuer et al. |
| 5,449,382 A | 9/1995 | Dayton |
| 5,451,233 A | 9/1995 | Yock |
| 5,466,439 A | 11/1995 | Gibby et al. |
| 5,469,867 A | 11/1995 | Schmitt |
| 5,490,962 A | 2/1996 | Cima et al. |
| 5,496,275 A | 3/1996 | Sirhan et al. |
| 5,496,346 A | 3/1996 | Horzewski et al. |
| 5,527,337 A | 6/1996 | Stack et al. |
| 5,545,135 A | 8/1996 | Iacob et al. |
| 5,545,138 A | 8/1996 | Fugoso et al. |
| 5,549,556 A | 8/1996 | Ndondo-Lay et al. |
| 5,549,662 A | 8/1996 | Fordenbacher |
| 5,587,507 A | 12/1996 | Kohn et al. |
| 5,618,299 A | 4/1997 | Khosravi et al. |
| 5,626,600 A | 5/1997 | Hazewski et al. |
| 5,658,995 A | 8/1997 | Kohn et al. |
| 5,670,602 A | 9/1997 | Kohn et al. |
| 5,733,328 A | 3/1998 | Fprdembacher |
| 5,735,872 A | 4/1998 | Carpenter et al. |
| 5,741,293 A | 4/1998 | Wijay |
| 5,749,888 A | 5/1998 | Yock |

(Continued)

FOREIGN PATENT DOCUMENTS

| | | |
|---|---|---|
| WO | WO 90/14046 A1 | 11/1990 |
| WO | WO 98/46286 | 10/1998 |
| WO | WO 99/24391 | 5/1999 |
| WO | WO 2006/014596 | 2/2006 |
| WO | WO 2006/020616 | 2/2006 |

OTHER PUBLICATIONS

Benzina et al., "A versatile three-iodine molecular building block leading to new radiopaque polymeric biomaterials" Journal of Biomedical Materials Research, vol. 32, 459-466 (1996).

Aharoni, et al., "Rigid Backbone Polymers. 2. Polyisocyanates and Their Liquid-Crystal Behavior" *Macromolecules*, 12(1):94-103 (1979).

Andruzzi, et al., "Studies on Comb-like Polymers. 2. Poly(octadecylethylene oxide)" *Macromolecules*, 13:15-18(1980).

Aurelio, et al., "Synthetic Preparation of N-Methyl-α-amino Acids", *American Chemical Society*, Chem. Rev. 104, 5823-5846 (2004).

Cabasso, et al., "Radiopaque Miscible Systems Composed of Poly(Methyl Methacrylate) and Transition and Nontransition Metal Salts: Spectroscopic, Thermal, and Radiographic Characterization" *Journal of Applied Polymer Science*, 38:1653-1666 (1989).

(Continued)

*Primary Examiner* — Robert A Wax
*Assistant Examiner* — Danah Al-Awadi
(74) *Attorney, Agent, or Firm* — Knobbe Martens Olson & Bear LLP

(57) ABSTRACT

Described herein are N-substituted monomers and polymers, methods of making such monomers and polymers, and methods of using them in various applications, such as medical devices. In preferred embodiments, the medical device is a stent.

70 Claims, 1 Drawing Sheet

U.S. PATENT DOCUMENTS

| | | | |
|---|---|---|---|
| 5,755,708 | A | 5/1998 | Segal |
| 5,769,868 | A | 6/1998 | Yock |
| 5,800,393 | A | 9/1998 | Sahota |
| 5,836,965 | A | 11/1998 | Jendersee et al. |
| 5,868,747 | A | 2/1999 | Ochoa et al. |
| 5,876,419 | A | 3/1999 | Carpender et al. |
| 5,910,816 | A | 6/1999 | Fontenot et al. |
| 5,912,225 | A | 6/1999 | Mao et al. |
| 5,984,963 | A | 11/1999 | Ryan et al. |
| 5,989,280 | A | 11/1999 | Euteneuer et al. |
| 6,007,545 | A | 12/1999 | Venturelli |
| 6,015,424 | A | 1/2000 | Rosenbluth et al. |
| 6,033,436 | A | 3/2000 | Steinke et al. |
| 6,036,715 | A | 3/2000 | Yock |
| 6,048,521 | A | 4/2000 | Kohn et al. |
| 6,096,782 | A | 8/2000 | Audia et al. |
| 6,109,785 | A | 8/2000 | Ross et al. |
| 6,120,491 | A | 9/2000 | Kohn et al. |
| 6,200,338 | B1 | 3/2001 | Solomon et al. |
| RE37,160 | E | 5/2001 | Kohn et al. |
| 6,224,626 | B1 | 5/2001 | Steinke |
| 6,238,687 | B1 | 5/2001 | Mao et al. |
| 6,280,473 | B1 | 8/2001 | Lemperle et al. |
| 6,284,862 | B1 | 9/2001 | Kohn et al. |
| 6,319,492 | B1 | 11/2001 | Kohn et al. |
| 6,375,669 | B1 | 4/2002 | Rosenbluth et al. |
| 6,388,043 | B1 | 5/2002 | Langer et al. |
| 6,409,752 | B1 | 6/2002 | Boatman et al. |
| 6,409,755 | B1 * | 6/2002 | Vrba .......................... 623/1.2 |
| RE37,795 | E | 7/2002 | Kohn et al. |
| 6,447,508 | B1 | 9/2002 | Sharkey et al. |
| 6,475,477 | B1 | 11/2002 | Kohn et al. |
| 6,492,462 | B2 | 12/2002 | Bitler et al. |
| 6,530,958 | B1 | 3/2003 | Cima et al. |
| 6,544,453 | B2 | 4/2003 | Taft et al. |
| 6,550,480 | B2 | 4/2003 | Feldman et al. |
| 6,562,021 | B1 | 5/2003 | Derbin et al. |
| 6,562,958 | B1 | 5/2003 | Brenton et al. |
| 6,599,448 | B1 | 7/2003 | Ehrhard et al. |
| 6,602,497 | B1 | 8/2003 | Kohn et al. |
| 6,623,521 | B2 | 9/2003 | Steinke et al. |
| 6,652,572 | B2 | 11/2003 | Kugler et al. |
| 6,689,153 | B1 | 2/2004 | Skiba |
| 6,831,116 | B2 | 12/2004 | Bitler et al. |
| 6,852,308 | B2 | 2/2005 | Kohn et al. |
| 6,932,930 | B2 | 8/2005 | DeSimone et al. |
| 7,056,493 | B2 | 6/2006 | Kohn et al. |
| 2001/0046505 | A1 | 11/2001 | Kohn et al. |
| 2003/0163187 | A1 * | 8/2003 | Weber ..................... 623/1.2 |
| 2004/0086458 | A1 | 5/2004 | Kohn et al. |
| 2004/0086461 | A1 | 5/2004 | Kohn et al. |
| 2004/0086462 | A1 | 5/2004 | Kohn et al. |
| 2004/0127970 | A1 | 7/2004 | Saunders et al. |
| 2004/0191175 | A1 | 9/2004 | Kohn et al. |
| 2005/0106119 | A1 | 5/2005 | Brandom |
| 2005/0123481 | A1 | 6/2005 | Kohn et al. |
| 2005/0165203 | A1 | 7/2005 | Kohn et al. |
| 2006/0020324 | A1 | 1/2006 | Schmid |
| 2006/0024266 | A1 * | 2/2006 | Brandom et al. ......... 424/78.17 |
| 2006/0034769 | A1 | 2/2006 | Kohn et al. |
| 2006/0036316 | A1 | 2/2006 | Zeltinger et al. |
| 2006/0204440 | A1 | 9/2006 | Kohn et al. |

OTHER PUBLICATIONS

Cabasso, et al., "Radiopaque Polymers Based on Acrylated Phosphonate Esters Derived from Polyols" *Journal of Applied Polymer Science*, 41:3025-3042(1990).

Chupov, et al., "Structure and Physico-Chemical Properties of Comb-Like Polypeptides Based on Poly-L-Lysine" *Polymer Science U.S.S.R.* 21:241-252 (1979).

Fukuyama, et al., "2- and 4-Nitrobenzenesulfonamides: Exceptionally Versatile Means for Preparation of Secondary Amines and Protection of Amines" *Terahedron Letters, Elsevier Science Ltd.*, vol. 36, No. 36, pp. 6373-6374 (1995).

Fukuyama, et al., "2,4-Dinitrobenzenesulfonamides: A Simple and Practical Method for the Preparation of a Variety of Secondary Amines and Diamines", *Tetrahedron Letters, Elsevier Science Ltd.*, vol. 38, No. 33. pp. 5831-5834 (1997).

Gonzalez, et al. Side-Chain Crystallinity, Heat of Melting, and Thermal Transitions in poly[N(10-n-Alkyloxycarbonyl-n-Decyl)Maleimides] (PEMI) *Journal of Polymer Science: Polymer Physics Edition*, 18:2197-2207 (1980).

Greenberg, et al., "Side Chain Crystallization of n-Alkyl Polymethacrylates and Polyacrylates" *Institute of Polymer Research, Polytechnic Institute of Brooklyn.* 76:6280-6285. (1954).

Hooper, et al., "Diphenolic monomers derived form the natural amino acid alpha-l-tyrosine: an evaluation of peptide coupling techniques" *Journal of Bioactive and Compatible Polymers*, 10(4):327-340 XP002045571.

Hutmacher et al., "Scaffold-based tissue engineering: rationale for computer-aided design and solid free-form fabrication systems," *TRENDS in Biotechnology* vol. 22 No. 7, Jul. 2004, pp. 354-362.

Jayakrishnan, et al., "Synthesis and Polymerization of Some Iodine-Containing Monomers for Biomedical Applications" *Journal of Applied Polymer Science* 44:743-748 (1992).

Jordan, et al., "Side-Chain Crystallinity. I. Heats of Fusion and Melting Transitions on Selected Homopolymers Having Long Side Chains" *Journal of Polymer Science: Part A-1*, 9:1835-1852 (1971).

Jordan, et al., "Side-Chain Crystallinity. II. Heats of Fusion and Melting Transitions on Selected Copolymers Incorporating n-Octadecyl Acrylate or Vinyl Stearate" *Journal of Polymer Science:Part A-1*, 9:3349-3365 (1971).

Jordan, et al., "Side-Chain Crystallinity. III. Influence of Side-Chain Crystallinity on the Glass Transition Temperatures of Selected Copolymers Incorporating n-Octadeeyl Acrylate or Vinyl Stearate" *Journal of Polymer Science: Part A-1* 9:3367-3378(1971).

Jordan, et al., "Side-Chain Crystallinity. V. Heats of Fusion and Melting Temperatures on Monomers Whose Homopolymers Have Long Side Chains" *Journal of Polymer Science*, 10:3347-3366 (1972).

Kan, et al., "Efficient Synthesis of Medium-Sized Cyclic Amines by Means of 2-Nitrobenzenesulfonamide", *Synlett, Georg Thieme Verlag Stuttgart*, No. 5, 697-699 (2002).

Kocienski, "A highly efficient method of N-methylation for the amino acid derivatives", *Indian Journal of Chemistry*, vol. 34B, Jan. 1995, pp. 45-47.

Kruft, et al., "In vivo tissue compatibility of two radio-opaque polymeric biomaterials" *Biomaterials*, 18:31-35(1997).

Kruft, et al., "Studies on radio-opaque polymeric biomaterials with potential applications to endovascular prostheses" *Biomaterials*, 17:1803-1812 (1996).

Ma, et al., "Cul-Catalyzed Coupling Reaction of β-Amino Acids or Esters with Aryl Halides at Temperature Lower than That Employed in the Normal Ullmann Reaction. Facile Synthesis of SB-214857", *Organic Letters, American Chemical Society*, vol. 3, No. 16, 2583-2586 (2001).

Magagnini, et al., "Studies on Comb-like Polymers. 1. Poly(octadecylethylene)" *Macromolecules*, 13:12-15(1980).

Mao, et al. "Synthesis and Biological Properties of Polymer Immunoadjuvants" *Polymer Journal*, 25(5):499-505 (1993).

O'Driscoll, et al., "Kinetics of Anionic Copolymerization of Monomers of Similar Polarities" *Journal of Polymer Science*, 61:19-24 (1962).

Overberger, et al., "The Preparation and Polymerization of p-Alkylstyrenes. Effect of Structure on the TransitionTemperatures of the Polymers" *The Department of Chemistry, Institute of Polymer Research, Polytechnic Institute of Brooklyn*. 75:3326-3330.

Penso, et al., "Chemoselective N-Alkylation of Di-N, O-protected Tyrosine through Specific Oxy-Anion Solvation by Non-Hydrogen Bonding Donor Solvents", *Synlett, Georg Thieme Verlag Stuttgart*,No. 5, pp. 0741-0744 (2006).

Perez, "An Easy Method for the N-Alkylation of Amides, Carbamates, Ureas and Azoles. Reactivity of 4-Chloromethylpyrazoles with Weak Nucleophiles under Neutral Conditions", Paloma B., *Heterocycles* 60 (2003) 1, 167-175; Dep. Quim. Org. Biol., Fac. Cienc., UNED, Ciudad Univ., E-28040 Madrid, Spain: Eng.

Pittman, et al., "Effect of Polymer Crystallinity on the Wetting Properties of Certain Fluroalkyl Acrylates" *Journal of Polymer Science Part A-1*, 7:3053-3066 (1969).

Plate, et al., "Comb-Like Polymers. Structure and Properties" *J. Polymer Sci.:Macromolecular Reviews*, 8:117-253(1974).

Prashad, et al., "An Efficient and Practical N-Methylation of Amino Acid Derivatives", *Organic Letters, American Chemical Society*, vol. 5, No. 2, 125-128 (2003).

Pulapura, et al. "Structure-Property Relationships for the Design of Polyiminocarbonates" *Biomaterials* 11(9):666-678. XP000172545.

Rabolt, et al., "Studies of Chain Conformational Kinetics in Poly(di-*n*-alkylsilanes) by Spectroscopic Methods. 1.Poly(di-*n*-hexylsilane), Poly(di-*n*-heptylsaline), and Poly(di-*n*-octylsilane)." *Macromolecules*, 19:611-616 (1986).

Wada, et al., "Effect of Amount of Medium on the Radiation-Induced Polymerization of Ethylene in *tert*-Butyl Alcohol" *Journal of Polymer Science: Part A-1*, 10:1655-1667 (1972).

Watanabe, et al., "Thermotropic Polypeptides. 2. Molecular Packing and Thermotropic Behavior of Poly (L-glutamates) with Long *n*-Alkyl Side Chains", *Macromolecules* 18:2141-2148 (1985).

The International Search Report and the Written Opinion of the International Searching Authority in the PCT/US2007/081566. Mailing date: Aug. 28, 2008.

\* cited by examiner

N-SUBSTITUTED MONOMERS AND POLYMERS

CROSS-REFERENCE TO RELATED APPLICATIONS

This application claims priority to U.S. Provisional Application No. 60/852,471, filed on Oct. 17, 2006 and entitled "N-Substituted Monomers and Polymers," the contents of which are hereby incorporated by reference in their entirety.

BACKGROUND OF THE INVENTION

1. Field of the Invention

This invention relates to N-substituted monomers and polymers, methods of making such monomers and polymers, and methods of using them in various applications, such as medical devices.

2. Description of the Related Art

Vascular stents are used widely in a variety of applications, including, especially, in the treatment of heart disease. It has been reported that in 1998, about 61 million Americans had some form of heart disease, which since about 1990 has been the single leading cause of death in the United States.

One type of heart disease, coronary artery disease (CAD), is characterized, at least in part, by the inhibition of blood flow through the arteries that supply blood to the heart muscle due to the buildup of plaque (arteriosclerosis) in the arteries. CAD is suspected to account for 1 out of every 5 deaths that occur in the U.S.A. In 2001, about 1.1 million people had a new or recurrent myocardial infarction (heart attack due to coronary arterial disease). See, for example, Report by the American Heart Association, "Heart and Stroke Statistical Update," 2001, American Heart Association, Dallas, Tex. Currently more than 500,000 Americans are treated annually for blocked coronary arteries. This number is expected to double over the next 10 years in light of the aging population.

Vascular stents generally comprise a mesh tube, which is inserted into an artery to keep the artery open after it has been stretched with a balloon during the course of an angioplasty procedure. Typically, the vascular stent is mounted on a balloon catheter that is inserted via the femoral artery and pushed to the desired location in the coronary artery. There, the balloon is inflated, thus expanding the stent and pressing it against the vessel wall to lock it in place.

Most stents are constructed from metal, including, for example, stainless steel or nitinol. While such metal stents possess certain desirable characteristics, such as sufficient radial strength to hold open a subject artery and radio-opacity (allowing an implanted stent to be seen and monitored by X-ray radiography/fluoroscopy), metal stents also exhibit a number of significant disadvantages. For example, the insertion and expansion of a metal stent in an artery tends to further injure the diseased vessel, potentially leading to the development of intimal hyperplasia and further occlusion of the vessel by the resulting in-growth of smooth muscle cells and matrix proteins through the stent struts.

Another disadvantage associated with use of metal stents is that once deployed, they become permanent residents within the vessel walls—long after their usefulness has passed. Indeed, the useful lifespan of a stent is estimated to be in the range of about 6 to 9 months. After this time, the chronic stresses and strains imposed on the vessel architecture by the permanent metal implants are believed to promote in-stent restenosis.

Another disadvantage associated with the use of metal stents is that the placement of multiple permanent metal stents within a vessel may be a barrier to subsequent surgical bypass. Further, the deployment of a first metal stent may become a physical hurdle to the later delivery of a second stent at a distal site within the same vessel. In contrast to a metal stent, a bioresorbable stent may not outlive its usefulness within the vessel. Moreover, a bioresorbable stent may be used to deliver a greater dose of a therapeutic, as a drug and/or biological agent could be coated on the stent as well as embedded in the device itself. Further, such a stent could deliver multiple drugs and/or biological agents, at the same time or at various times of its life cycle, to treat specific aspects or events of vascular disease. Additionally, a bioresorbable stent may also allow for repeat treatment of the same approximate region of the blood vessel.

U.S. Pat. No. 6,475,477 ("the '477 patent") discloses medical devices formed from radiopaque biocompatible polymers with hydrolytically unstable polymer backbones and pendant free carboxylic acid groups that promote polymer degradation and resorption; incorporated herein in its entirety by reference. Not only are many of the disclosed polymers less than ideal for use in stents, various polymers with free carboxylic acid groups are prepared from monomers with benzyl-protected free acid moieties that are selectively removed from the polymer via hydrogenolysis in the presence of a palladium catalyst and hydrogen. While such a method is effective for removing the benzyl protecting groups with little or no cleaving of the polymer backbone, the palladium catalyst used therein is relatively expensive, and traces of palladium are difficult to remove from the polymer product.

Some of the aforementioned deficiencies of the '477 patent have been addressed in U.S. Patent Application Publication No. 2005/0106119, entitled "Inherently Radiopaque Polymeric Products for Embolotherapy," the contents of which are hereby incorporated by reference in their entirety. A wide variety of other amide-containing monomers and polymers are known, see, e.g., U.S. Pat. Nos. 5,099,060; 5,198,507; 5,587,507; RE 37,160; 5,670,602; RE 37,795; 5,658,995; 6,048,521; 6,319,492; 6,120,491; 6,475,477; 6,602,497; 6,852,308; 7,056,493; 6,284,862; 4,980,449; 5,140,094; 5,264,537; 5,194,570; and 5,242,997; U.S. Patent Publication Nos. 2006-0204440; 2006-0034769; 2005-0106119; 2005-0123481; 2005-0165203; 2004-0191175; 2004-0086462; and 2004-0086458; and U.S. patent application Ser. No. 09/350,423, all of which are hereby incorporated by reference in their entireties.

However, there remains a need for additional polymeric formulations that provide advantageous physicochemical properties adapted for use in fabricating a variety of implantable medical devices.

SUMMARY OF THE INVENTION

An embodiment provides N-substituted monomers and polymers that comprise an N-substituted amide group, and methods for making such monomers and polymers. In an embodiment, the N-substitution is an N-alkylation. In an embodiment, the N-substitution is an N-methylation.

A variety of amide-containing monomers and polymers are useful in the applications and procedures described herein. For example, U.S. Patent Application Publication Nos. 2006/0024266 and 2006/0182779, both entitled "Side-Chain Crystallizable Polymers for Medical Applications"; U.S. Patent Application Publication No. 2006/0036316 entitled "Inherently Radiopaque Bioresorbable Polymers for Multiple Uses"; and U.S. Patent Application Publication No. 2006/0115449 entitled "Bioabsorbable, Biobeneficial, Tyrosine- Based Polymers for Use in Drug Eluting Stent Coatings" all disclose various amide-containing monomers and polymers.

All of the foregoing patent application publications are hereby incorporated by reference in their entireties, and, as applicable, particularly for the purposes of (1) describing monomers and polymers to which the N-substitution as described herein applies, (2) describing methods of making monomers and polymers that can be modified by the N-substitution described herein, and (3) describing methods of using monomers and polymers which are also applicable to the N-substituted monomers and polymers described herein, including but not limited to the use of such N-substituted monomers and polymers for a variety of medical uses and applications, such as for making medical devices (e.g., stents, embolotherapy products) and components thereof (e.g., coatings).

An embodiment provides a polymer that comprises a recurring unit of the formula (I) as set forth below. Another embodiment provides a medical device that comprises a polymer comprising a recurring unit of the formula (I). In an embodiment, the medical device comprises at least a stent. Another embodiment provides a method of treatment that includes introducing a medical device into a body cavity of a mammal in an amount that is effective to at least partially occlude the body cavity, wherein the medical device comprises a polymeric material, and wherein the polymeric material comprises a recurring unit of the formula (I). In an embodiment, the method further includes forming a channel through the medical device.

An embodiment provides a polymer that comprises a recurring unit of the formula (Ia) as set forth below. Another embodiment provides a medical device that comprises a polymer comprising a recurring unit of the formula (Ia). In an embodiment, the medical device comprises at least a stent. Another embodiment provides a method of treatment that includes introducing a medical device into a body cavity of a mammal in an amount that is effective to at least partially occlude the body cavity, wherein the medical device comprises a polymeric material, and wherein the polymeric material comprises a recurring unit of the formula (Ia). In an embodiment, the method further includes forming a channel through the medical device.

An embodiment provides a polymer that comprises a recurring unit of the formula (XI) as set forth below. Another embodiment provides a medical device that comprises a polymer comprising a recurring unit of the formula (XI). In an embodiment, the medical device comprises at least a stent. Another embodiment provides a method of treatment that includes introducing a medical device into a body cavity of a mammal in an amount that is effective to at least partially occlude the body cavity, wherein the medical device comprises a polymeric material, and wherein the polymeric material comprises a recurring unit of the formula (XI). In an embodiment, the method further includes forming a channel through the medical device.

An embodiment provides a method for making a polymer comprising a recurring unit of formula (I), the method comprising attaching an N-substituent during the synthesis of a corresponding monomer. An embodiment provides a method for making a polymer comprising a recurring unit of formula (I), the method comprising attaching an N-substituent during polymerization of a corresponding monomer. An embodiment provides a method for making a polymer comprising a recurring unit of formula (I), the method comprising attaching an N-substituent after polymerization of a corresponding monomer.

An embodiment provides a method for making a polymer comprising a recurring unit of formula (Ia), the method comprising attaching an N-substituent during the synthesis of a corresponding monomer. An embodiment provides a method for making a polymer comprising a recurring unit of formula (Ia), the method comprising attaching an N-substituent during polymerization of a corresponding monomer. An embodiment provides a method for making a polymer comprising a recurring unit of formula (Ia), the method comprising attaching an N-substituent after polymerization of a corresponding monomer.

An embodiment provides a method for making a polymer comprising a recurring unit of formula (XI), the method comprising attaching an N-substituent during the synthesis of a corresponding monomer. An embodiment provides a method for making a polymer comprising a recurring unit of formula (XI), the method comprising attaching an N-substituent during polymerization of a corresponding monomer. An embodiment provides a method for making a polymer comprising a recurring unit of formula (XI), the method comprising attaching an N-substituent after polymerization of a corresponding monomer.

These and other embodiments are described in greater detail below.

DETAILED DESCRIPTION OF THE PREFERRED EMBODIMENTS

Figure 1:
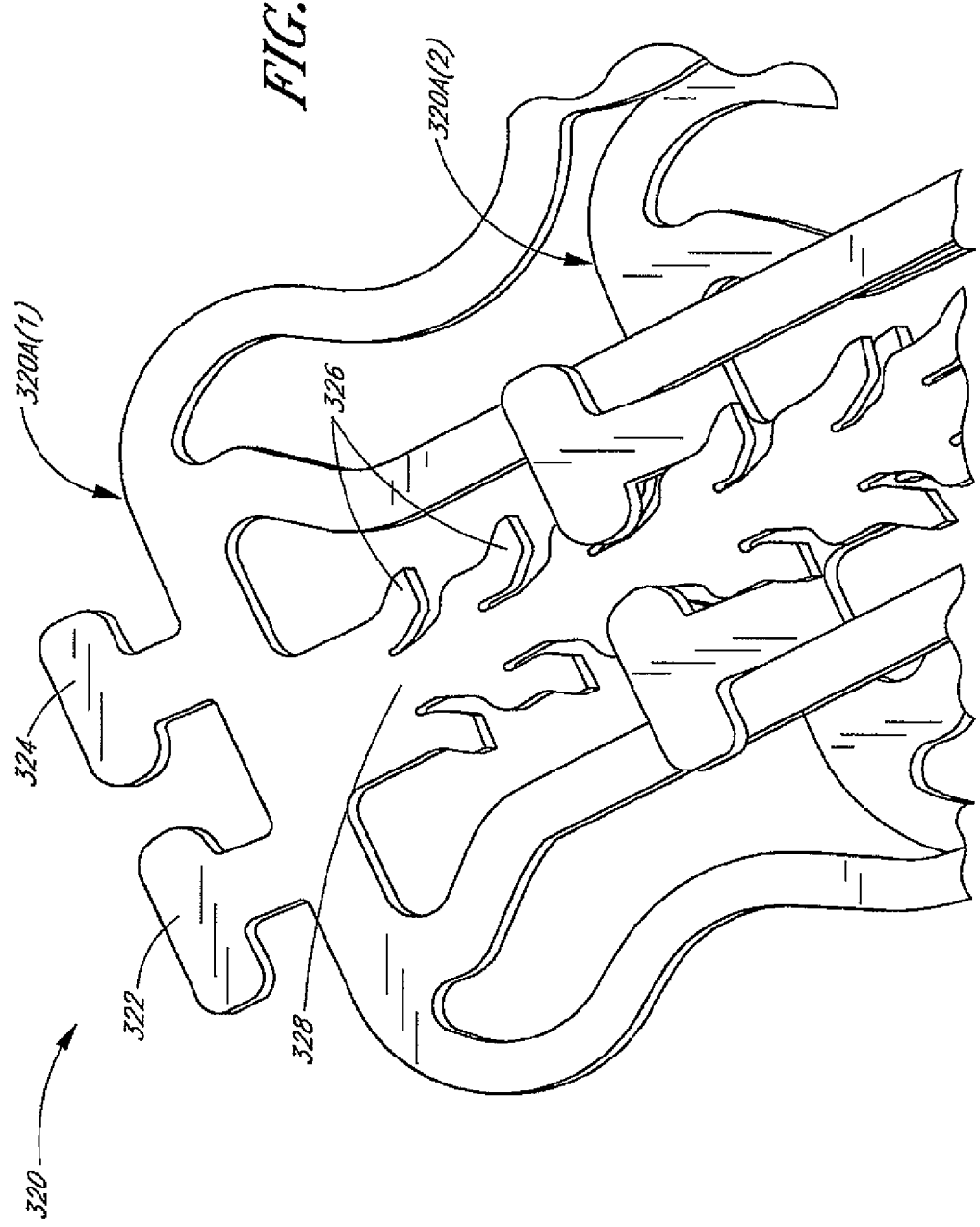
FIG. 1 is a detailed view of a slide-and-lock stent configuration in accordance with one preferred embodiment of the present invention, comprising deflectable teeth which deflect downward to provide a stent exhibiting mono-directional expansion.

The term "halogen atom," as used herein, means any one of the radio-stable atoms of column 7 of the Periodic Table of the Elements, e.g., fluorine, chlorine, bromine, or iodine, with bromine and iodine being preferred.

The term "ester" refers to a chemical moiety with formula —$(R)_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1. An "ester linkage" is an ester group that links two chemical moieties to one another.

An "amide" is a chemical moiety with formula —$(R)_n$—C(O)NHR' or —$(R)_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug. An "amide linkage" is an amide group (—C(O)NH—) that links two chemical moieties to one another.

Any amine, hydroxy, or carboxyl side chain on the compounds disclosed herein can be esterified or amidified. The procedures and specific groups to be used to achieve this end are known to those of skill in the art and can readily be found in reference sources such as Greene and Wuts, Protective Groups in Organic Synthesis, $3^{rd}$ Ed., John Wiley & Sons, New York, N.Y., 1999, which is incorporated by reference herein in its entirety.

As used herein, "alkyl" refers to a straight or branched hydrocarbon chain fully saturated (no double or triple bonds)

hydrocarbon group. The alkyl group may have any number of carbons associated therewith, up to and including 50 carbon atoms. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group of the compounds may be designated as "$C_1$-$C_{30}$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, octyl, decyl, octadecyl, ethenyl, propenyl, butenyl, and the like.

The alkyl group may be substituted or unsubstituted. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Wherever a substituent is described as being "optionally substituted" that substitutent may be substituted with one of the above substituents.

As used herein, "heteroalkyl" refers to an alkyl group where one or more carbon atoms has been replaced with a heteroatom, that is, an element other than carbon, including but not limited to, nitrogen, oxygen and sulfur.

As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene. An aryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroaryl" refers to an aryl group where one or more carbon atoms has been replaced with a heteroatom, that is, an element other than carbon, including but not limited to, nitrogen, oxygen and sulfur.

An "alkylaryl" is an aryl group connected, as a substituent, via an alkylene group. The alkylene and aryl group of an aralkyl may be substituted or unsubstituted. Examples include but are not limited to benzyl, substituted benzyl, 2-phenylethyl, 3-phenylpropyl, and naphtylalkyl. In some cases, the alkylene group is a lower alkylene group. An alkylaryl group may be substituted or unstubstituted.

"Alkylene" groups are biradical tethering groups, forming bonds to connect molecular fragments via their terminal carbon atoms. Examples include but are not limited to methylene ($-CH_2-$), ethylene ($-CH_2CH_2-$), propylene ($-CH_2CH_2CH_2-$), and butylene ($-(CH_2)_4-$) groups. An alkylene group may be substituted or unsubstituted.

Unless otherwise indicated, when a substituent is deemed to be "optionally substituted," it is meant that the substitutent is a group that may be substituted with one or more group(s) individually and independently selected from alkyl, alkenyl, alkynyl, cycloalkyl, aryl, heteroaryl, heteroalicyclic, hydroxyl, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

A "heavy atom" is an atom that, when attached to a polymer, renders the polymer easier to detect by an imaging technique as compared to a polymer that does not contain the heavy atom. Since many polymers contain relatively low atomic number atoms such as hydrogen, carbon, nitrogen, oxygen, silicon and sulfur, in most cases heavy atoms have an atomic number of 17 or greater. Preferred heavy atoms have an atomic number of 35 or greater, and include bromine, iodine, bismuth, gold, platinum tantalum, tungsten, and barium.

A "hydrocarbon" is an organic compound consisting entirely of hydrogen and carbon. Examples of hydrocarbons include unsubstituted alkyl groups, unsubstituted aryl groups, and unsubstituted alkylaryl groups. Any substitution to an alkyl group, aryl group, or alkylaryl group in a hydrocarbon would only comprise carbon and/or hydrogen atoms.

The terms "purified," "substantially purified," and "isolated" as used herein refer to compounds disclosed herein being substantially free of other, dissimilar compounds with which the compounds of the invention are normally associated in their natural state, so that the compounds of the invention comprise at least 0.5%, 1%, 5%, 10%, or 20%, and most preferably at least 50% or 75% of the mass, by weight, of a given sample.

A "non-fouling moiety" is a portion of a chemical compound that is capable of providing the compound the ability to prevent, or at least reduce, the build-up of a denatured layer of protein on the stent surface or on the stent coating. It is a type of bioactive and a type biobeneficial moiety.

Provided herein are N-substituted monomers and polymers, particularly N-substituted monomers and polymers comprising an amide group. In an embodiment, the N-substitution on the amide-containing polymer is on the nitrogen atom of the amide bond.

Depending on molecular weight and temperature, the polymers described in U.S. Patent Application Publication Nos. 2006/0024266, 2006/0182779, 2006/0036316, and 2006/0115449, incorporated by reference above, may have relatively high viscosities in the melted state, leading to difficulties in processing. Without wishing to be bound by theory of operation, it is believed that one reason for the relatively high viscosity of these polymers in the melt state may be intermolecular hydrogen bonding between the hydrogen atom bonded to the nitrogen atom of the amide bond and other H-bonding groups within the polymer.

It has been discovered that the substitution of that hydrogen, by a methyl or alkyl group, or even an aryl group, can effectively diminish intermolecular hydrogen bonding to a surprising degree, resulting in advantageous processing properties and additionally, subsequently superior mechanical properties. For example, a typical amide-coupled amino acid-based degradable polymer composition, wherein the chain stiffness and molecular architecture are optimized for high mechanical strength and modulus, may reach process decomposition limits in melt processing either through shear and/or temperature. By diminishing the hydrogen bonding effect through N-substitution, the melt viscosity can be reduced thereby allowing for easier melt processing (lower temperature and/or shear). This allows one to take full advantage of the molecular spectrum of possibilities with less process-constrained limitations.

Similarly, the effect of hydrogen bonding mitigation in solution-based systems is also of value. By limiting hydrogen-bonding effects of the polymers described herein, one can achieve a higher solids concentration in solution without reaching relatively high solution viscosities. This allows one to process these polymers within a wider processing window from a concentration standpoint. It is believed that higher quality solution cast parts can be obtained since higher solids content castings tend to mitigate surface inconsistencies commonly found in dilute solution castings. These features can be achieved according to the methods described herein without use of hydrogen bond masking agents, e.g., trifluoroacetic acid in a polymer-dichloromethane solution, which have the burdensome and often unachievable step of removal of the residual masking agent.

It has been discovered that providing a non-hydrogen-bonding substituent, such as an optionally substituted branched or unbranched C1-C30 alkyl group or an optionally substituted C6-C30 aryl, in the Rx position of a polymer comprising a recurring unit of the formula (I), formula (Ia), and/or formula (XI), as set forth below, eliminates or greatly reduces sources of intermolecular interaction to a surprising degree. As a result, the melt viscosity of these polymers is reduced.

Consequently, an N-substituted version of the polymer may be processed at lower temperatures (e.g., relative to the polymer glass transition temperature or Tg) with less thermal/oxidative degradation. This opens the temperature processing window for the polymer, e.g., higher Tg polymers can be processed at existing process temperatures and similar Tg polymers may be processed at lower temperatures.

Additionally, N-substituted versions of polymers of the general type described in the patent application publications incorporated by reference above will also tend to have higher free volumes as a consequence, depending on the size of the N-substituent. Such control over the free volume may be used to advantage because free volume greatly affects the elution rates of small molecule compounds (such as therapeutic agents) from the polymer. The N-substituted polymers described herein are useful for making a variety of devices, including without limitation medical devices. In some embodiments, N-substituted versions of monomers and polymers of the general type described in the patents and patent applications incorporated by reference above are bioresorbable. The term "bioresorbable" is used herein to designate polymer that undergoes biodegradation (through the action of water and/or enzymes to be chemically degraded) and at least some the degradation products are eliminated and/or absorbed by the body.

N-substitution of the polymers described herein is not limited to the nitrogen atom of the amide group. Furthermore, providing a non-hydrogen-bonding substituent, such as an optionally substituted branched or unbranched C1-C30 alkyl group or an optionally substituted C6-C30 aryl, in other positions besides the Rx position of a polymer comprising a recurring unit of the formula (I), formula (Ia), and/or formula (XI) is also envisioned. For example, it is also contemplated to provide a non-hydrogen-bonding substituent, such as an optionally substituted branched or unbranched C1-C30 alkyl group or an optionally substituted C6-C30 aryl, in the Ry position of a polymer comprising a recurring unit of the formula (I) and/or formula (XI).

The polymers described herein may also be rendered radiopaque by the inclusion of heavy atoms, such as bromine or iodine. The term "radiopaque" is used herein to designate an object or material comprising the object visible by in vivo analysis techniques for imaging such as, but not limited to, methods such as x-ray radiography, fluoroscopy, other forms of radiation, MRI, electromagnetic energy, structural imaging (such as computed or computerized tomography), and functional imaging (such as ultrasonography). The term, "inherently radiopaque", is used herein to designate a polymer that is intrinsically radiopaque due to a sufficient number of heavy atoms, such as bromine or iodine, attached thereto by covalent or ionic bonds to render the polymer easier to detect by medical imaging techniques (e.g., by X-rays and/or during fluoroscopy). Accordingly, the term does not encompass an unhalogenated polymer in which radiopacity is solely due to blending with a halogenated species or other radiopacifying agents such as metals and their complexes.

Although the inventors do not wish to be bound by or to any particular theory of operation, the inventors believe that the beneficial combination of properties associated with the medical devices of the present invention are attributable, at least in part, to certain characteristics of the polymers comprising at least one recurring unit of the formula (I), (Ia), and/or (XI), from which the devices are made.

It is understood that the polymers described herein may be used in accordance with preferred aspects of the invention as a homogeneous polymer, as a copolymer, and/or as a polymer blend. Accordingly, reference herein to a polymer of the formula (I) is understood to be a reference to a polymer that comprises a recurring unit of the formula (I), which may be a homopolymer, copolymer or blend. Also, reference herein to a polymer of the formula (Ia) is understood to be a reference to a polymer that comprises a recurring unit of the formula (Ia), which may be a homopolymer, copolymer or blend. Also, reference herein to a polymer of the formula (XI) is understood to be a reference to a polymer that comprises a recurring unit of the formula (XI), which may be a homopolymer, copolymer or blend.

Side chain crystallizable ("SCC") polymers ("SCCP"), sometimes called "comb-like" polymers, are well-known, see N. A. Plate and V. P. Shibaev, J. Polymer Sci.: Macromol. Rev. 8:117-253 (1974), the disclosure of which is hereby incorporated by reference. One type of SCCP is an inherently radiopaque side chain crystallizable polymer ("IRSCCP"). Another type of SCCP is a heavy atom-containing side-chain crystallizable polymer ("HACSCCP"). It will be understood that reference herein to SCC polymers includes both IRSCCP's and HACSCCP's, unless otherwise stated. The SCC polymers described herein can contain heavy atoms and be radiopaque. Alternatively, the SCC polymers described herein can be substantially free of heavy atoms and non-radiopaque.

IRSCCP's and HACSCCP's may be used in a variety of applications, including medical applications in which their inherent radiopacity may provide significant advantages. In certain embodiments, IRSCCP's and HACSCCP'S may be SCC polymers that have been modified to include heavy atoms, e.g., by bonding heavy atoms to an SCC polymer and/or by making an IRSCCP or HACSCCP by polymerizing monomers that contain heavy atoms. IRSCCP's and HACSCCP'S may have various configurations, e.g., homopolymer, copolymer (e.g., random copolymer, alternating copolymer, block copolymer, graft copolymer), various tacticities (e.g., random, isotactic, atactic, syndiotactic), etc. An IRSCCP or HACSCCP may be a mixture or blend of two or more IRSCCP's or HACSCCP's, respectively, each of the individual IRSCCP's or HACSCCP's in the mixture or blend having different configurations, molecular weights, melting points, etc. The polymer backbone or main chain of the IRSCCP or HACSCCP, to which the crystallizable side chains are attached, may be configured in various ways, e.g., linear, branched, crosslinked, dendritic, single-stranded, double-stranded, etc. Preferred IRSCCP's or HACSCCP's for medical applications are biocompatible and/or bioresorbable. The heavy atoms may be attached to the main chain and/or the side chains of an IRSCCP or HACSCCP.

The crystallizable side chains of SCCP's are preferably selected to crystallize with one another to form crystalline regions and may comprise, for example, —(CH2)n- and/or —((CH2)m-O—)n groups. The side chains are preferably linear to facilitate crystallization. For SCC's that contain —(CH2)n-groups in the crystallizable side chain, n is preferably in the range of about 6 to about 30, more preferably in the range of about 20 to about 30. For SCC's that contain —((CH2)m-O—)n groups in the crystallizable side chain, n is preferably in the range of about 6 to about 30 and m is preferably in the range of about 1 to about 8. More preferably, m and n are selected so that the ((CH2)m-O—)n groups contain from about 6 to about 30 carbon atoms, even more preferably from about 20 to about 30 carbon atoms. However, both m and n are not limited to any upper range, and either m or n can be a number larger than 30, including up to 40, 50, 60, 70, 80, 90, 100, or greater.

The spacing between side chains and the length and type of side chain are preferably selected to provide the resulting SCCP with a desired melting point. For example, for medical applications (e.g., embolotherapy), the spacing between side chains and the length and type of the side chains are preferably selected to provide the SCCP (and/or the material into which it is incorporated) with a melting point in the range of about 30° C. to about 80° C. As the spacing between side chains increases, the tendency for the side chains to be crystallizable tends to decrease. Likewise, as the flexibility of the side chains increases, the tendency for the side chains to be crystallizable tends to decrease. On the other hand, as the length of the side chains increases, the tendency for the side chains to be crystallizable tends to increase. In many cases, the length of the crystallizable side chain may be in the range of about two times to about ten times the average distance between crystallizable side chains.

Examples of SCC polymers include versions of the following polymers that are selected so that the alkyl group is sufficiently long (e.g., greater than about 6 carbons) to provide the desired melting point and, for HACSCCP's, modified to include heavy atoms, e.g., sufficient heavy atoms to render them radiopaque: poly(1-alkene)s, poly(alkyl acrylate)s, poly(alkyl methacrylate)s, poly(alkyl vinyl ether)s, and poly(alkyl styrene)s. Examples of SCC polymers further include versions of the polymers disclosed in the following references that include (or have been modified to include) crystallizable side chains and, for HACSCCP's, heavy atoms, e.g., sufficient heavy atoms to render them radiopaque: U.S. Pat. Nos. 4,638,045; 4,863,735; 5,198,507; 5,469,867; 5,912,225; and 6,238,687; as well as U.S. Provisional Patent Application No. 60/601,526, filed 13 Aug. 2004; all of which are incorporated by reference in their entireties, and particularly for the purpose of describing SCC polymers and methods for making them.

In an embodiment, the side chains are selected to provide the SCC polymer (or material into which the SCC polymer is incorporated) with a controllable melting temperature. In a preferred embodiment, polymeric embolotherapy products include SCCP's configured to render the embolotherapy product detectable by a technique such as X-ray. The side chains of the included SCCP may be selected so that the polymeric embolotherapy product has a melting point higher than the body temperature of the mammal for which the product is intended. Such a polymeric embolotherapy product may, for example, be heated above the melting temperature to render it more flowable, thereby facilitating delivery to the target vasculature, where it may cool and solidify to embolize the vasculature. The use of inherently radiopaque SCCP's to provide radiopacity and a controlled melting point may be particularly advantageous in medical applications, but those skilled in the art will recognize additional applications as well. Thus, while the various descriptions herein regarding the use of SCC polymers may indicate a preference for medical applications, it will be understood that various technologies outside the medical area may also benefit from the use of SCC polymers.

Furthermore, in some embodiments, the present SCC polymers may be used to develop various medical devices. For instance, pre-fabricated off-the-shelf devices, rapidly prototyped devices, real-time prototype devices using computer technology. Additionally present polymers may be delivered directly to a non-lumen or non-cavity of the body. The various medical devices may include but are not limited to stents and stent grafts for vascular and body lumen applications, pins, screws, sutures, anchors and plates for reconstructive skeletal or soft tissue applications, cartilage replacements. SCC polymers may be placed directly in body tissue for example in subcutaneous and intramuscular tissue.

An embodiment provides a polymer that comprises a recurring unit of the formula (I):

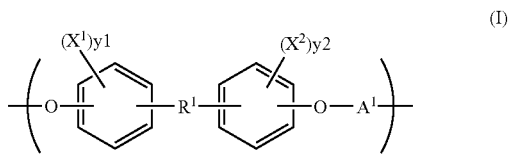

(I)

wherein $X^1$ and $X^2$ in formula (I) are each independently selected from the group consisting of Br and I; $y^1$ and $y^2$ in formula (I) are each independently zero or an integer in the range of 1 to 4; $A^1$ in formula (I) is selected from the group consisting of

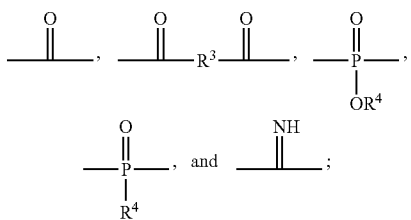

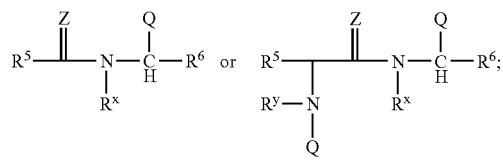

$R^3$ in formula (I) is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl; $R^4$ in formula (I) selected from the group consisting of H, $C_1$-$C_{30}$ alkyl, and $C_1$-$C_{30}$ heteroalkyl; $R^1$ in formula (I) is

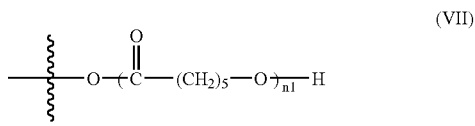

Z in formula (I) is O or S; $R^5$ and $R^6$ in formula (I) are each independently selected from the group consisting of —CH=CH—, —CHJ$^1$-CHJ$^2$-, and —(CH$_2$)$_a$—; a in formula (I) is zero or an integer in the range of 1 to 8; $J^1$ and $J^2$ in formula (I) are each independently selected from the group consisting of H, Br, and I; Q in formula (I) is a group comprising about 20 or more carbon atoms; $R^x$ in formula (I) is selected from optionally substituted branched or unbranched $C_1$-$C_{30}$ alkyl and optionally substituted $C_6$-$C_{30}$ aryl; and $R^y$ in formula (I) is selected from hydrogen, optionally substituted branched, or unbranched $C_1$-$C_{30}$ alkyl and optionally substituted $C_6$-$C_{30}$ aryl.

In an embodiment, the polymer comprising a recurring unit of formula (I) comprises an IRSCCP. In an embodiment, the polymer comprising a recurring unit of formula (I) comprises an HACSCCP. In an embodiment, the polymer comprising a recurring unit of formula (I) comprises both an IRSCCP and a HACSCCP. In an embodiment, $R^x$ in formula (I) is an alkyl group. In an embodiment, $R^x$ in formula (I) is a branched or unbranched $C_1$-$C_6$ alkyl. In an embodiment, $R^x$ in formula (I) is a methyl.

$X^1$ and $X^2$ in formula (I) can be independently selected to be any halogen atom. In an embodiment, $X^1$ and $X^2$ in formula (I) are each I. In an embodiment, $X^1$ and $X^2$ in formula (I) are each Br.

In an embodiment, $A^1$ in formula (I) is

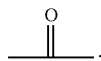

In an embodiment, $R^1$ in formula (I) is

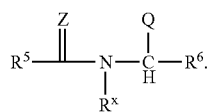

In an embodiment, Z in formula (I) is O. In an embodiment, $R^5$ and $R^6$ in formula (I) are each independently selected from the group consisting of —CH=CH— and —(CH$_2$)$_a$—.

In an embodiment, Q in formula (I) comprises from about 20 to about 30 carbon atoms. In embodiment, Q in formula (I) is crystallizable. In an embodiment, Q in formula (I) is non-crystallizable. In an embodiment, Q in formula (I) includes an ester group. In an embodiment, Q is

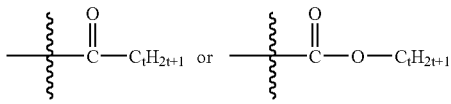

wherein t in the above groups is independently an integer in the range of about 1 to about 30. In an embodiment, t in the above groups is independently an integer in the range of about 6 to about 30. In an embodiment, t in the above groups is independently an integer in the range of about 20 to about 30.

In an embodiment, Q in formula (I) is a group that comprises the formula (VII):

$$-\!\!\!\xi\!-\!\!O-\!\!\!\left(\!\!\begin{array}{c}O\\\|\\C\end{array}\!\!-\!(CH_2)_5-\!O\!\right)_{\!\!n1}\!\!\!-H \qquad (VII)$$

wherein n1 in formula (VII) is an integer in the range of about 1 to about 1,000. In an embodiment, n1 in formula (VII) is an integer in the range of about 1 to about 30. In an embodiment, n1 in formula (VII) is an integer in the range of about 20 to about 30. In an embodiment, n1 in formula (VII) is an integer in the range of about 30 to about 100. In an embodiment, n1 in formula (VII) is an integer in the range of about 100 to about 500. In an embodiment, n1 in formula (VII) is an integer in the range of about 500 to about 1,000.

In an embodiment, $R^5$ in formula (I) is —CH=CH— or —(CH$_2$)$_a$—, $R^6$ in formula (I) is —(CH$_2$)$_a$—, and Q in formula (I) is an ester group comprising from about 20 to about 30 carbon atoms.

It will be recognized that Q and/or $R^4$ in formula (I) may comprise crystallizable side chains, that each of X, $J^1$ and $J^2$ may be a heavy atom, and that y may be adjusted so that the number of heavy atoms in the polymer is sufficient to render the polymer radiopaque. Q and $R^4$ in formula (I) may each independently comprise units selected from the group consisting of —(CH$_2$)$_{m1}$— and —((CH$_2$)$_{m1}$—O—)$_{n1}$; where m1 and n1 are each independently selected so that Q and/or $R^4$ in formula (I) each independently contain from about 1 to about 30 carbon atoms, preferably from about 6 to about 30 carbon atoms, and more preferably from about 20 to 30 carbon atoms. Moreover, Q and $R^4$ in formula (I) may include other functional groups such as ester and amide, and/or heavy atoms such as iodine and bromine. Non-limiting examples of Q and $R^4$ in formula (I) thus include —C$_{n1}$H$_{2n1+1}$, —CO$_2$—C$_{n1}$H$_{2n1+1}$, —CONH—C$_{n1+1}$, —(CH$_2$)$_{n1}$—Br, —(CH$_2$)$_{n1}$—I, —CO$_2$H$_{2n1}$—(CH$_2$)$_{n1}$—Br, —CO$_2$—(CH$_2$)$_{n1}$—I, —CONH—CO$_2$—(CH$_2$)$_{n1}$—Br, and —CONH—CO$_2$—(CH$_2$)$_{n1}$—I. In an embodiment, $R^5$ in formula (I) is —CH=CH— or —(CH$_2$)$_a$—; $R^6$ in formula (I) is =(CH$_2$)$_a$—; and Q in formula (I) is an ester group comprising from about 10 to about 30 carbon atoms.

A polymer comprising a recurring unit of formula (I) can be copolymerized with any number of other recurring units. It will be understood that a polymer that comprises a recurring unit of the formula (I) may be a copolymer, e.g., a polymer of the formula (I) that further comprises recurring —R$^2$-A$^2$- units, where $R^2$ in formula (I) is selected from the group consisting of $-(CH_2)_{n2}-$ and $-((CH_2)_{m2}-O-)_{n2}$; where m2 and n2 in formula (I) are each independently selected so that $R^2$ in formula (I) contains from about 1 to about 30 carbon atoms; and where $A^2$ in formula (I) is defined in the same manner as $A^1$ in formula (I) above.

In embodiment, a polymer comprising a recurring unit of the formula (I) further comprises a recurring unit of the formula (II):

wherein $R^7$ in formula (II) is H or $CH_3$; $A^3$ in formula (II) is a chemical group having a molecular weight of about 500 or less; and $A^3$ in formula (II) bears at least one heavy atom attached to the polymer. Non-limiting examples of $A^3$ in formula (II) include metal carboxylate (e.g., $-CO_2Cs$), metal sulfonate (e.g., $-SO_4Ba$), halogenated alkyl ester (e.g., $-CO_2-(CH_2)_b-Br$), halogenated alkyl amide (e.g., $-CONH-(CH_2)_b-Br$), and halogenated aromatic (e.g., $-C_6H_4-I$), where b is an integer in the range of about 1 to about 4. In an embodiment, $A^3$ in formula (I) comprises an aromatic group bearing at least one halogen atom selected from the group consisting of bromine and iodine. In another embodiment, $A^3$ in formula (II) comprises a chemical group of the formula $-L_1-(CH_2)_{n3}-L_2-Ar^1$, wherein $L_1$ and $L_2$ each independently represent a nullity (i.e., are not present), ester, ether or amide group; n3 is zero or an integer in the range of about 1 to about 30; and $Ar^1$ comprises a halogenated aromatic group containing from about 2 to about 20 carbon atoms. SCCP's that comprise a recurring unit of the formula (II) may be formed by polymerization of the corresponding monomers or by post-reaction of appropriate polymeric precursors. SCCP's that comprise a recurring unit of the formula (II) may be copolymers that include additional recurring units.

Side chain $A^3$ groups in a SCCP comprising a recurring unit of the formula (II) may be crystallizable and/or the SCCP comprising a recurring unit of the formula (II) may further comprise a second recurring unit that comprises a crystallizable side chain. Examples of suitable second recurring units having crystallizable side chains include the following: poly(1-alkene)s, poly(alkyl acrylate)s, poly(alkyl methacrylate)s, poly(alkyl vinyl ether)s, and poly(alkyl styrene)s. The alkyl groups of the foregoing exemplary second recurring units preferably contain more than 6 carbon atoms, and more preferably contain from about 6 to about 30 carbon atoms. For example, in an embodiment, the second recurring unit is of the formula (III):

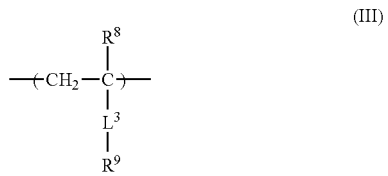

wherein $R^8$ in formula (III) is H or $CH_3$; $L^3$ in formula (III) is an ester or amide linkage; and $R^9$ in formula (III) comprises a $C_6$-$C_{30}$ hydrocarbon group. SCCP's comprising a recurring unit of the formula (II) and a second recurring unit (such as a recurring unit of the formula (III)) may be formed by copolymerization of the corresponding monomers and/or by post-reaction of appropriate polymeric precursors. In an embodiment, the polymer comprising a recurring unit of the formula (I) further comprises a recurring unit of the formula (III), whether or not a recurring unit of the formula (II) is present.

In an embodiment, the polymer comprising a recurring unit of formula (I) further comprises a recurring unit of the formula (IV):

wherein $A^4$ in formula (IV) represents H or a chemical group containing from about 1 to about 30 carbons; $A^3$ in formula (IV) is a chemical group having a molecular weight of about 500 or less; and $A^3$ in formula (IV) bears at least one heavy atom attached to the polymer. Side chain $A^3$ and/or $A^4$ groups in a SCCP comprising a recurring unit of the formula (IV) may be crystallizable and/or the SCCP comprising a recurring unit of the formula (IV) may further comprise a second recurring unit that comprises a crystallizable side chain. For example, in an embodiment, the second recurring unit is of the formula (V):

wherein $R^{10}$ in formula (V) comprises a $C_6$ to $C_{30}$ hydrocarbon group and $R^{11}$ in formula (V) represents H or a $C_1$ to $C_{30}$ hydrocarbon group. In an embodiment, the polymer comprising a recurring unit of the formula (I) further comprises a recurring unit of the formula (III), whether or not a recurring unit of the formula (VI) is present.

In an embodiment, the polymer comprising a recurring unit of formula (I) further comprises a recurring unit of the formula (VI):

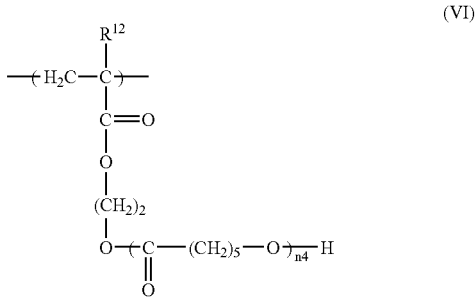

wherein $R^{12}$ in formula (VI) is H or $CH_3$ and n4 in formula (VI) is an integer in the range of about 1 to about 1,000. In an embodiment, n4 in formula (VI) is an integer in the range of about 1 to about 30. In an embodiment, n4 in formula (VI) is an integer in the range of about 20 to about 30. In an embodiment, n4 in formula (VI) is an integer in the range of about 30 to about 100. In an embodiment, n4 in formula (VI) is an integer in the range of about 100 to about 500. In an embodiment, n4 in formula (VI) is an integer in the range of about 500 to about 1,000.

Recurring units of the formula (VI) may be formed in various ways. For example, a starting polymer comprising recurring hydroxyethylmethacrylate (HEMA) units may be provided, and at least a portion of those recurring hydroxyethylmethacrylate (HEMA) units may be reacted with caprolactone to form recurring units of the formula (VIa) having crystallizable poly(caprolactone) (PCL) groups in the side chain as illustrated in Scheme A below.

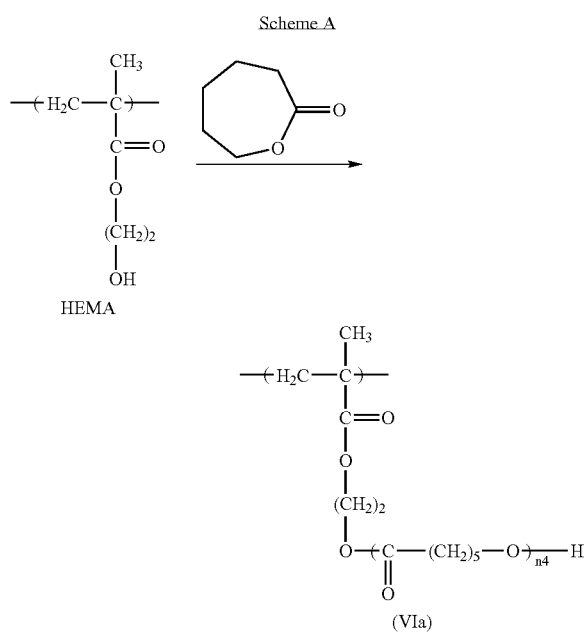

Polymerization of the caprolactone to form the crystallizable PCL groups may be conducted by using an appropriate catalyst, e.g., stannous octoate. The melting point of the side chain (and the SCCP) may be controlled by manipulating the degree of polymerization (n4) of the PCL groups, e.g., by adjusting the relative amounts of HEMA recurring units and caprolactone monomer during polymerization, in a manner generally know to those skilled in the art. The melting point may also be controlled by manipulating the spacing along the polymer backbone between PCL groups, e.g., by appropriate selection of the amount of HEMA recurring units in the starting polymer. In an embodiment, n4 in formula (VI) is an integer in the range of about 2 to about 10. Heavy atoms may be included in a SCCP that comprises a recurring unit of the formula (VI) in various ways, e.g., the SCCP may further comprise a recurring unit of the formula (II) as described above.

SCC polymers are not limited to those described above (e.g., not limited to SCCP's comprising recurring units of the formulae (I) to (VI)), and further include versions of known polymers that have been modified to include side-chain crystallizable groups and/or sufficient heavy atoms to render the resulting polymer radiopaque. Those skilled in the art will understand that SCCP's may be prepared in various ways, e.g., by employing routine experimentation to modify known methods for making SCC polymers to thereby incorporate heavy atoms into the resulting polymers. For example, inherently radiopaque versions of the side chain crystallizable polymers described in U.S. Pat. No. 5,469,867 may be prepared by copolymerizing the corresponding monomers with monomers that contain heavy atoms. U.S. Pat. No. 5,469,867 is incorporated by reference and particularly for the purpose of describing monomers, polymers and methods of polymerization. Examples of suitable monomers that contain heavy atoms are disclosed in Kruft, et al., "Studies On Radioopaque Polymeric Biomaterials With Potential Applications To Endovascular Prostheses," Biomaterials 17 (1996) 1803-1812; and Jayakrishnan et al., "Synthesis and Polymerization of Some Iodine-Containing Monomers for Biomedical Applications," J. Appl. Polm. Sci., 44 (1992) 743-748. SCCP's may also be prepared by post-reaction, e.g., by attaching heavy atoms to the polymers described in U.S. Pat. No. 5,469,867. Specific examples of SCC polymers that may be modified with heavy atoms to make SCCP's include the acrylate, fluoroacrylate, methacrylate and vinyl ester polymers described in J. Poly. Sci., 10.3347 (1972); J. Poly. Sci. 10:1657 (1972); J. Poly. Sci. 9:3367 (1971); J. Poly. Sci. 9:3349 (1971); J. Poly. Sci. 9:1835 (1971); J.A.C.S. 76:6280 (1954); J. Poly. Sci. 7:3053 (1969); Polymer J. 17:991 (1985), corresponding acrylamides, substituted acrylamides and maleimide polymers (J. Poly. Sci.: Poly. Physics Ed. 11:2197 (1980); polyolefin polymers such as those described in J. Poly. Sci.: Macromol. Rev. 8:117-253 (1974) and Macromolecules 13:12 (1980), polyalkyl vinylethers, polyalkylethylene oxides such as those described in Macromolecules 13:15 (1980), alkylphosphazene polymers, polyamino acids such as those described in Poly. Sci. USSR 21:241, Macromolecules 18:2141, polyisocyanates such as those described in Macromolecules 12:94 (1979), polyurethanes made by reacting amine- or alcohol-containing monomers with long-chain alkyl isocyanates, polyesters and polyethers, polysiloxanes and polysilanes such as those described in Macromolecules 19:611 (1986), and p-alkylstyrene polymers such as those described in J.A.C.S. 75:3326 (1953) and J. Poly. Sci. 60:19 (1962). The foregoing SCC polymers may be modified with heavy atoms to make SCCP's in various ways. For example, monomers bearing heavy atoms may be prepared by iodinating and/or brominating the monomers used to make the foregoing polymers. Those heavy atom-bearing monomers may then be copolymerized with the unmodified monomers to prepare SCCP's. Those skilled in the art may identify conditions for making the heavy atom-bearing monomers and corresponding SCCP's by routine experimentation.

In another embodiment, a SCCP is prepared by reacting a side chain crystallizable polymer with a heavy metal reagent under conditions selected to attach a plurality of heavy atoms to the side chain crystallizable polymer. For example, the side chain crystallizable polymer may be exposed to a heavy metal reagent that comprises bromine and/or iodine. Examples of heavy metal reagents include bromine vapor, iodine vapor, bromine solution and iodine solution. The side chain crystallizable polymer may be exposed to the heavy metal reagent by, e.g., exposing or intermixing the solid polymer with heavy metal reagent and/or by dissolving or dispersing the side chain crystallizable polymer in a solvent and intermixing with the heavy metal reagent. Other methods may also be used.

SCC polymers may contain various amounts of heavy atoms and/or crystallizable side chains, depending on the properties desired for the SCC polymer. Preferably, the content of crystallizable side chains is sufficient to substantially reduce or prevent main chain crystallization. In many cases, the amount of crystallizable side chain in the SCC polymer is in the range of about 20% to about 80% by weight, based on total polymer weight, and in some cases may be in the range of about 35% to about 65%, same basis. The length of the SCC polymer crystallizable side chain is preferably in the range of about two times to about ten times the average distance between crystallizable side chains. SCC polymers may comprise a crystalline region (e.g., formed by crystallization of the side chains below the melting point of the polymer) and a non-crystalline region (e.g., a glassy or elastomeric region formed by the non-crystallizable portions of the SCC polymer). In an embodiment, the non-crystalline region has a glass transition temperature that is higher than the body temperature of a mammal, e.g., higher than about 37° C.; in another embodiment, the non-crystalline region has a glass transition temperature that is lower than the body temperature of a mammal, e.g., lower than about 37° C. The amount of heavy atoms in a particular SCC polymer may be selected based on the degree of radiopacity and/or material (mechanical) properties desired. For example, for medical applications, a SCCP preferably contains from about 1% to about 90% heavy atoms, more preferably about 20% to about 50% by heavy atoms, by weight based on total weight of the SCCP. In some cases, the SCC polymer is incorporated into a polymeric material and/or formed into a medical device as described below. When the SCC polymer is a HACSCCP and/or IRSCCP, the amount of heavy atoms in the HACSCCP and/or IRSCCP may be adjusted to provide the resulting polymeric material and/or medical device with the desired degree of radiopacity.

The indiscriminate incorporation of heavy atoms into side chain crystallizable polymers often disrupts or prevents otherwise crystallizable side chains from crystallizing, particularly when the levels of heavy atom incorporation are high, the side chains are relatively short, the side chains are relatively flexible, and/or the distance between side chains is relatively large. Preferably, the heavy atoms are attached to the SCCP in a manner that minimizes or eliminates disruption of side chain crystallinity. For example, in an embodiment, at least about 50%, preferably at least about 80%, of the heavy atoms are attached to the main chain of the SCCP. In another embodiment, at least about 50%, preferably at least about 80%, of the heavy atoms are attached to the ends of the side chains of the SCCP, e.g., to the ends of the crystallizable side chains and/or to non-crystallizable side chains. In another embodiment, at least about 50%, preferably at least about 80%, of the heavy atoms are attached to either the main chain or the side chains (crystallizable and/or non-crystallizable) of the SCCP. In another embodiment, the SCCP is a block copolymer that comprises a crystalline block and an amorphous block, and at least about 50%, preferably at least about 80%, of the heavy atoms are attached to the amorphous block.

The molecular weight of SCC polymers may be selected in view of the intended application for the polymer. For example, in some medical applications, e.g., for certain embolotherapy applications, it is desirable for the SCC polymer to flow at temperatures higher than the polymer melting point and to form a solid at temperatures below the polymer melting point. The viscosity of a molten SCC polymer generally increases as the molecular weight of the polymer increases, and thus the molecular weight of a particular SCC polymer is preferably selected to provide the desired molten polymer viscosity. For example, a suitable molecular weight range for SCC polymers used in embolotherapy products may be in the range of from about 2,000 to about 250,000, preferably from about 5,000 to about 150,000. Molecular weights are weight average as determined by high pressure size exclusion chromatography using light scattering detection.

In some cases, it may be desirable to mix or blend the SCC polymer with a second material (e.g., a second polymer) to form a polymeric material, which may then be employed in the intended application. For example, an embodiment provides a polymeric material that comprises a SCC polymer (e.g., a HACSCCP, a IRSCCP, or both) and a second polymer. Preferably, the second polymer is biocompatible and/or bioresorbable. Examples of second polymers suitable for mixing or blending with SCC polymers to form polymeric materials include the non-inherently radiopaque polymers disclosed in U.S. Pat. No. 5,469,867 and the radiopaque polymers described in U.S. Provisional Patent Application No. 60/601,526, filed 13 Aug. 2004, both of which are incorporated by reference. Depending on the intended application, the relative amounts of SCC polymer and second polymer in the polymeric material may vary over a broad range. For example, in an embodiment, a polymeric material comprises from about 1% to about 100% of a SCC polymer and up to about 99% of a second polymer, by weight based on total. Since a polymeric material may consist solely of SCC polymer, it will be appreciated that the term "polymeric material" as used herein includes SCC polymers). As noted above, it will be understood that the SCC polymer itself may be a mixture or blend of two or more individual SCC polymers, each having, for example, different molecular weights, configurations and/or melting points.

A polymeric material that comprises a SCC polymer may be formed into various configurations or pre-formed shapes, e.g., a rod, a particle, or a sheet. A rod may be linear, coiled, hollow, highly elongated (e.g., a string or strand), and may have various cross-sections shapes, e.g., substantially round, substantially elliptical, substantially triangular, substantially rectangular, irregular, etc. A particle may be a spherical particle, a geometrically non-uniform particle (e.g., a flake or chip), a porous particle, a hollow particle, a solid particle, etc. A particle preferably has a excluded diameter of from about 10 microns to about 5,000 microns.

The configuration of the polymeric material may depend on various factors such as the intended application, shipping constraints, processing constraints, etc. For example, an embodiment provides a medical device that comprises a polymeric material. The polymeric material may comprise a SCC polymer. Non-limiting examples of medical devices that may comprise an SCC polymer include, for example, a stent (e.g., an expandable stent), stent graft, annuloplasty ring, vascular graft, suture, vascular cuff, septal defect repair device, heart valve, heart valve component, heart valve repair device, closure device, inducer of vasculature and connective tissue proliferation, catheter (e.g., balloon catheter configured to deliver a stent) and/or a tissue engineered implant. Various medical device embodiments are described in greater detail below. It will be appreciated that a medical device may consist solely of a polymeric material that consists solely of a SCC polymer. For example, in an embodiment, a medical device is configured to be deliverable (e.g., by injection, catheter, physical insertion, pouring, a heated rod, spraying and/or squirting) to a body cavity of a mammal. Such a device may be, for example, an embolotherapy product formed primarily of a polymeric material that comprises a SCCP. Thus, while certain descriptions below may be directed to medical devices, it will be understood that such descriptions also apply to polymeric materials and to SCC polymers, unless the context indicates otherwise. Likewise, descriptions herein of polymeric materials and of SCC polymers also apply to medical devices, unless the context indicates otherwise.

A polymer comprising a recurring unit of the formula (I) can be copolymerized with any combination of the recurring units of formulas (I), (III), (IV), (V), (VI) and/or any other commonly known recurring unit.

Provided herein is a method for making a polymer that comprises a recurring unit of the formula (I). In an embodiment, the method of making the polymer comprises attaching an N-substituent during the synthesis of a corresponding monomer. In an embodiment, the method of making the polymer comprises attaching an N-substituent during polymerization of a corresponding monomer. In an embodiment, the method of making the polymer comprises attaching an N-substituent after polymerization of a corresponding monomer. Methods of making a polymer comprising a recurring unit of the formula (I) are further discussed in detail below.

An embodiment provides an inherently radiopaque, biocompatible, bioresorbable polymer comprising one or more recurring units of the formula (Ia):

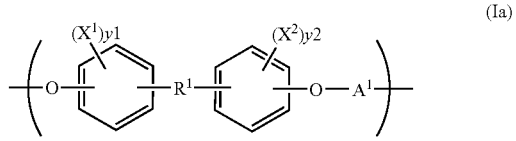

(Ia)

wherein $X^1$ and $X^2$ in formula (Ia) are each independently selected from the group consisting of Br and I; y1 and y2 in formula (Ia) are each independently zero or an integer in the range of 1 to 4, with the proviso that the sum of y1 and y2 in formula (Ia) is at least 1; $R^1$ in formula (Ia) is

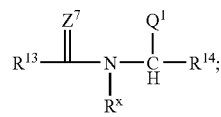

$R^x$ in formula (Ia) is selected from optionally substituted branched or unbranched $C_1$-$C_{30}$ alkyl and optionally substituted $C_6$-$C_{30}$ aryl; $R^{13}$ and $R^{14}$ in formula (Ia) are each independently selected from the group consisting of —CH=CH—, —$(CH_2)_c$—, —$(CHJ^1)$-, —$CHJ^2$-$CHJ^3$-, —CH=CH—$(CHJ^1)$-, and —$(CH_2)_c$—$(CHJ^1)$-; c in formula (Ia) is zero or an integer in the range of 1 to 8; $J^1$, $J^2$ and $J^3$ in formula (Ia) are each independently selected from the group consisting of H, Br, I, —NH-$Q^2$ and —C(=$Z^8$)—$OQ^3$; $Q^1$, $Q^2$ and $Q^3$ in formula (Ia) are each independently H, a group comprising from about 1 to about 30 carbons, or a group that comprises the formula (VIIa):

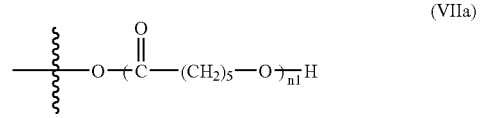

(VIIa)

wherein n1 in formula (VIIa) is an integer in the range of about 1 to about 1,000; $Z^7$ and $Z^8$ in formula (Ia) are each independently O or S; $A^1$ in formula (Ia) is selected from the group consisting of

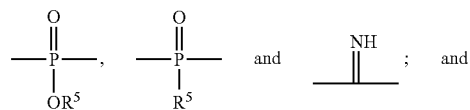

$R^5$ in formula (Ia) is selected from the group consisting of H, $C_1$-$C_{30}$ alkyl, and $C_1$-$C_{30}$ heteroalkyl.

In some embodiments, the $X^1$ and $X^2$ groups on the polymer comprising a recurring unit of formula (Ia) are iodine. In other aspects of the invention, the polymer comprises a backbone which is not naturally occurring. Alternatively and/or additionally, the polymer may comprise a backbone comprising at least one amino acid derivative.

In an embodiment, $R^x$ in formula (Ia) is a branched or unbranched $C_1$-$C_6$ alkyl. In an embodiment, $R^x$ in formula (Ia) is methyl. In an embodiment, $Q^1$, $Q^2$ and/or $Q^3$ in formula (Ia) are each independently H or a non-crystallizable group comprising from about 1 to about 30 carbons. In an embodiment, $Q^1$, $Q^2$ and/or $Q^3$ in formula (Ia) is a group comprising from about 20 to about 30 carbons. In an embodiment, $Q^1$, $Q^2$ and/or $Q^3$ in formula (Ia) includes an ester group. In an embodiment, $Q^1$, $Q^2$ and/or $Q^3$ in formula (Ia) is

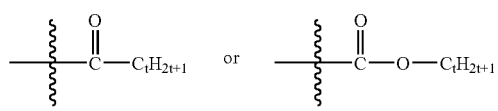

wherein t in the above groups is independently an integer in the range of about 1 to about 30. In an embodiment, t in the above groups is independently an integer in the range of about 6 to about 30. In an embodiment, t in the above groups is independently an integer in the range of about 20 to about 30.

In an embodiment, $Q^1$, $Q^2$ and $Q^3$ in formula (Ia) is a group comprising the formula (VIIa):

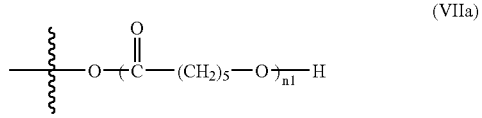

(VIIa)

wherein n1 in formula (VIIa) is an integer in the range of about 1 to about 1,000. In an embodiment, n1 in formula (VIIa) is an integer in the range of about 1 to about 30. In an embodiment, n1 in formula (VIIa) is an integer in the range of about 20 to about 30. In an embodiment, n1 in formula (VIIa) is an integer in the range of about 30 to about 100. In an embodiment, n1 in formula (VIIa) is an integer in the range of about 100 to about 500. In an embodiment, n1 in formula (VIIa) is an integer in the range of about 500 to about 1,000.

In an embodiment $X^1$ and $X^2$ in formula (Ia) are each I; $R^1$ in formula (Ia) is

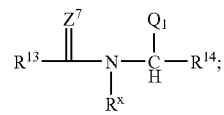

$Z^7$ in formula (Ia) is O; and $R^{13}$ and $R^{14}$ in formula (Ia) are each independently selected from the group consisting of —CH=CH— and —$(CH_2)_c$—.

A polymer comprising a recurring unit of formula (Ia) can be copolymerized with any number of other recurring units. In an embodiment, the polymer comprising a recurring unit of formula (Ia) further comprises a recurring unit of the formula (IIa):

(IIa)

wherein B in formula (IIa) is —O—((CHR$^6$)$_p$—O)$_q$—; R$^6$ in formula (IIa) is H or C$_1$ to C$_3$ alkyl; p and q in formula (IIa) are each individually an integer in the range of about 1 to about 100; A$^2$ in formula (IIa) is selected from the group consisting of

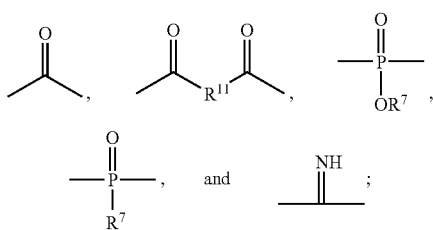

R$^7$ in formula (IIa) is H or a C$_1$-C$_{30}$ hydrocarbon; and R$^{11}$ in formula (IIa) is selected from the group consisting of C$_1$-C$_{30}$ alkyl, C$_1$-C$_{30}$ heteroalkyl, C$_5$-C$_{30}$ aryl, C$_6$-C$_{30}$ alkylaryl, and C$_2$-C$_{30}$ heteroaryl.

In an embodiment, the polymer comprising a recurring unit of the formula (Ia) further comprises one or more recurring units of the formula (Ib):

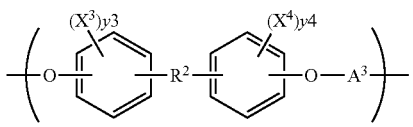
(Ib)

wherein X$^3$ and X$^4$ in formula (Ib) are each independently selected from the group consisting of Br and I; y3 and y4 in formula (Ib) are each independently zero or an integer in the range of 1 to 4; R$^2$ in formula (Ib) is selected from the group consisting of:

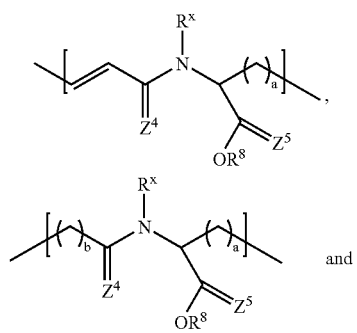

and

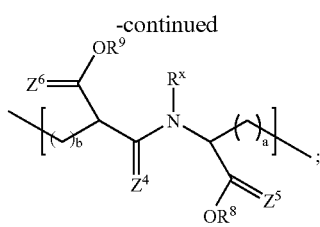

R$^x$ in formula (Ib) is selected from optionally substituted branched or unbranched C$_1$-C$_{30}$ alkyl and optionally substituted C$_6$-C$_{30}$ aryl; R$^8$ and R$^9$ in formula (Ib) are each independently H or a non-crystallizable C$_1$ to C$_{30}$ hydrocarbon; Z$^4$, Z$^5$ and Z$^6$ in formula (Ib) are each independently O or S; a and b in formula (Ib) are each independently an integer in the range of 1 to 8; A$^3$ in formula (Ib) is selected from the group consisting of

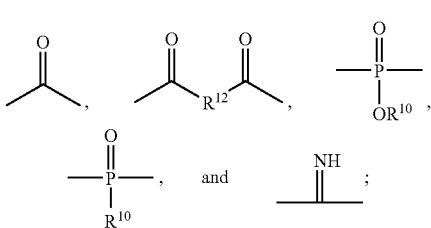

R$^{10}$ in formula (Ib) is selected from the group consisting of H, C$_1$-C$_{30}$ alkyl, and C$_1$-C$_{30}$ heteroalkyl; and R$^{12}$ in formula (Ib) is selected from the group consisting of C$_1$-C$_{30}$ alkyl, C$_1$-C$_{30}$ heteroalkyl, C$_5$-C$_{30}$ aryl, C$_6$-C$_{30}$ alkylaryl, and C$_2$-C$_{30}$ heteroaryl.

In an embodiment, R$^1$ in formula (Ia) is

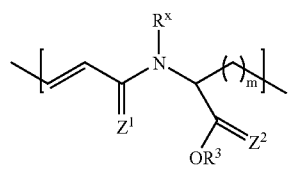

wherein R$^x$ in formula (Ia) is selected from optionally substituted branched or unbranched C$_1$-C$_{30}$ alkyl and optionally substituted C$_6$-C$_{30}$ aryl; R$^3$ in formula (Ia) is H or a non-crystallizable C$_1$ to C$_{29}$ hydrocarbon; Z$^1$ and Z$^2$ in formula (Ia) are each independently O or S; and m in formula (Ia) is an integer in the range of 1 to 8.

In an embodiment, R$^1$ in formula (Ia) is wherein R$^x$ in formula (Ia) is selected from optionally substituted branched or unbranched C$_1$-C$_{30}$ alkyl and optionally substituted C$_6$-C$_{30}$ aryl; R$^3$ in formula (Ia) is H or a non-crystallizable C$_1$ to C$_{29}$ hydrocarbon; Z$^1$ and Z$^2$ in formula (Ia) are each independently or S; and j and m in formula (Ia) are each independently an integer in the range of 1 to 8.

In an embodiment, $R^1$ in formula (Ia) is

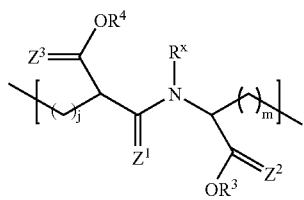

wherein $R^x$ in formula (Ia) is selected from optionally substituted branched or unbranched $C_1$-$C_{30}$ alkyl and optionally substituted $C_6$-$C_{30}$ aryl; $R^3$ and $R^4$ in formula (Ia) are each independently H or a non-crystallizable $C_1$ to $C_{29}$ hydrocarbon; $Z^1$, $Z^2$ and $Z^3$ in formula (Ia) are each independently O or S; and j and m in formula (Ia) are each independently an integer in the range of 1 to 8.

Preferred polymers comprising a recurring unit of the formula (Ia) contain combinations of derivatives of structural units selected from dicarboxylic acids, halogenated (e.g., iodinated or brominated) derivatives of desaminotyrosyl-tyrosine and poly(alkylene glycols), which exhibit desirable physicomechanical and physicochemical properties that are consistent with their use in fabrication of medical devices, including stents. For example, the stents described in accordance with preferred embodiments of the present invention:

(a) are sufficiently radiopaque to be visible by conventional X-ray fluoroscopy; (b) are of sufficient strength to support medically relevant levels of radial compression within an artery or surrounding tissue; and/or (c) have a desirable resorption profile that may be adjusted to account for the needs of a range of applications requiring the presence of a stent for different lengths of time or for the elution of therapeutics.

Although the inventors do not wish to be bound by or to any particular theory of operation, the inventors believe that the beneficial combination of properties associated with the medical devices of the present invention are attributable, at least in part, to certain characteristics of the polymers of formula (Ia), from which the devices are made.

It is understood that the polymers described herein may be used in accordance with preferred aspects of the invention as a homogeneous polymer, as a copolymer, and/or as a polymer blend. Accordingly, reference herein to a polymer of the formula (Ia) is understood to be a reference to a polymer that comprises a recurring unit of the formula (Ia), which may be a homopolymer, copolymer or blend.

The bioresorbable, inherently radiopaque stents disclosed in accordance with preferred embodiments of the present invention may be used, for example, to temporarily treat a blood vessel as in traditional applications which generally include delivery through a catheter.

Applicants have discovered that a biocompatible, bioresorbable, inherently radiopaque polymer class may be produced from a broad class of aryl-containing biocompatible, bioresorbable polymers. For example, in all of the biocompatible, bioresorbable polymers noted in the table below, radiopacity may be introduced to the aromatic rings via halogenation, particularly bromination and iodination, by well-known techniques that may be readily employed by those of ordinary skill in the art without undue experimentation, in light of the disclosure provided herein. U.S. Pat. No. 6,475,477 reveals a broad class of inherently radiopaque, biocompatible, bioresorbable polymers made in this manner. Radiopacity may be imparted to the other polymers in Table 1 in a like fashion, e.g., by halogenation of the monomers from which the polymers are made and/or by halogenation of the polymer itself. The entire disclosures of each of the patents listed in TABLE 1 are incorporated herein by reference, and particularly for the purposes of describing the manner in which the various polymers are made.

TABLE 1

| U.S. Pat. No. | Patent Title | What is taught |
| --- | --- | --- |
| 4,863,735 | Biodegradable polymeric drug delivery system with adjuvant activity | Poly(iminocarbonate) syntheses |
| 4,980,449 | Polyiminocarbonate synthesis | Polyiminocarbonate syntheses |
| 6,238,687 | Biodegradable polymers, compositions, articles and methods for making and using the same | Processes for preparing phosphorus and desaminotyrosyl L-tyrosine linkages in the polymer backbone |
| 5,912,225 | Biodegradable poly (phosphoester-co-desaminotyrosyl L-tyrosine ester) compounds, compositions, articles and methods for making and using the same | Processes for preparing polymers containing phosphorus and desaminotyrosyl L-tyrosine linkages |
| 4,638,045 | Non-peptide polyamino acid bioerodible polymers | Polymers with a plurality of monomer units of two or three amino acids |

Certain halogenated compositional variations of the above-described polymers from TABLE 1 may be represented generically by the formula (Ia), as well as other formulas set forth herein. It should be noted that the compositional range described herein for polymers comprising recurring units of the formula (Ia) exceeds those described in TABLE 1. Accordingly, some preferred examples of inherently radiopaque, biocompatible, bioresorbable polymers are those comprising recurring units represented by the formula (Ia), including polymers that further comprise recurring units of the formula (Ib) and/or formula (IIa).

For example, in accordance with one preferred embodiment of the present invention, a medical device is disclosed, comprising an inherently radiopaque, biocompatible, bioresorbable polymer, including homogeneous polymers, copolymers and blends thereof, wherein the polymer comprises one or more recurring units of the formula (IIIa):

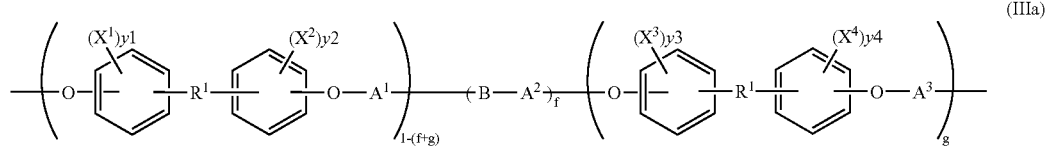

wherein $X^1$, $X^2$, $X^3$, and $X^4$ in formula (IIIa) are each independently I or Br; y1, y2, y3, and y4 in formula (IIIa) are each independently 0, 1, 2, 3 or 4; wherein f and g in formula (IIIa) may range from 0 to 1, with the provision that the sum of f and g in formula (IIIa) is less than 1; wherein $R^1$ and $R^2$ are independently:

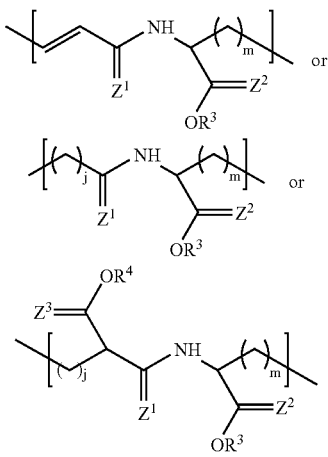

wherein $R^3$ and $R^4$ in formula (IIIa) are each independently H or a non-crystallizable $C_1$ to $C_{30}$ hydrocarbon; wherein j and m in formula (IIIa) are independently integers from 1 to 8; wherein $Z^1$, $Z^2$, and $Z^3$ in formula (IIIa) are each independently O or S; wherein $A^1$ in formula (IIIa) is:

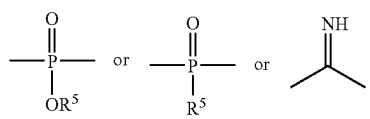

wherein $R^5$ in formula (IIIa) is H or a $C_1$ to $C_{30}$ hydrocarbon; wherein $A^2$ and $A^3$ in formula (IIIa) are each independently selected from the group consisting of

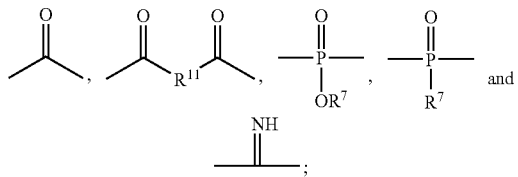

wherein $R^7$ in formula (IIIa) is H or a $C_1$ to $C_{30}$ hydrocarbon and $R^{11}$ in formula (IIIa) is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl; wherein B in formula (IIIa) is —O—((CHR$^6$)$_p$—O)$_q$—; wherein $R^6$ in formula (IIIa) is H or $C_1$ to $C_3$ alkyl; and wherein p and q in formula (IIIa) are each individually an integer in the range of about 1 to about 100.

Preferably, $X^1$, $X^2$, $X^3$, $X^4$, y1, y2, y3 and y4 in formula (IIIa) are selected so that $X^1$, $X^2$, $X^3$, $X^4$ are present in an amount that is effective to render the polymer radiopaque. For example, in an embodiment, the sum of y1, y2, y3, and y4 in formula (IIIa) is at least one. In another embodiment, B in formula (IIIa) is an aliphatic linear or branched diol or a poly(alkylene glycol) unit. It will be recognized that the recurring unit of the formula (IIIa) comprises recurring units of the formulae (Ia), (IIa) and (Ib) as described above. Thus, a polymer that comprises a recurring unit of the formula (IIIa) is an example of the polymer that comprises a recurring unit of the formula (Ia).

Halogenation of the aromatic rings may be accomplished as described in the examples below, and by conventional methods as detailed in U.S. Pat. No. 6,475,477; herein incorporated in its entirety by reference and particularly for the purpose of describing methods of halogenating monomers. Preferred polymers are sufficiently halogenated to render the polymers radiopaque, e.g., y1 and y2 in formula (Ia) may independently=0, 1, 2, 3 or 4. Halogenation of aromatic rings is preferred. In an embodiment, the sum of y1 and y2 is at least one. Various other groups within the polymer may also be halogenated.

Within the broad class of halogenated polymers comprising recurring units represented by formula (Ia), polymers having the $R^1$ and $A^1$ groups indicated in TABLE 2 are preferred:

TABLE 2

| No. | $R^1$ | $A^1$ |
|---|---|---|
| 1 | ![structure with $R^x$, N, $Z^1$, $Z^2$, $OR^3$, m] | —P(=O)(OR$^5$)— |
| 2 | ![structure with $R^x$, N, $Z^1$, $Z^2$, $OR^3$, m] | —P(=O)(R$^5$)— |
| 3 | ![structure with $R^x$, N, $Z^1$, $Z^2$, $OR^3$, m] | =NH |

TABLE 2-continued

| No. | R¹ | A¹ |
|---|---|---|
| 4 | ![structure] | $-\overset{O}{\underset{OR^5}{P}}-$ |
| 5 | ![structure] | $-\overset{O}{\underset{R^5}{P}}-$ |
| 6 | ![structure] | $\overset{NH}{\|\|}$ |
| 7 | ![structure] | $-\overset{O}{\underset{OR^5}{P}}-$ |
| 8 | ![structure] | $-\overset{O}{\underset{R^5}{P}}-$ |
| 9 | ![structure] | $\overset{NH}{\|\|}$ |

According to one aspect of the present invention, a halogen-substituted polymer is provided containing one or more recurring units described by formula (Ia). The composition of the halogenated monomers disclosed herein is also included in accordance with preferred embodiments of the present invention. In certain embodiments, polymers comprising a recurring unit of the formula (Ia) do not contain crystallizable groups, e.g., do not contain crystallizable side chains. For example, in certain embodiments described above, $Q^1$, $Q^2$ and $Q^3$ in the formula for $R^1$ in formula (Ia) are each independently H or a non-crystallizable group comprising from about 1 to about 30 carbons. In other embodiments described above, $R^3$, $R^4$, $R^8$ and/or $R^9$ in formula (Ia) are each independently H or a non-crystallizable $C_1$ to $C_{30}$ hydrocarbon. The crystallization of side chains may be minimized or prevented by controlling the length of the side chain, the type of the side chain and the spacing between side chains. As the spacing between side chains increases, the tendency for the side chains to be crystallizable tends to decrease. Likewise, as the flexibility of the side chains increases, the tendency for the side chains to be crystallizable tends to decrease. Similarly, as the length of the side chains decrease, the tendency for the side chains to be crystallizable also tends to decrease. Thus, certain embodiments of polymers comprising a recurring unit of the formula (Ia) do not include the side chain crystallizable polymers.

Monomer and Polymer Syntheses: The polymers described herein (including, e.g, polymers comprising a recurring unit of the formula (Ia)) may be synthesized by various conventional reactions known in the art. For example, Synthetic Schemes 1-3 illustrate the preparation of halogenated phenolic monomers useful for the making polymers of the formula (Ia). Synthetic Schemes below illustrate reaction schemes to form a polymer comprising a recurring unit of formula (Ia) before N-substitution, e.g. alkylation or arylation, of the amide nitrogen. One of ordinary skill in the art, guided by the disclosure herein, would understand that these synthetic schemes may be readily adapted to operate after the nitrogen atom of the amide group was substituted, as shown below in Synthetic Schemes 8-10.

Synthetic Scheme 1

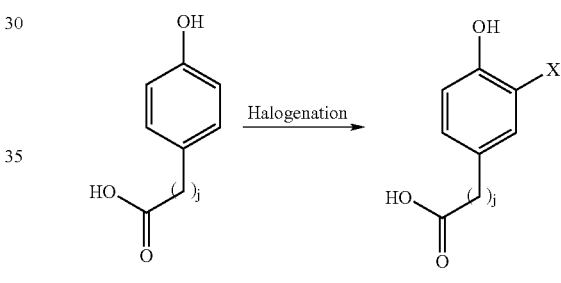

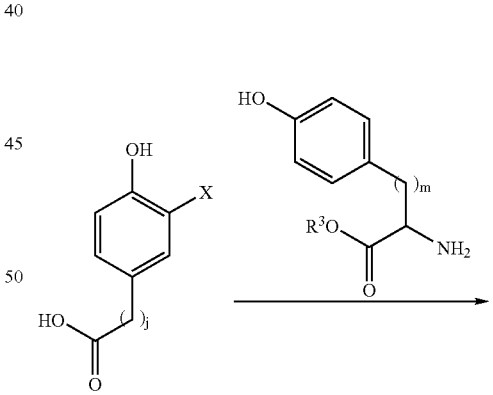

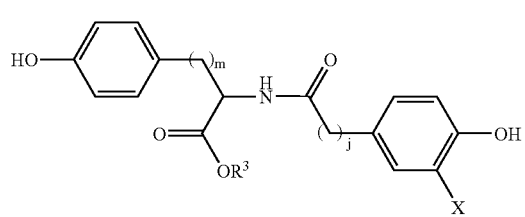

Synthetic Scheme 2

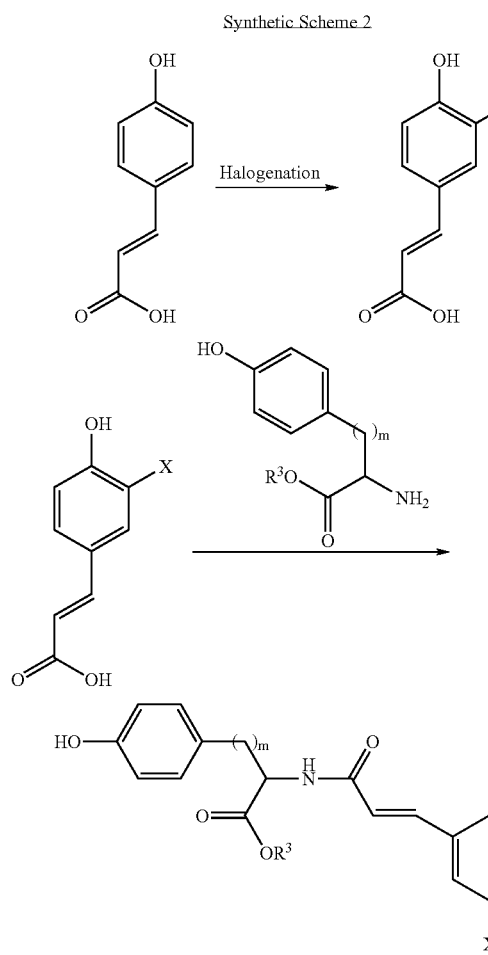

Synthetic Scheme 3

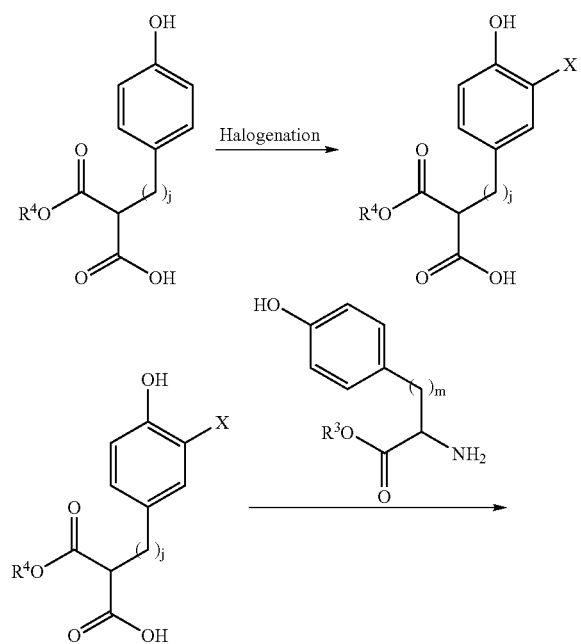

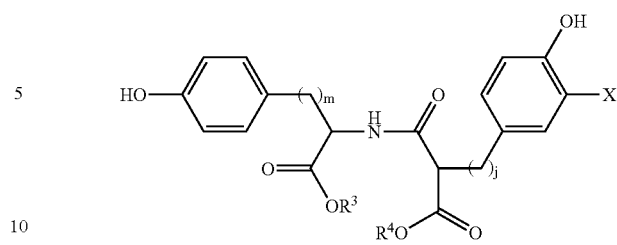

In Synthetic Schemes 1-3 above, X may be a halogen, such as iodo, bromo, chloro, or fluoro. Preferably, the halogen is iodo or bromo. Halogenation may be performed by conventional reactions known in the art. For instance, iodination may be performed on aryl rings by treatment with KI, ICl, IF, benzyltrimethylammonium dichloroiodate, or $I_2$ in the presence of copper salts. Likewise, bromination may be performed on aryl rings by treatment with bromine in the presence of a catalyst, such as iron. Other brominating reagents include HOBr and bromo amides. The coupling of the acid and the amine illustrated in Synthetic Schemes 1-3 may also be performed by conventional reactions in known in the art. Standard coupling reagents, including EDCI, HBTU, HOBt, and the like, may be used for activation of the reactants.

The resulting halogenated phenolic monomers may then be polymerized to form various linkages e.g., polymers having phosphate linkages, such as poly(phosphates) and poly(phosphonates). The respective structures of these classes of polymers, each having a different side chain connected to the phosphorus atom, are as follows:

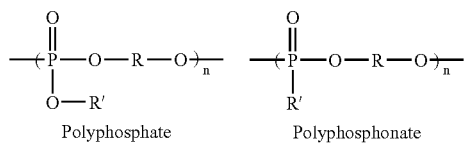

Polyphosphate      Polyphosphonate

The versatility of these polymers may come from the versatility of the phosphorus atom, which is known for a multiplicity of reactions. Its bonding may involve the 3p orbitals or various 3s-3p hybrids; spd hybrids are also possible because of the accessible of orbitals. Thus, the physico-chemical properties of the poly(phosphoesters) may be readily changed by varying either the R or R' group. The biodegradability of the polymer is due primarily to the physiologically labile phosphoester bond in the backbone of the polymer. By manipulating the backbone or the sidechain, a wide range of biodegradation rates are attainable.

Synthetic Schemes 4-5 below illustrate the syntheses of poly(phosphonates) and poly(phosphates), respectively.

Synthetic Scheme 4

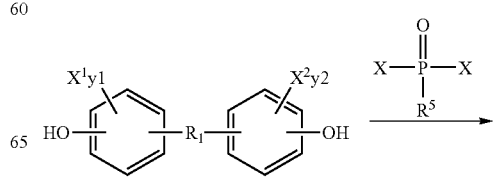

-continued

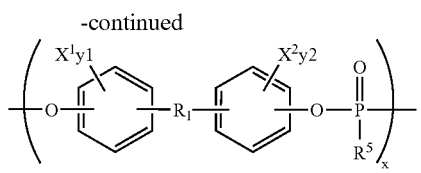

Synthetic Scheme 5

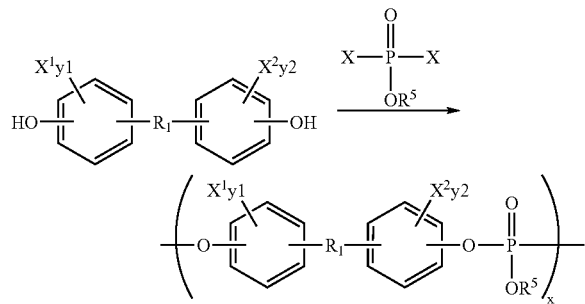

Poly(phosphates) may be prepared by a dehydrochlorination between a phosphodichloridate and a diol according to the following scheme:

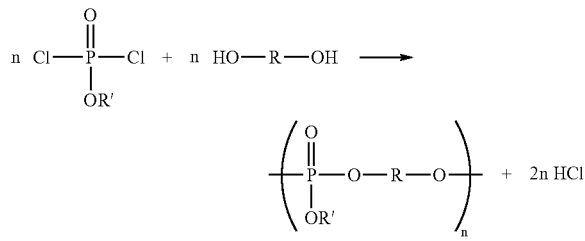

Poly(phosphonates) may be prepared by a similar condensation between appropriately substituted dichlorides and diols.

Poly(phosphites) may be prepared from glycols in a two-step condensation reaction. A 20% molar excess of a dimethylphosphite is preferably used to react with the glycol, followed by the removal of the methoxyphosphonyl end groups in the oligomers by high temperature. An advantage of melt polycondensation is that it avoids the use of solvents and large amounts of other additives, thus making purification more straightforward. It may also provide polymers of reasonably high molecular weight. Polymerization may also be carried out in solution. A chlorinated organic solvent may be used, such as chloroform, dichloromethane, or dichloroethane. To achieve high molecular weights, the solution polymerization is preferably run in the presence of equimolar amounts of the reactants and, more preferably, a stoichiometric amount of an acid acceptor or a Lewis acid-type catalyst. Useful acid acceptors include a tertiary amines such as pyridine or triethylamine. Examples of useful Lewis acid-type catalysts include magnesium chloride and calcium chloride. The product may be isolated from the solution by precipitation in a non-solvent and purified to remove the hydrochloride salt by conventional techniques known to those of ordinary skill in the art, such as by washing with an aqueous acidic solution, e.g., dilute HCl.

Halogenated phenolic monomers may also be polymerized to form polyiminocarbonates as illustrated in Synthetic Scheme 6. Polyiminocarbonates are structurally related to polycarbonates. The polyiminocarbonates have imino groups in the places normally occupied by carbonyl oxygen in the polycarbonates. Thus, the polyiminocarbonates have linkages according to the formula:

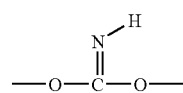

Inclusion of iminocarbonate linkages may impart a significant degree of hydrolytic instability to the polymer. The polyiminocarbonates have desirable mechanical properties akin to those of the corresponding polycarbonates.

Synthetic Scheme 6

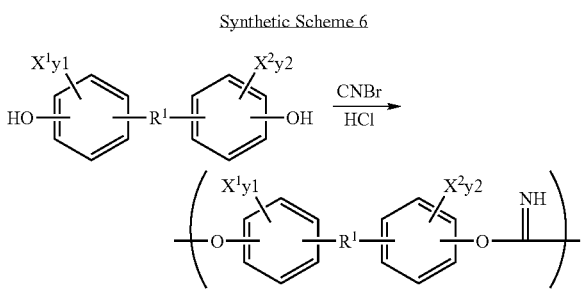

Solution polymerization processes may be used for making polyiminocarbonates. For example, a solution polymerization process may include the steps of contacting a diphenol with a dicyanate in solution in an essentially pure solvent in the presence of a catalyst selected from the group consisting of metal hydroxides, metal hydrides and metal alkoxides and recovering the resulting polyiminocarbonate. The solvent is preferably selected from the group consisting of acetone and tetrahydrofuran ("THF"). Most preferably, the solvent is freshly distilled THF. The catalyst is preferably an alkali metal hydroxide or alkoxide, such as sodium hydroxide or potassium tertbutoxide.

Solvent purity, catalyst selection, and solvent selection may significantly affect the results obtained in the solution polymerization reaction. Thus, even nominally pure reagent-grade or analytical-grade solvents, and particularly THF, may contain residual water, stabilizers such as butylated hydroxy toluene and peroxides. These contaminants, even in minor amounts, may interfere with the solution polymerization reaction. Among the broad class of catalysts suggested for solution polymerization synthesis of polyiminocarbonates, the metal hydroxides, metal alkoxides and metal hydrides, and particularly the alkali metal hydroxides and alkoxides, provide markedly superior results. THF and acetone are preferred solvents.

Interfacial polymerization processes may also be used for production of polyiminocarbonates. For instance, an interfacial polymerization process may include the steps of admixing an aqueous solution of the halogenated phenolic monomer and a basic catalyst with a solution of cyanogen bromide in a water-immiscible organic solvent by progressively adding the aqueous solution to the solution of cyanogen bromide in organic solvent while mixing, and recovering the resulting polyiminocarbonate. The order of addition may be significant, and the rate of addition may also be significant.

The reactions in the above synthetic schemes may be carried through with the non-halogenated versions. Subsequently, halogenation of the polymer may be carried out. Halogenation may be performed by conventional reactions in known in the art. For instance, iodination may be performed on aryl rings by treatment with KI, ICl, IF, benzyltrimethylammonium dichloroiodate, or $I_2$ in the presence of copper salts. For instance, bromination may be performed on aryl rings by treatment with bromine in the presence of a catalyst, such as iron. Other brominating reagents include HOBr and bromo amides. Halogenation of the polymer may be nonselective, which is within the scope of the embodiments.

Starting materials described herein are available commercially, are known, or may be prepared by methods known in the art. Additionally, starting materials not described herein are available commercially, are known, or may be prepared by methods known in the art.

Starting materials may have the appropriate substituents to ultimately give desired products with the corresponding substituents. Alternatively, substituents may be added at any point of synthesis to ultimately give desired products with the corresponding substituents.

The synthetic schemes show methods that may be used to prepare the compounds of preferred embodiments. One skilled in the art will appreciate that a number of different synthetic reaction schemes may be used to synthesize the compounds of preferred embodiments. Further, one skilled in the art will understand that a number of different solvents, coupling agents and reaction conditions may be used in the syntheses reactions to yield comparable results.

One skilled in the art will appreciate variations in the sequence and, further, will recognize variations in the appropriate reaction conditions from the analogous reactions shown or otherwise known which may be appropriately used in the processes above to make the compounds of preferred embodiments.

In the processes described herein for the preparation of the compounds of preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1999.

The products of the reactions described herein are isolated by conventional means such as extraction, distillation, chromatography, and the like.

The salts of the compounds of synthetic schemes described above are prepared by reacting the appropriate base or acid with a stoichiometric equivalent of the compounds of synthetic schemes described above.

Provided herein is a method for making a polymer that comprises a recurring unit of the formula (I). In an embodiment, the method of making the polymer comprises attaching an N-substituent during the synthesis of a corresponding monomer. In an embodiment, the method of making the polymer comprises attaching an N-substituent during polymerization of a corresponding monomer. In an embodiment, the method of making the polymer comprises attaching an N-substituent after polymerization of a corresponding monomer. Methods of making a polymer comprising a recurring unit of the formula (Ia) are further discussed in detail below.

An embodiment provides a polymer that comprises a recurring unit of the formula (XI):

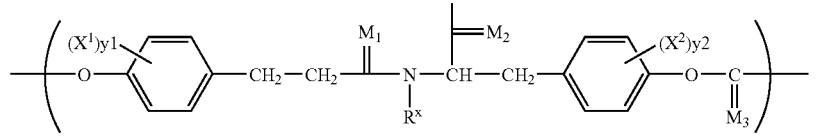

wherein $X^1$ and $X^2$ in formula (XI) are each independently selected from the group consisting of Br and I; $y^1$ and $y^2$ in formula (XI) are each independently zero or an integer in the range of 1 to 4; $M_1$, $M_2$, and $M_3$ in formula (XI) are each independently selected from O or S; $Q_2$ in formula (XI) is selected from O or $NR^y$; $R^x$ in formula (XI) is optionally substituted branched or unbranched $C_1$-$C_{30}$ alkyl or optionally substituted $C_6$-$C_{30}$ aryl; $R^y$ in formula (XI) is selected from hydrogen, optionally substituted branched, or unbranched $C_1$-$C_{30}$ alkyl and optionally substituted $C_6$-$C_{30}$ aryl; and $BA_2$ in formula (XI) is an optionally substituted branched or unbranched $C_1$-$C_{20}$ alkyl or aryl, or comprises a bioactive moiety selected from the group consisting of polyethylene glycol (PEG), poly(propylene glycol) (PPG), poly (tetramethylene glycol), dihydroxy polyvinylpyrrolidone (PVP), dihydroxy poly(styrene sulfonate) (HPSS), poly(2-hydroxyethyl methacrylates) (PHEMA), poly(3-hydroxypropyl methacrylates), poly(3-hydroxypropyl methacrylamide) (PHPMA), poly(alkoxy methacrylates), poly(alkoxy acrylates), polyarginine peptides (PAP), phosphoryl choline (PC), dextran, dextrin, sulfonated dextran, dermatan sulfate, heparin (HEP), chondroitan sulfate, glycosaminoglycans, chitosan, sodium hyaluronate, and hyaluronic acid (HA).

The methods of halogenation described herein can be used to halogenate the polymer comprising a recurring unit of formula (XI). In an embodiment, $R^x$ in formula (XI) is a branched or unbranched $C_1$-$C_6$ alkyl. In an embodiment, $R^x$ in formula (XI) is methyl.

In an embodiment, $M_1$, $M_2$, and $M_3$ in formula (XI) are each independently selected from O or NH.

A polymer comprising a recurring unit of formula (XI) can be copolymerized with any number of other recurring units. In an embodiment, the polymer comprising a recurring unit of formula (XI) further comprises a recurring unit of the formula (XII):

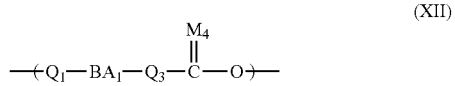

wherein $M_4$ in formula (XII) is O, NH, or S; $Q_1$ and $Q_3$ in formula (XII) are each independently selected from O or $NR^y$; $R^y$ in formula (XII) is selected from hydrogen, optionally substituted branched, or unbranched $C_1$-$C_{30}$ alkyl and optionally substituted $C_6$-$C_{30}$ aryl; and $BA_1$ in formula (XII) is an optionally substituted branched or unbranched $C_1$-$C_{20}$ alkyl or aryl, or comprises a bioactive moiety selected from the group consisting of polyethylene glycol (PEG), poly(propylene glycol) (PPG), poly(tetramethylene glycol), dihydroxy polyvinylpyrrolidone (PVP), dihydroxy poly(styrene sulfonate) (HPSS), poly(2-hydroxyethyl methacrylates) (PHEMA), poly(3-hydroxypropyl methacrylates), poly(3-hydroxypropyl methacrylamide) (PHPMA), poly(alkoxy methacrylates), poly(alkoxy acrylates), polyarginine peptides (PAP), phosphoryl choline (PC), dextran, dextrin, sulfonated dextran, dermatan sulfate, heparin (HEP), chondroitan sulfate, glycosaminoglycans, chitosan, sodium hyaluronate, and hyaluronic acid (HA).

In an embodiment, the polymer comprising a recurring unit of formula (XI) further comprises a recurring unit of the formula (XIII):

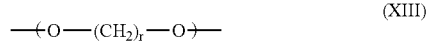

(XIII)

wherein r in formula (XIII) is an integer in the range of from about 1 to about 12.

In an embodiment, the recurring unit of formula (XIII) comprises at least one diol. Diols are organic molecules that contain two alcoholic functionalities, have from 2-30 carbon atoms, and can be straight or branched and optionally substituted. Some embodiments select the diols from those molecules comprising 3-12 carbon atoms. In some embodiments, the selection of diols is carried out to exclude any one of or any combination of straight or branched, optionally substituted, $C_2$-$C_{30}$ diols. In some embodiments, diols can be independently chosen from ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, and 1,12-dodecanediol. In some embodiments, the diol is 1,4-butanediol.

Recurring units of the formula (XIII) can also be terminated with an amine group. Preferred amino terminated moieties are 1,2-ethanediamine, 1,4-butanediamine (putrescine) and 1,5-pentanediamine (cadaverene). However, recurring units of the formula (XIII) can also be any linear or branched diamine with 2 to 16 carbon atoms.

In an embodiment, the polymer comprising a recurring unit of formula (XI) further comprises a recurring unit of the formula (XIV):

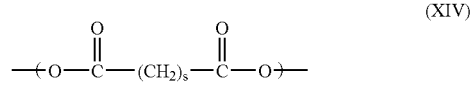

(XIV)

wherein s in formula (XIV) is an integer in the range of from about 2 to about 30.

In an embodiment, the recurring unit of formula (XIV) comprises a diacid. Diacids are organic molecules that contain two carboxylic acid functionalities and have from 2-30 carbon atoms. The diacids can be linear or branched and optionally substituted. In some embodiments, diacids can include any one of or any combination of 2-30 carbon atom, linear or branched and optionally substituted. Also, for purposes of this disclosure, diacids also encompass diacid chlorides and molecules that terminate with an acid functionality at one end and an acid chloride functionality at the other end. In some embodiments, diacids can be independently chosen from oxalic acid, malonic acid, succinic acid, glutaric acid, adipic acid, pimelic acid, suberic acid, azelaic acid, and sebacic acid. In some embodiments, the selection of diacids can be carried out to exclude any one of or any combination of oxalic acid, malonic acid, succinic acid, glutaric acid, adipic acid, pimelic acid, suberic acid, azelaic acid, or sebacic acid. In some embodiments, the diacid can be selected from sebacic acid, adipic acid, and succinic acid.

$M_1$-$M_4$ in formulas (XI) and (XII) can be independently chosen from the following: O or S. In some embodiments, $M_4$ in formula (XII) can further be NH.

$Q_1$-$Q_3$ in formulas (XI) and (XII) can be independently chosen from any number of moieties, including N-, O-, S-, P-, or Se-containing moieties, or alternatively, N- or O-containing moieties, such as NH, NR', or O wherein R' is a $C_1$-$C_{20}$, linear or branched, optionally substituted alkyl or aryl.

$BA_1$ and $BA_2$ in formulas (XI) and (XI) can be independently chosen from R-groups ($C_1$-$C_{20}$, linear or branched, optionally substituted alkyl or aryl), or a bioactive moiety, provided that 100% of both $BA_1$ and $BA_2$ cannot be an R-group. The broadest class of bioactive moieties comprises at least one substituent that provides or causes a biological effect. Exemplary bioactive moieties can be independently chosen from the following: polyethylene glycol (PEG), poly(propylene glycol) (PPG), poly(tetramethylene glycol), dihydroxy polyvinylpyrrolidone (PVP), dihydroxy poly(styrene sulfonate) (HPSS), poly(2-hydroxyethyl methacrylates) (PHEMA), poly(3-hydroxypropyl methacrylates), poly(3-hydroxypropyl methacrylamide) (PHPMA), poly(alkoxy methacrylates), poly(alkoxy acrylates), polyarginine peptides (PAP), such as R7, phosphoryl choline (PC), dextran, dextrin, sulfonated dextran, dermatan sulfate, heparin (HEP), chondroitan sulfate, glycosaminoglycans, chitosan, sodium hyaluronate, or hyaluronic acid (HA).

Some embodiments constrain $BA_2$ to greater than 1 mole % bioactive moiety, alternatively, to less than 99 mole % bioactive moiety. Alternatively, some embodiments constrain $BA_2$ to greater than 10 mole % bioactive moiety and less than 90 mole % bioactive moiety, or greater than 30 mole % bioactive moieties and less than 80 mole % bioactive moieties.

Some embodiments constrain $BA_1$ to greater than 1 mole % bioactive moiety, alternatively, to less than 99 mole % bioactive moiety. Alternatively, some embodiments constrain $BA_1$ to greater than 10 mole % bioactive moiety and less than 90 mole % bioactive moiety; or greater than 30 mole % bioactive moieties and less than 80 mole % bioactive moieties.

The selection of $BA_1$ and $BA_2$ in formulas (XI) and (XII), in some embodiments, can be carried out to exclude any one of or any combination of PEG, PVP, HPSS, PAP, PC, HEP, PPG, poly(tetramethylene glycol), PHEMA, poly(3-hydroxypropyl methacrylates), PHPMA, poly(alkoxy methacrylates), poly(alkoxy acrylates), polyarginine peptides (PAP), such as R7, phosphoryl choline (PC), dextran, dextrin, sulfonated dextran, dermatan sulfate, heparin (HEP), chondroitan sulfate, glycosaminoglycans, chitosan, sodium hyaluronate, or hyaluronic acid (HA). In some embodiments, the selection of $M_1$-$M_4$ formulas (XI) and (XII) can be carried out to exclude any one of or any combination of C, NH or S. In some embodiments, the selection of $Q_1$-$Q_3$ formulas (XI) and (XII) can be carried out to exclude any combination of N-, O-, S-, P-, or Se-containing moieties. Alternatively, in some embodiments the selection of $Q_1$-$Q_3$ formulas (XI) and (XII)

can be carried out to exclude any of or any combination of N- or O-containing moieties, such as NH, NR', or O.

The percentage of recurring units of the formula (XI) in the polymer can vary over a wide range. In an embodiment, the recurring unit of formula (XI) is present in an amount from about 1% to about 99% compared to other recurring units. In an embodiment, the recurring unit of formula (XI) is present in an amount from about 5% to about 95% compared to other recurring units. In an embodiment, the recurring unit of formula (XI) is present in an amount from about 25% to about 75.

The percentage of recurring units of the formula (XII) in the polymer can vary over a wide range. In an embodiment, the recurring unit of formula (XII) is present in an amount from about 1% to about 99% compared to other recurring units. In an embodiment, the recurring unit of formula (XII) is present in an amount from about 5% to about 95% compared to other recurring units. In an embodiment, the recurring unit of formula (XII) is present in an amount from about 25% to about 75.

The percentage of recurring units of the formula (XIII) in the polymer can vary over a wide range. In an embodiment, the recurring unit of formula (XIII) is present in an amount from about 1% to about 99% compared to other recurring units. In an embodiment, the recurring unit of formula (XIII) is present in an amount from about 5% to about 95% compared to other recurring units. In an embodiment, the recurring unit of formula (XIII) is present in an amount from about 25% to about 75.

The percentage of recurring units of the formula (XIV) in the polymer can vary over a wide range. In an embodiment, the recurring unit of formula (XIV) is present in an amount from about 1% to about 99% compared to other recurring units. In an embodiment, the recurring unit of formula (XIV) is present in an amount from about 5% to about 95% compared to other recurring units. In an embodiment, the recurring unit of formula (XIV) is present in an amount from about 25% to about 75.

The amount of bioactive moiety in the polymer can vary over a large range. In an embodiment, the polymer comprises about 1% to about 75%, by weight of $BA_1$. In an embodiment, the polymer comprises about 5% to about 50%, by weight of $BA_1$. In an embodiment, the polymer comprises about 1% to about 75%, by weight of $BA_2$. In an embodiment, the polymer comprises about 5% to about 50%, by weight of $BA_2$.

The mechanical properties of the polymer can be adjusted by (1) varying the molecular weight of the $BA_1$ or $BA_2$, (2) by varying the ratio of tyrosine dipeptide to $BA_1$ or $BA_2$, and (3) by varying the R group when $BA_1$ or $BA_2$ is an R-group. For embodiments where some of $BA_1$ or $BA_2$ is selected to be an R-group, ethyl would be an especially suitable R-group because it cleaves to give ethanol, and such derivatives have been shown to be very biocompatible. K. James, et al Biomaterials, 20, 2203-2212, 1999. K. Hooper, et al. J. Biomed. Mater. Res, 41, 443-454, 1998. In-vivo, these polymers are expected to be amorphous, but with good mechanical properties. The carbonate linkages can be formed using phosgene, which is very hazardous. They can also be formed with triphosgene or diphosgene, which are considerably less toxic, but more expensive. Consequently, phosgene is cost effective for large scale, industrial synthesis, while triphosgene and diphosgene are useful for small lab scale and custom synthesis. Yet, another synthetic route to the polycarbonate is to use diphenyl carbonate instead of phosgene. This process is done in the melt under vacuum with lithium hydroxide catalyst, and is thermodynamically driven by distilling away phenol. It represents a safe way of producing polycarbonates in the lab, but requires higher temperatures and longer reaction times. Useful temperatures can range from 60° C. to 182° C. Useful reaction times can range from 0.5 to 24 hours.

In some embodiments, the polymer comprises poly(ether carbonate) with tyrosine-bioactive moiety. A desaminotyrosyl-tyrosine dipeptide can be combined with the PEG in methylene chloride and phosgene can be added as a solution in toluene. The reaction would be completed in around 9 minutes. In some embodiments, this reaction is carried out for from 1-60 minutes. In an embodiment, the polymer comprises poly(tyrosine carbonate) pendant bioactive moiety groups. In some embodiments, the polymer comprises poly(ether carbonate) tyrosine-diol copolymer with a bioactive moiety in the backbone. In some embodiments, the polymer comprises poly(ether carbonate) tyrosine-diol copolymer with a pendant bioactive moiety. In some embodiments, the polymer comprises poly(ether ester) tyrosine-bioactive moiety-diacid copolymer. In some embodiments, the polymer comprises poly(imino carbonate) tyrosine-bioactive moiety-copolymer. In some embodiments, the polymer comprises poly(imono tyrosine) with pendant PEG groups.

The bioactive moieties, $BA_1$ and/or $BA_2$, may be selected to be PEG or a PEG derivative pendant. Not all of the bioactive moieties need to be PEG or a PEG derivative. PEGylation of the monomers can be carried out in any number of ways, one of which is illustrated by the Reaction Scheme 7, below.

Reaction Scheme 7

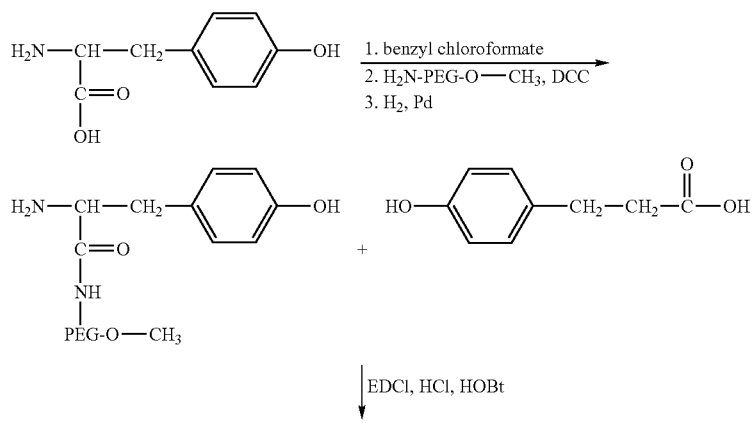

-continued

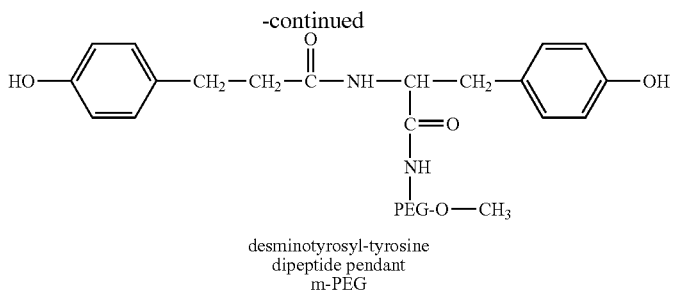

desminotyrosyl-tyrosine
dipeptide pendant
m-PEG

This reaction illustrated above can be manipulated such that any type of bioactive moiety may be added to the monomers and polymers described herein. Those having ordinary skill in the art, guided by the disclosure herein, can manufacture polymers comprising various types of bioactive moieties. In an embodiment, $BA_1$ and/or $BA_2$ comprises hyaluronic acid. In an embodiment, $BA_1$ and/or $BA_2$, comprises polyvinylpyrrolidone.

Furthermore a bioactive moiety, such as PEG or hyaluronic acid, can be provided in the backbone of the polymer. Incorporating PEG or other bioactive moiety into the backbone yields another type of biobeneficial polymer.

In an embodiment, the polymer comprising a recurring unit of the formula (XI) comprises a non-fouling moiety. Non-fouling moieties additionally include polypropylene glycol), PLURONIC™ surfactants, poly(tetramethylene glycol), hydroxy functional poly(vinyl pyrrolidone), dextran, dextrin, sodium hyaluronate, and poly(2-hydroxyethyl methacrylate). A caveat is that the maximum molecular weight of this component should be low enough that this component is small enough to be released through the kidneys. In this respect, 40,000 daltons is the maximum molecular weight for some embodiments. In other embodiments, 20,000 is the maximum molecular weight.

Other bioactive moieties include (polyethylene glycol (PEG), polypropylene glycol), poly(tetramethylene glycol), dihydroxy polyvinylpyrrolidone (PVP), dihydroxy poly(styrene sulfonate) (HPSS), poly(2-hydroxyethyl methacrylate), poly(3-hydroxypropyl methacrylates), poly(3-hydroxypropyl methacrylamide), poly(alkoxy methacrylates), poly (alkoxyacrylates), polyarginine peptides (PAP), such as R7, phosphoryl choline (PC), dextran, dextrin, sulfonated dextran, dermatan sulfate, heparin (HEP), chondroitan sulfate, glycosaminoglycans, chitosan, sodium hyaluronate or hyaluronic acid (HA).

In addition to being useful as non-fouling coatings, these polymers, due to their expected tunable hydration properties, may also be used for the delivery of proteins, peptides, and other biological molecules. These polymers may be coated onto a bare metal stent or they may be coated on top of a drug eluting coating already present on said stent. Conventional therapeutic agents, small hydrophobic drugs for example, may also be added to these bioabsorbable, non-fouling polymers making them bioabsorbable, drug eluting, coatings.

In some embodiments, the polymer comprising a recurring unit of the formula (XI) is mixed with a second polymer. The following polymer families can be the source of second polymer of the mixture: ABS resins; acrylic polymers and copolymers; acrylonitrile-styrene copolymers; alkyd resins; biomolecules; cellulose ethers; celluloses; copoly(ether-esters) (e.g. PEO/PLA); copolymers of vinyl monomers with each other and olefins; cyanoacrylates; epoxy resins; ethylene-a-olefin copolymers; ethylene-methyl methacrylate copolymers; ethylene-vinyl acetate copolymers; poly(amino acids); poly(anhydrides); poly(ester amides); poly(imino carbonates); poly(orthoesters); poly(ester amides); poly(tyrosine arylates); poly(tyrosine derive carbonates); polyalkylene oxalates; polyamides; polyanhydrides; polycarbonates; polyesters; polyethers; polyimides; polyolefins; polyorthoester; polyoxymethylenes; polyphosphazenes; polyphosphoester; polyphosphoester urethane; polyurethanes; polyvinyl aromatics; polyvinyl esters; polyvinyl ethers; polyvinyl ketones; polyvinylidene fluoride; silicones; starches; vinyl halide polymers and copolymers; other biobeneficial polymers; and their combinations. Some invention embodiments are defined such that a second polymer excludes any one or any combination of polymers selected from the families listed above.

The following polymers can be used as second polymers the polymer mixtures: poly(butyl methacrylates); poly (alkoxy acrylates); poly(alkoxy methacrylates); carboxymethyl cellulose; cellophane; cellulose; methyl cellulose; ethyl cellulose; cellulose acetate; hydroxyethyl cellulose; hydroxypropyl cellulose; cellulose acetate butyrate; cellulose butyrate; cellulose nitrate; cellulose propionate; collagen; ethylene vinyl alcohol copolymer; poly(vinyl alcohol); fibrin; fibrinogen; hyaluronic acid; Nylon 66; poly(L-lactide); poly (L-lactic acid), poly(D-lactide), poly(D-lactic acid), poly(D, L-lactic acid), poly(glycolide); poly(L-lactide-coglycolide); poly(D,L-lactide-co-glycolide); poly(caprolactone), poly(L-lactide-co-caprolactone); poly(D,L-lactide-co-caprolactone); polydioxanone; poly(trimethylene carbonate); poly(3-hydroxy valerate); poly(3-hydroxybutyrate); poly(4-hydroxybutyrate); poly(D,L-lactic acid); poly(D,L-lactide); poly(D,L-lactide-co-glycolide); poly(D,L-lactide-co-L-lactide); poly(dioxanone); poly(glycolic acid); poly(glycolic acid-co-trimethylene carbonate); poly(glycolide); poly(hydroxybutyrate); poly(hydroxybutyrate-co-hydroxyvalerate); poly(hydroxybutyrate-co-valerate); poly(hydroxyvalerate); poly(iminocarbonate); poly(lactide-co-glycolide); poly(L-lactic acid); poly(L-lactide); poly(trimethylene carbonate); polyacrylonitrile; polycaprolactam; polycaprolactone; polydioxanone; polyisobutylene; polystyrene; styrene-ethylene/ butylene-styrene triblock copolymers; styrene-isobutylene-styrene triblock copolymers; poly(vinylidene fluoride-co-chlorotrifluoroethylene); poly(vinylidene fluoride-co-hexafluoropropylene); poly(vinyl fluoride); polyvinyl acetate; PEG; POLYACTIVE (a polybutylene terephthalate-PEG group of products and is available from IsoTis Corp. of Holland); and their combinations. Some invention embodiments are defined such that a type-two polymer excludes any one or any combination of the polymers listed above.

The following examples provide non-limiting illustrations as to the various synthesis methods described herein.

Example 1

Synthesis of a Poly(Tyrosine Carbonate) with Pendant Bioactive Moiety Groups Synthesis of carbobenzoxy protected L-tyrosine: To a 1000 ml flask equipped with ice bath and magnetic stirrer is added methanol (250 ml), L-tyrosine (100 gm, 0.552 mole), triethylamine (84.6 ml, 0.607 mole), and benzyl chloroformate (94.2 gm, 0.552 mole). After stirring for 2 hours, the solution is poured into 2 liters of ice water and extracted with three, 500 ml portions of diethylether. The ethereal extracts are combined and washed with one 250 ml portion of 5% acetic acid buffer. After drying the ether phase over magnesium sulfate, the solvent is removed by rotary evaporation and the resulting carbobenzoxy protected tyrosine is dried in vacuum.

Synthesis of tyrosine methoxy-PEG5000 amide: To a 500 ml flask equipped with ice bath, argon inlet and magnetic stirrer is added tetrahydrofuran (200 ml), carbobenzoxy-L-tyrosine (2 gm, 6.35 mmole), methoxy-polyethyleneglycolamine (MW 5000, available from Nektar, Huntsville, Ala.) (31.75 gm, 6.35 mmole), and hydroxyl-benzotriazole (0.946 gm, 7 mmol). After dissolution, dicyclohexylcarbodiimide (1.44 gm, 7 mmol) is added and the reaction stirred for 1 hour at 0.degree. C. and then overnight at ambient temperature. Glacial acetic acid (0.21 gm, 3.5 mmol) is added and the solution is filtered to remove the dicyclohexylurea. After concentrating the solution by rotary evaporation, it is dissolved in 200 ml of methylene chloride and extracted with one 200 ml portion of 0.1 N aqueous HCl, and one 200 ml portion of 0.1N aqueous sodium carbonate. After drying over magnesium sulfate, the solvent is removed by rotary evaporation and the carbobenzoxy tyrosine mPEG amide dried in vacuum.

Hydrogenolysis of carbobenzoxy L-tyrosine mPEG amide: To a 500 ml flask equipped with argon inlet, vacuum line, and hydrogen gas inlet is added palladium (2 gm, 0.019 moles) and vacuum applied. After purging with argon, ethanol (200 ml) is added and hydrogen bubbled through the solution for 30 minutes. Carbobenzoxy tyrosine mPEG amide (20 gm, 3.78 mmol) is added under argon, dissolved, and the solution stirred with a steady bubbling of hydrogen for 12 hours. The palladium is removed by filtration and the ethanol solution added dropwise to 1 liter of ethyl acetate. The tyrosine-mPEG-amide is collected and dried in vacuum.

Synthesis of desaminotyrosyl tyrosine mPEG amide: To a 100 ml flask equipped with magnetic stirrer, argon purge, and ice bath is added tetrahydrofuran (50 ml), desaminotyrosine (0.29 gm, 1.94 mmole), tyrosine-mPEG-amide (10 gm, 1.94 mmol), and hydroxyl-benzotriazole (0.284 gm, 2.1 mmol). After dissolution, dicylohexylcarbodiimide (0.433 gm, 2.1 mmol) is added and the solution stirred at .degree.0 C for one hour and then overnight at ambient temperature. Glacial acetic acid is added (50 mg, 0.83 mmol), the dicyclohexylurea removed by filtration, and the solution concentrated by rotary evaporation. It is dissolved in 50 ml of methylene chloride and extracted with one 50 ml portion of 0.1 N aqueous HCl and one 50 ml portion of 0.1N aqueous sodium carbonate. After drying over magnesium sulfate, the methylene chloride is removed in vacuum yielding desaminotyrosyl tyrosine mPEG amide.

Synthesis of co-poly-{[desaminotyrosyl tyrosine mPEG amide amide]$_{0.0256}$-[desaminotyrosyl tyrosine ethyl ester]$_{0.974}$}: To a 1000 ml round bottom flask equipped with mechanical stirrer and argon inlet is added desaminotyrosyl tyrosine ethyl ester (27.3 gm, 0.071 mole), desaminotyrosyl tyrosine mPEG amide (10 gm, 1.87 mmole), anhydrous methylene chloride (200 ml), and anhydrous pyridine (21.62 gm, 0.273 mole). After dissolution, and at ambient temperature, phosgene (9.01 gm, 0.0911 mole phosgene) as a 20% solution in toluene is added slowly with stirring. After stirring another two hours, tetrahydrofuran (600 ml) is added and the polymer precipitated by slow addition to 5 liters of a 75/25 (w/w) blend of hexane/ethyl acetate. After isolating the polymer, it is redissolved in THF (400 ml) and precipitated in deionized water (4000 ml). After a final dissolution in methylene chloride (800 ml), the solution is filtered through a dry disc apparatus (Horizon Technology, Atkinson, N.H.) with a Teflon™ filter to remove water, the solvent removed by rotary evaporation, and the polymer dried in vacuum. This yields a polymer with a pendant mPEG group of 5000 Dalton molecular weight, and a weight fraction of mPEG in the polymer of 25%.

Example 2

Synthesis of a Poly(Ether Carbonate)Tyrosine-Diol Copolymer with Bioactive Moiety in Backbone To a 1000 ml round bottom flask equipped with mechanical stirrer and argon inlet is added methylene chloride (200 ml), desaminotyrosyl tyrosine ethyl ester (25 gm, 0.07 mol), anhydrous PEG 300 (15.3 gm, 0.051 mol), and pyridine (41.5 gm, 0.525 mol). After dissolution, phosgene (17.31 gm, 0.175 moles) is added dropwise as a 20% solution in toluene at ambient temperature over 60 minutes. Anhydrous 1,4-butanediol (1.71 gm, 0.019 moles) is added, and the solution stirred for another 60 minutes. It is diluted with THF (700 ml) and the polymer precipitated by slow addition to 5 liters of a 75/25 (w/w) blend of hexane/ethyl acetate. After isolation, the polymer is redissolved in THF (400 ml) and precipitated into deionized water (4 liters). After a final dissolution in methylene chloride (800 ml), the solution is filtered through a dry disc apparatus (Horizon Technology, Atkinson, N.H.) with a Teflon™ filter to remove water, the solvent removed by rotary evaporation, and the polymer dried in vacuum. This yields a polymer of with hard blocks, and PEG containing soft blocks, where the PEG 300 moieties are in the polymer backbone. The weight fraction of PEG in the polymer is 33%.

Example 3

Synthesis of a Poly(Desaminotyrosine Tyrosyl Hexyl Ester Succinate)

To a 1000 ml round bottom flask equipped with mechanical stirrer and argon purge is added PEG 600 (25 gm, 0.0417 mol), adipic acid (12.23 gm, 0.0838 mol), desaminotyrosyl tyrosine butyl ester (20.25 gm, 0.0421 mol) and dimethylaminopyridinium p-toluenesulfonate (9.858 gm, 0.0335 mol). Next methylene chloride (500 ml) is added and the reactants dissolved. Diisopropylcarbodiimide (42.3 gm, 0.335 moles) is added and the solution stirred under argon at ambient temperature for 24 hours. The reaction mixture filtered to remove the diisopropylurea and slowly added to diethyl ether (5000 ml) with stirring to precipitate the polymer. The polymer is redissolved in methylene chloride (500 ml) and further purified by slow addition to diethyl ether (5000 ml), after which it is collected and dried in vacuum. This yields a poly(ester amide) polymer containing the PEG 600 moieties in the polymer backbone with a weight fraction of PEG in the polymer of 50%

Provided herein is a method for making a polymer that comprises a recurring unit of the formula (XI). In an embodiment, the method of making the polymer comprises attaching an N-substituent during the synthesis of a corresponding monomer. In an embodiment, the method of making the polymer comprises attaching an N-substituent during polymerization of a corresponding monomer. In an embodiment, the method of making the polymer comprises attaching an N-substituent after polymerization of a corresponding monomer. Methods of making a polymer comprising a recurring unit of the formula (XI) are further discussed in detail below.

Provided herein is a method for making N-alkyl/N-aryl monomer precursors of formula AA-1. Those having ordinary skill in the art, guided by the disclosure herein, can use the N-alkylation/N-arylation steps of forming a monomer precursor described herein to create any N-alkylated/N-arylated monomer that corresponds to the polymers described above.

N-Substituted Monomer Preparation

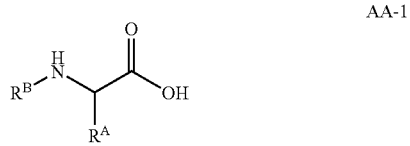

AA-1

The monomer precursors of formula AA-1 are readily prepared via several divergent synthetic routes with the particular route selected relative to the ease of compound preparation, the commercial availability of starting materials, and the like. In some embodiment, the compounds of formula AA-1 can be synthesized as disclosed in U.S. Pat. No. 6,096,782 to Audia et al.; Aurelio et al. (Aurelio et al. "Synthetic Preparation of N-Methyl-α-amino Acids", *Chem. Rev.*, 2004, 5823-5846); Fukuyama et al. (Fukuyama et al. "2,4-Dinitrobenzenesulfonamides: A Simple and Practical Method for the Preparation of a Variety of Secondary Amines and Diamines", *Tet. Lett.*, 1997, 5831-5834); and Ma et al. (Ma et al., "CuI-Catalyzed Coupling Reaction of β-Amino Acids or Esters with Aryl Halides at Temperature Lower Than That Employed in the Normal Ullmann Reaction. Facile Synthesis of SB-214857", *Org. Lett.*, 3 (16), 2001, 2583-2586), the contents of each reference are hereby incorporated by reference in their entirety. For example, the monomer precursors of formula AA-1 can be synthesized as shown in Schemes 8 and 9 below. Other non-limiting methods for synthesizing the precursors of formula AA-1 are shown below. The ubiquitousness of modified amino acids in the literature will lead one of skill in the art to a variety of additional methods to prepare N-modified amino acids.

In an embodiment, in monomer precursor of formula AA-1, variable $R^A$ can be a protected or unprotected side chain of an amino acid. For example, $R^A$ can be the side chain of Alanine, Cysteine, Glycine, Histidine, Isoleucine, Phenylalanine, Serine, Threonine, Tryptophan, Tyrosine, and Valine. In an exemplary embodiment, $R^A$ can be the side chain of Tryptophan where the phenolic hydroxy is protected. For example, the phenolic hydroxy group of Tryptophan can be protected as a methyl ether as shown in the precursor of formula AA-W below.

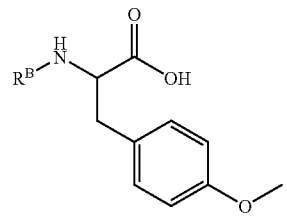

AA-W

In an embodiment, in the monomer precursor of formula AA-1, variable $R^B$ can be an optionally substituted alky or aryl substituent. For example, $R^B$ can be branched or unbranched $C_1$-$C_{30}$ alkyl or optionally substituted $C_6$-$C_{30}$ aryl.

In an embodiment, the monomer precursor for formula AA-1 is synthesized from 8-A:

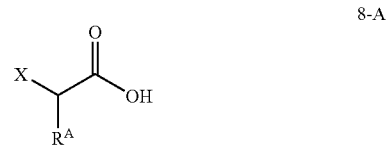

8-A wherein variable X in 8-A is a good leaving group, such as Cl, Br, I, tosylate, mesylate, triflate and the like.

Synthetic Schemes: N-alkyl Monomer Precursors
Scheme 8 Route 1

In an embodiment, a method of introducing the N substituent $R^B$ of monomer precursor AA-1 via a substitution reaction, wherein $R^A$ and $R^B$ is defined as above, and X can be Cl, Br, tosylate, or mesylate as defined as above, can be accomplished as shown in Scheme 8 route 1. For example, in compound 8-A the variable X is a good leaving group and can be substituted with the appropriate aryl or alkyl amine (8-B) to afford monomer precursor AA-1 as described in U.S. Pat. No. 3,598,859, which is hereby incorporated by reference in its entirety. Additionally, suitable ester derivatives of 8-A can be used with this method.

Scheme 8

Route 1

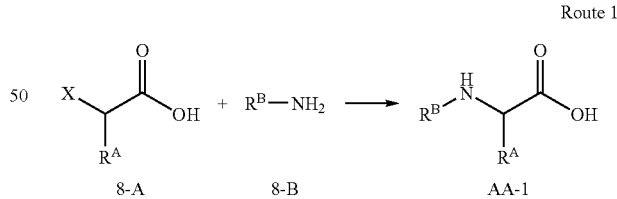

In some embodiments, coupling of 8-A with a primary, aryl, or heteroarylamine of the formula 8-B under appropriate conditions can provide AA-1. This reaction is described by, for example, U.S. Pat. No. 3,598,859. In an embodiment, the reaction proceeds by combining approximately stoichiometric equivalents of 8-A, wherein X is Cl, Br, or I, with 8-B in a suitable inert diluent such as water, dimethylsulfoxide (DMSO), or the like. The reaction employs an excess of a suitable base such as sodium bicarbonate, sodium hydroxide, etc. to scavenge the acid generated by the reaction. The reaction is preferably conducted at from about 25° C. to about 100° C. until reaction completion which typically occurs within 1 to about 24 hours. Upon reaction completion, AA-1 can be isolated by conventional methods, such as, precipitation, chromatography, filtration and the like.

Scheme 8 Route 2

In one embodiment, a method of introducing the N substituent $R^B$ of monomer precursor AA-1 can be accomplished via a reductive amination reaction, as shown in Scheme 8 route 2, wherein $R^A$, $R^B$, and X are define as above. The α-ketoester 8-C can be treated with the appropriate aryl or alkyl amine (8-B) under reductive amination conditions to afford AA-1 as described in U.S. Pat. No. 3,598,859.

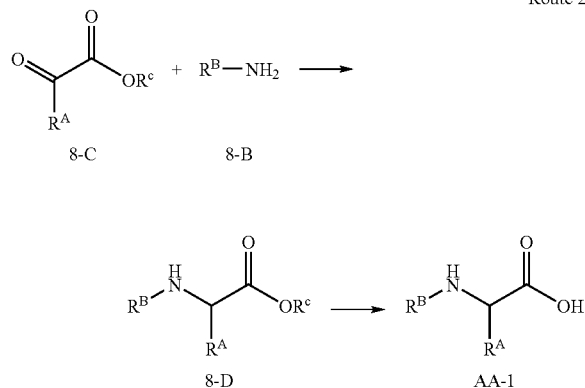

For example, in a exemplary embodiment, approximately stoichiometric amounts of an α-ketoester of formula 8-C and an alkyl or aryl amine of the formula 8-B can be combined in a solvent such as methanol, ethanol and the like and reacted under conditions which provide for imine formation (not shown). The in situ formed imine can be then reduced under conventional conditions by a suitable reducing agent, such as sodium cyanoborohydride, $H_2$/palladium on carbon and the like to form the N-aryl or N-alkyl amino acid ester 8-D. In a typical embodiment, the reducing agent is $H_2$/palladium on carbon which is incorporated into the initial reaction medium which permits imine reduction in situ in a one pot procedure to provide for the N-aryl or N-alkyl amino acid ester 8-D. Subsequent hydrolysis of ester 8-D can afford the monomer precursor AA-1. For example, the ester can be hydrolyzed using wet basic methanol.

Scheme 8 Route 3

In one embodiment, a method of introducing the N substituent $R^B$ of monomer precursor AA-1 can be accomplished via an alkylation reaction of a compound of the formula 8-E and subsequent transformation as shown in Scheme 8 route 3. In some embodiments, $R^A$ and X are define as above, $R^B$ can be branched or unbranched $C_1$-$C_{30}$ alkyl or optionally substituted $C_6$-$C_{30}$ aryl, $R^F$ can be H, $C_1$-$C_6$ alkyl or aryl($CH_2$)—, and $R^E$ can be selected from the group consisting of $CF_3C$(O)—, Cbz- (Carbobenzyloxy), Boc- (tert-Butoxycarbonyl), tosyl- (toluenesulfonyl) or Nosyl- (2-nitrobenzenesulfonyl or 2-nitrobenzenesulfonyl) group, 2,4-dinitrobenzenesulfonyl, and the like. The N-substituted compound of formula 8-E can be treated with an alkylating agent (8-B) under the appropriate conditions to afford 8-G, and the subsequent transformation of 8-G can afford monomer precursor AA-1, as shown below.

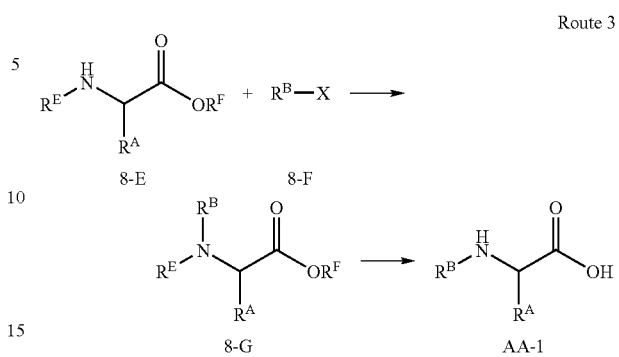

For example, in an exemplary embodiment, Aurelio et al. discloses methods of preparing N-methyl amino acids, these methods can be generally used to prepare additional N-substituted amino acids, such as N-methyl, N-ethyl, N-benzyl and the like.

In an embodiment, treatment of 8-E, wherein $R^E$ is Cbz- or Boc-; $R^F$ is H; and $R^A$ is Me or —$CH_2$Phenyl, with methyl iodide in the presence of $Ag_2O$ in DMF affords 8-E, wherein $R^B$ is methyl and $R^F$ is methyl. Subsequent hydrolysis of the methyl ester and removal of the carbamate type protecting group affords the N-methyl amino acid AA-1. This method can be modified to use ethyl iodide in place of methyl iodide to afford the N-ethyl amino acids of formula AA-1. Additionally, this method can be applied to polymers following the procedure of Das et al. (Das, et al., "N-methylation of N-acyl oligopeptides", Biochem. Biophys. Res. Commun. 1967, 29, 211), the contents of which are hereby incorporated by reference, to afford N-methyl polymers.

In one embodiment, treatment of 8-E, wherein $R^E$ is Cbz- or Boc-; $R^F$ is H; and $R^A$ is Me or —$CH_2$Phenyl with sodium hydride followed by addition of methyl iodide in DMF/THF at 80° C. for 24 h affords 8-E, wherein $R^B$ is methyl and $R^F$ is methyl. Subsequent hydrolysis of the methyl ester with sodium hydroxide in methanol/THF and then removal of the carbamate type protecting group affords the N-methyl amino acid AA-1. This method can be modified to use ethyl iodide in place of methyl iodide to afford the N-ethyl amino acids of formula AA-1. In another embodiment this same procedure can be used to alkylate 8-E wherein $R^F$ is methyl.

In an embodiment, following the procedure of Belagali et al. (Belagali et al. "A Highly Efficient Method of N-Methylation For The Amino-Acid Derivatives", Indian J. Chem. Sect. B, 1995, 34(1), 45), the contents of which are hereby incorporated by reference in their entirety, treatment of 8-E, wherein $R^E$ is Boc-; $R^F$ is H; and $R^A$ is Me or —$CH_2$PhenylOH, with sodium hexamethyldisilazane in THF followed by addition of methyl iodide affords 8-E, wherein $R^B$ is methyl and $R^F$ is methyl. Subsequent hydrolysis of the methyl ester and then removal of the carbamate type protecting group affords the N-methyl amino acid AA-1. This method can be modified to use ethyl iodide in place of methyl iodide to afford the N-ethyl amino acids of formula AA-1. In another embodiment this same procedure can be used to alkylate 8-E wherein $R^F$ is methyl.

In an embodiment, following the procedure of Fukuyama et al., treatment of 8-E, wherein $R^E$ is Nosyl; $R^F$ is Methyl; and $R^A$ is —$CH_2$Phenyl, with $K_2CO_3$ in DMF followed by addition of $R^B$—X, wherein $R^B$—X is propyl iodide, affords 8-E, wherein $R^B$ is propyl and $R^F$ is methyl. Subsequent hydrolysis of the methyl ester and then removal of the carbamate type protecting group can afford the N-propyl amino acid AA-1. This method can be modified to use ethyl iodide in place of propyl iodide to afford the N-ethyl amino acids of formula AA-1.

Scheme 8 Route 4

In a typical embodiment, following the procedure of Fukuyama et al., a DMF solution of the amino acid ester of the formula (8-EA) can be treated with ethyl bromide in the presence of $K_2CO_3$ to afford 8-GA. Subsequently, the 2,4-dinitrobenzenesulfonyl group can be removed and the ester group can be hydrolyzed to afford AA-1A. For example, the 2,4-dinitrobenzenesulfonyl group of can be removed by treatment of 8-GA with thiophenol and $K_2CO_3$ in DMF followed hydrolysis of the methyl ester with NaOH in methanol/THF to afford AA-1A. The N-substituted β-amino acid (AA-1A) can be converted to the N-substituted β-amino ester by methods known to one of skill in the art. For example, the N-substituted β-amino acid can be treated with HCl in a solvent such as ethanol or methanol to afford the corresponding ethyl or methyl N-aryl β-amino esters.

Scheme 8 Route 5

Alternatively, in an exemplary embodiment, a DMF solution of the tert-butyl amino acid ester of the formula (8-EB) can be treated with ethyl bromide in the presence of $K_2CO_3$ to afford 8-GB. Subsequently, the 2,4-dinitrobenzenesulfonyl group can be removed to afford the tert-butyl ester AA-1B. For example, the 2,4-dinitrobenzenesulfonyl group of can be removed by treatment of 8-GB with thiophenol and $K_2CO_3$ in DMF to afford AA-1B.

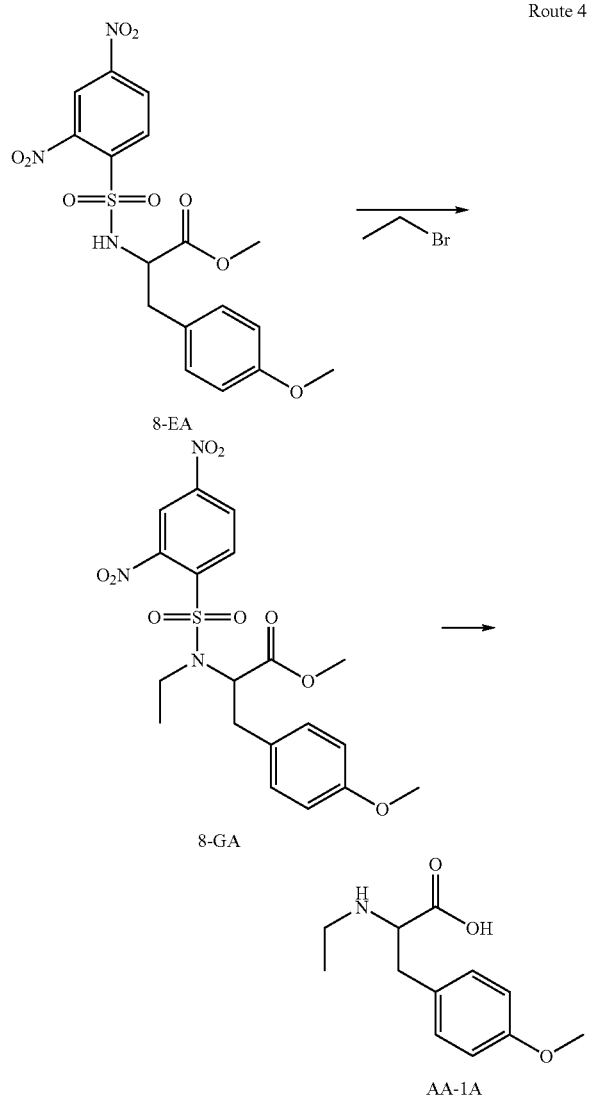

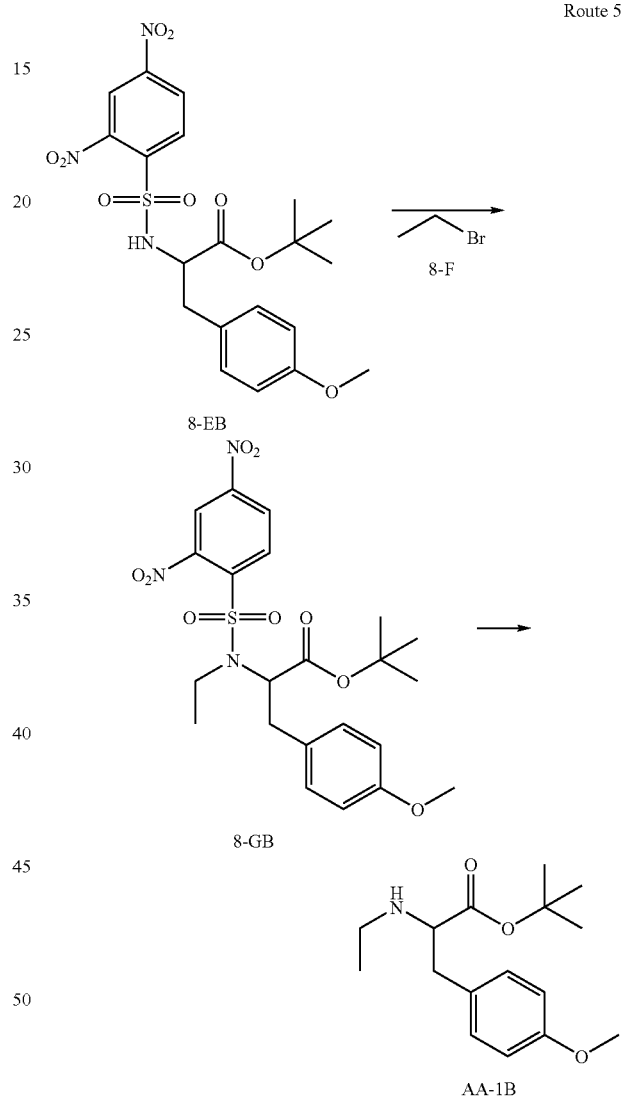

Example from Scheme 8

In a pressure vessel compound 8-EB is dissolved in DMF with $K_2CO_3$ (2 equiv) at room temperature and then treated with ethyl bromide (1.1 equiv.) dropwise via syringe. The pressure vessel is then sealed and the reaction is heated to 60° C., at 30 min intervals the reaction is allowed to cool to room temperature and the progress is checked by TLC (thin layer chromatography) or LC/MS. The reaction is quenched with water and the aqueous layer is extracted. The organic layer is dried over $Na_2SO_4$, filtered and the solvent removed under reduced pressure to afford 8-GB. The intermediate 8-GB is dissolved in DMF in the presence of excess $K_2CO_3$, then thiophenol is added and the mixture is stirred at room temperature until the completion of the reaction as indicated by TLC. The solid is removed by filtration and the solvent is removed under reduced pressure. The crude mixture is then dissolved in wet methanol/THF in the presence of catalytic NaOH, upon completion of the hydrolysis of the ester the solvent is removed under reduced pressure. The residue was dissolved in water, acidified to pH 5, and extracted with ethyl acetate to afford AA-1B.

N-Aryl Monomer Precursors

Scheme 9

In one embodiment, monomer precursor AA-1 can be synthesized, wherein $R^B$ is an aryl group, such as and X is chloride, bromide, or iodide as shown in Scheme 9. For example, the monomer precursor of formula AA-1 can be synthesized by an Ullmann reaction, such as the procedure of Ma et al.

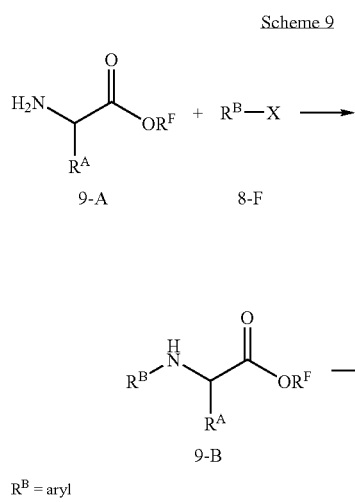

In an exemplary embodiment, the amino ester 9-A can be converted to 9-B, as shown in Scheme 9. For example in the presence of phenyl iodide, CuI and $K_2CO_3$ in DMF at 100° C. In one embodiment, the amino ester 9-C can be treated with phenyl iodide (8-F), CuI and $K_2CO_3$ in DMF at 100° C. to afford 9-D, as shown in Scheme 9-A. The N-aryl β-amino acid (9-D) can be converted to the N-aryl β-amino ester by methods known to one of skill in the art. For example, the N-aryl β-amino acid can be treated with HCl in a solvent such as ethanol or methanol to afford the corresponding ethyl or methyl N-aryl β-amino esters.

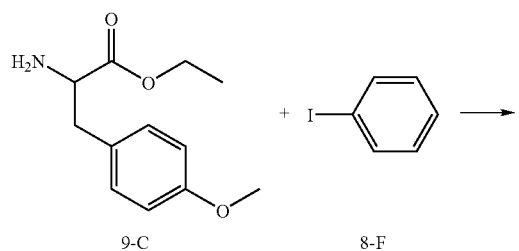

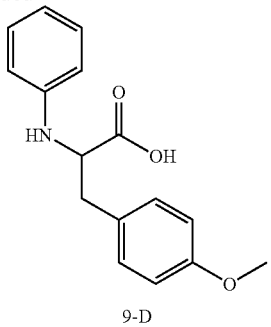

Example from Scheme 9

To a solution of phenyl iodide (1 mmol) and β-amino ester (9-C) (1 mmol) in DMF (5 mL) is added potassium carbonate (2.5 mmol), 0.1 mL of water, and CuI (0.1 mmol) under nitrogen. After the mixture is stirred at 100° C. for 48 h under nitrogen atmosphere, the cooled solution is concentrated in vacuo. The residue is dissolved in water, acidified to pH 5, and extracted with ethyl acetate. The combined organic layers are concentrated and purified by chromatography to afford the corresponding N-aryl β-amino acid (9-D).

The N-aryl β-amino acid (9-D) can be converted to the N-aryl β-amino acid by methods known to one of skill in the art. For example, the N-aryl β-amino acid can be treated with HCl in a solvent such as ethanol or methanol to afford the corresponding ethyl or methyl N-aryl β-amino esters.

N-Substitution During and after Polymerization

It will be appreciated by one of skill in the art that the N-alkylation reactions and N-arylation reactions as exemplified in Scheme 8 and Scheme 9 can also be performed during and after polymerization.

Scheme 10: Thioamide Synthesis

In an embodiment, a recurring unit described herein comprises a thioamide group. The thioamide monomers can be prepared using a method described by A. Kjaer (acta Chemica Scandinavica, 1952, 6, 1374-83), which is hereby incorporated by reference in its entirety. An amide group in the monomers or polymers can also be converted to a thioamide group using the fluorous analog of the Lawesson's reagent ($f_6LR$) whose structure appears below (Kaleta, Z., Makowski, B. T. Sobs, T. and Dembinski, R. Org. Lett. 2006, 8(8), 1625-1628, the contents of which are hereby incorporated by reference in its entirety). The second method is preferable, since it allows the formation of the monomer and/or polymer first then allows the conversion of the amide group to the thioamide group.

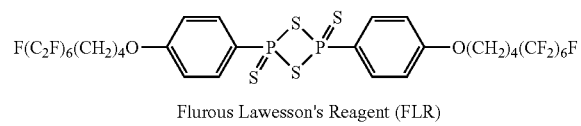

Flurous Lawesson's Reagent (FLR)

Treatment of an amide with this reagent in 1:1 molar ratio in THF gives the corresponding thioamide in >88% yield after purification by chromatography or other means.

For the conversion of the tyrosine derived amide monomers to the corresponding thioamides, the phenolic groups of the monomers are first protected by converting them to the diacetyl esters as shown for $I_2DTE$ by treating with $Ac_2O$/pyridine. The O-protected $I_2DTE$ is then reacted with $f_6LR$ followed by base hydrolysis to the thioamide-$I_2DTE$ as shown in the scheme. The transformation can also be carried out on the polymer using similar procedure.

Scheme 10: Conversion of the amide group in the monomer to the thiomide group

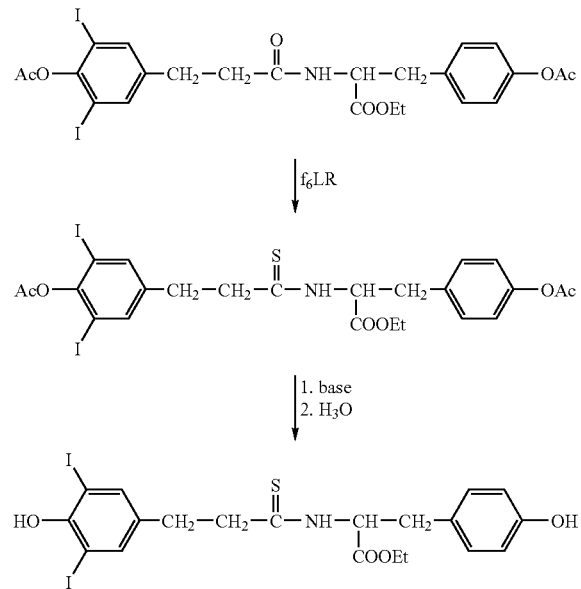

Example from Scheme 10

In a Schlenck tube are placed diacetyl-I$_2$DTE (693 mg, 1.0 mmol), f$_6$LR (1.13 g, 1.0 mmol), and 20 mL of THF. The Schlenck tube is heated in an oil bath 55° C. for 4 hours. To the reaction mixture is then added 10 g of alumina and the solvent was removed by evaporation. The crude product is purified by short column packed with fluorous reverse phase silica. The product is then subjected to hydrolysis with dilute sodium hydroxide followed by acidification to give the I$_2$DTE-thioamide.

N-Substituted Polymerization Precursors

In some embodiments, N-substituted monomer subunits can be synthesized from the above exemplified N-substituted amino acids and amino esters. For example, the polymerization precursor (PP-I) of formula I:

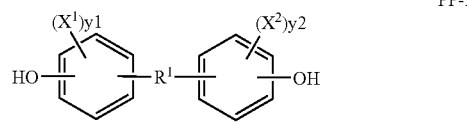

wherein $X^1$ and $X^2$ are defined as in formula (I) and are each independently selected from the group consisting of Br and I; $y^1$ and $y^2$ are defined as in formula (I) are each independently zero or an integer in the range of 1 to 4
wherein $R^1$ is:

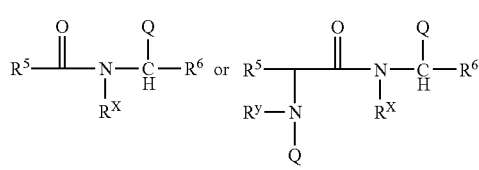

wherein $R^X$ is $R^B$ as defined for formula AA-1;
wherein Q is an ester; and
wherein $R^5$ and $R^6$ are defined as in formula (I) can be synthesized from the monomer precursor of formula AA-1. In an exemplary embodiment, the polymerization precursor (PP-IA):

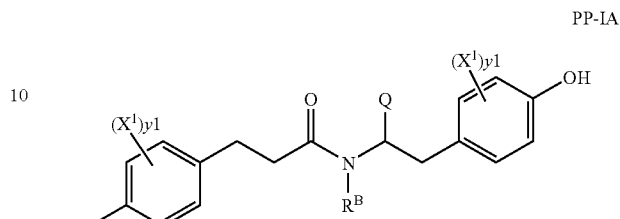

can be synthesized from the monomer precursor of formula AA-1. In a typical embodiment, as shown in Scheme 10, the polymerization precursor 10-C can be synthesized from AA-1B. Iodination of 3-(4-hydroxyphenyl) propionic acid (10-A) affords 3-(4-hydroxy-3,5-diiodophenyl)propanoic acid. Subsequent coupling of 10-B with AA-1B followed by removal of the phenol protecting group afford the polymerization precursor 10-C. For example, treatment of 3-(4-hydroxyphenyl) propionic acid (10-A) with chloroiodide affords 3-(4-hydroxy-3,5-diiodophenyl)propanoic acid (10-B). Coupling of 10-B with AA-1B using N-(3-Dimethylaminopropyl)-N'-ethylcarbodiimide hydrochloride (EDCI) followed by deprotection of the phenol protecting group can afford the polymerization precursor 10-C. The removal of the methyl protecting group can be accomplished using boron tribromide (BBr$_3$) in methylene chloride (DCM). The polymerization precursor 10-C can be converted into polymeric form following the methods disclosed in synthetic scheme 1-6. Additional monomer subunits can be synthesized from monomer precursors of formula AA-1 following the method of Scheme 10 with appropriate modifications readily apparent to one of skill in the art.

Scheme 10

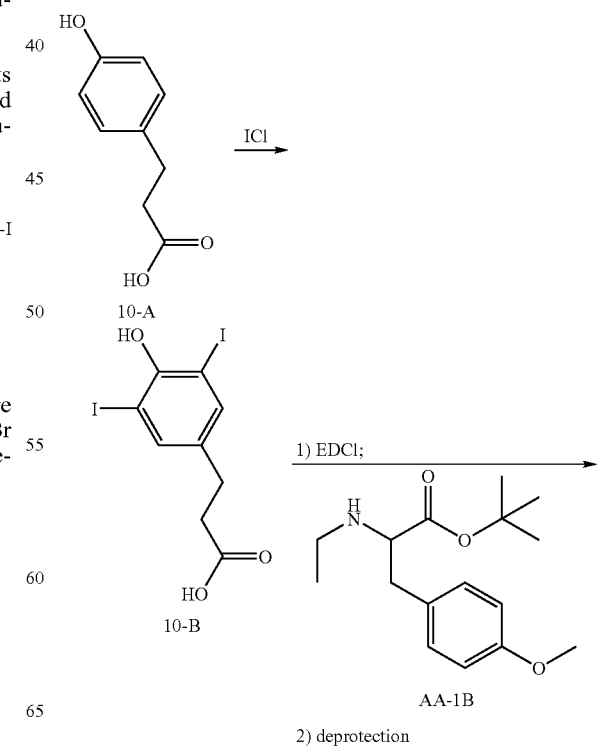

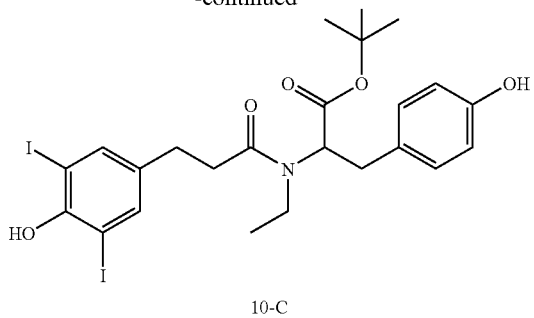

10-C

It will be appreciated by one of skill in the art that the N-arylation reactions and N-alkylation reactions as exemplified in Scheme 8 and Scheme 9 can be performed during and after polymerization.

In these synthetic methods, the starting materials can contain a chiral center (e.g., alanine) and, when a racemic starting material is employed, the resulting product is a mixture of diastereomers or R,S enantiomers. Alternatively, a chiral isomer of the starting material can be employed and, if the reaction protocol employed does not racemize this starting material, a chiral product is obtained. Such reaction protocols can involve inversion of the chiral center during synthesis.

Accordingly, unless otherwise indicated, the products of this invention are a mixture of diastereomers (if two or more chiral centers are present) or R,S enantiomers (if only one chiral center is present). Preferably, however, when a chiral product is desired, the chiral product corresponds to the L-amino acid derivative. Alternatively, chiral products can be obtained via purification techniques which separates diastereomers or enantiomers from a R,S mixture to provide for one or the other stereoisomer. Such techniques are well known in the art.

The polymers described herein (e.g., polymers comprising a recurring unit of the formula (I), polymers comprising a recurring unit of the formula (Ia), and/or polymers comprising a recurring unit of the formula (XI)) may be used for various applications such as in medical devices. For example, various preferred embodiments provide medical devices that comprise a polymer of the formula (I). Additionally, various preferred embodiments provide medical devices that comprise a polymer of the formula (Ia). Furthermore, various preferred embodiments provide medical devices that comprise a polymer of the formula (XI).

The medical device may comprise the polymer in various ways. For example, the medical device may be constructed in whole or in part of the polymer, coated with the polymer, sealed within the polymer, and/or the device may contain the polymer. Non-limiting examples of medical devices that may comprise a polymer comprising at least one recurring unit of the formula (I), (Ia), and/or (XI) include for vascular applications a stent, stent graft, annuloplasty ring, vascular graft, suture, vascular cuff, septal defect repair device, heart valve, heart valve component, heart valve repair device, closure device, inducer of vasculature and connective tissue proliferation, catheter (e.g., balloon catheter configured to deliver a stent) and/or tissue engineered implant.

Various medical device embodiments are described in greater detail below. It will be appreciated that a medical device may consist solely of a polymeric material that consists solely of the polymer described herein. For example, in an embodiment, a medical device is configured to be deliverable (e.g., by injection, catheter, physical insertion, pouring, a heated rod, spraying and/or squirting) to a body cavity of a mammal. Such a device may be, for example, an embolotherapy product formed primarily of a polymeric material that comprises the polymer described herein. Thus, while certain descriptions below may be directed to medical devices, it will be understood that such descriptions also apply to polymeric materials and to the polymers described herein, unless the context indicates otherwise. Likewise, descriptions herein of polymeric materials and of the polymers described herein also apply to medical devices, unless the context indicates otherwise.

In a preferred embodiment, the medical device comprises a stent. The stent may comprise various configurations, e.g., a configuration selected from the group consisting of a sheet stent, a braided stent, a self-expanding stent, a wire stent, a deformable stent, and a slide-and-lock stent.

In a preferred embodiment, the stent comprises at least two substantially non-deforming elements arranged to form a tubular member, the non-deforming elements being slidably interconnected for allowing the tubular member to expand from a collapsed diameter to an expanded diameter. In another variation the tubular member comprises a series of slideably engaged radial elements and at least one locking mechanism which permits one-way sliding of the radial elements from a first collapsed diameter to a second expanded diameter.

Another embodiment provides a system for treating a site within a vessel, comprising a stent and a catheter having a deployment means, wherein said catheter is adapted to deliver the stent to said site and said deployment means is adapted to deploy the stent. Another embodiment provides a method for re-treatment of a body lumen, comprising deploying such a stent along a region within a blood vessel, wherein such a stent resides for a period of time; and deploying at a later time a second stent, along the approximate same region within the blood vessel, such that the blood vessel is re-treated.

A stent on a catheter is commonly collectively referred to as a stent system. Catheters include but are not limited to over-the-wire catheters, coaxial rapid-exchange designs and the Medtronic Zipper Technology that is a relatively new multi-exchange delivery platform. Such catheters may include, for instance, those described in U.S. Pat. Nos. 4,762,129; 5,232,445; 4,748,982; 5,496,346; 5,626,600; 5,040,548; 5,061,273; 5,350,395; 5,451,233 and 5,749,888. Additional examples of suitable catheter designs include those described in U.S. Pat. Nos. 4,762,129; 5,092,877; 5,108,416; 5,197,978; 5,232,445; 5,300,085; 5,445,646; 5,496,275; 5,545,135; 5,545,138; 5,549,556; 5,755,708; 5,769,868; 5,800,393; 5,836,965; 5,989,280; 6,019,785; 6,036,715; 5,242,399; 5,158,548; and 6,007,545. The disclosures of the above-cited patents are incorporated herein by reference in their entirety.

Catheters may be specialized for various purposes such as to produce an ultrasound effect, electric field, magnetic field, light and/or temperature effect. Heating catheters may include for example those described in U.S. Pat. Nos. 5,151,100, 5,230,349; 6,447,508; and 6,562,021 as well as WO 90\14046 A1. Infrared light emitting catheters may include for example those described in U.S. Pat. Nos. 5,910,816 and 5,423,321. The disclosures of the above-cited patents and patent publications are incorporated herein by reference in their entirety.

In another preferred variation, the stent further comprises an amount of a therapeutic agent (for example, a pharmaceutical agent and/or a biologic agent) sufficient to exert a selected therapeutic effect. The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

For devices placed in the vascular system, the amount of the therapeutic agent is preferably sufficient to inhibit restenosis or thrombosis or to affect some other state of the stented tissue, for instance, heal a vulnerable plaque, and/or prevent rupture or stimulate endothelialization. The agent(s) may be selected from the group consisting of antiproliferative agents, anti-inflammatory, anti-matrix metalloproteinase, and lipid lowering, cholesterol modifying, anti-thrombotic and antiplatelet agents, in accordance with preferred embodiments of the present invention. In some preferred embodiments of the stent, the therapeutic agent is contained within the stent as the agent is blended with the polymer or admixed by other means known to those skilled in the art. In other preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent. The therapeutic may be chemically bonded to the polymer or carrier used for delivery of the therapeutic of at least one portion of the stent and/or the therapeutic may be chemically bonded to the polymer that comprises at least one portion of the stent body. In one preferred embodiment, more than one therapeutic agent may be delivered.

A medical device that comprises a polymer described herein may be a medical device in which at least a portion of the polymer is positioned at a surface of the medical device. It has been found that such positioning of the polymer (e.g. an SCC polymer) at a surface of the medical device allows the surface properties of the medical device to be manipulated as a function of temperature, e.g., the SCC polymer at the surface may provide increased biocompatibility and/or function as a temperature-dependent lubricant and/or adhesive, e.g., at an interface with one or more other medical devices and/or medical device components. The polymer may be positioned at the surface of the medical device in various ways. For example, amounts of an SCC polymer may be applied to selected locations on the surface of the medical device; an SCC polymer may be coated onto the surface of a medical device; a film of an SCC polymer may be applied to a medical device; and/or a medical device may be manufactured in such a way that an SCC polymer is formed at a surface. For example, in an embodiment, radiopaque and/or crystallizable groups may be grafted onto the surface of a polymeric medical device, e.g., by reacting radiopaque and/or crystallizable groups with functional groups on the surface and/or by polymerizing radiopaque and/or crystallizable monomers from initiation sites on the surface to thereby form polymeric radiopaque and/or crystallizable groups. Functional groups and initiation sites may be created on the surface of a polymeric medical device in various ways. For example, treatment of a polymer surface with ionizing radiation (e.g., e-beam and/or gamma radiation) and/or plasma in the presence of oxygen may result in the formation of —OH groups on the polymer surface. Such —OH groups may then be reacted with an isocyanate-functionalized radiopaque and/or crystallizable group to thereby attach those groups to the surface by forming urethane linkages. Polymerization of an appropriate monomer such as caprolactone may be initiated from the —OH groups in the presence of a suitable catalyst (such as stannous octoate) to form crystallizable PCL groups that are attached to the polymer surface. As another example, treatment of a polymer surface with ionizing radiation and/or plasma may produce active surface sites capable of initiating the polymerization of photo- and/or radiation-sensitive crystallizable monomers (1-alkenes containing from about 6 to about 30 carbons), thereby grafting a side-chain crystallizable polymer onto the surface of the polymeric medical device. The group attached to the surface may be radiopaque and/or crystallizable. In an embodiment, the polymeric medical device comprises a SCC polymer attached to the surface thereof.

The temperature-dependent properties (e.g., adhesion, lubrication, etc.) of a particular polymer (e.g. an SCC polymer) positioned at a surface of a medical device typically depend on the nature of the surface, the nature of the polymer and the nature of the interactions between them. For example, in some cases, relatively low molecular weight SCC polymers tend to have better adhesive properties at temperatures above the melting point of the SCC polymer, as compared to the adhesive properties of those SCC polymers at temperatures below the melting point. On the other hand, in some cases, relatively high molecular weight SCC polymers tend to have better adhesive properties at temperatures below the melting point than at temperatures above the melting point. Relatively non-polar SCC polymers capable of forming relatively weak intermolecular interactions, such as heavily fluorinated SCC polymers, tend to be better lubricants than relatively polar SCC polymers capable of forming relatively strong intermolecular interactions, depending on the nature of the surface of the medical device. The use of a particular SCC polymer to provide temperature-dependent functionality at a surface of a medical device is preferably determined by routine experimentation, in view of general principles of adhesion known to those skilled in the art as informed by the guidance provided herein.

The viscosity and/or melting point of a medical device that comprises a polymer described herein typically depends on the relative amounts of the polymer and other components, if any, present in the medical device. The viscosity and/or melting point of the medical device (or polymeric material in the medical device) may be controlled by manipulating the amount of the polymer in the medical device and by selecting a polymer that provides the resulting medical device with the desired viscosity and/or melting point. Thus, for example, to provide a polymeric material that has a melting point of 40° C., it may be desirable to select a polymer that has a somewhat higher melting point, e.g., about 45° C., for incorporation into the polymeric material, to compensate for the presence of a second polymer or other component that has a tendency to lower the melting point of the polymer when in admixture with it. In an embodiment, a medical device comprises a polymeric material that has a melting point in the range of about 30° C. to about 80° C.

The polymeric material of the medical device is preferably configured to flow at a temperature above the melting point. The viscosity of the polymeric material at the temperature above the melting point may vary over a broad range, depending on factors such as the intended application. For example, for embolotherapy products, the polymeric material preferably has a viscosity above the melting point that allows the medical device to be delivered to the target vasculature by a convenient technique such as by injection through a syringe and/or by flowing through a catheter. In such cases, the desired viscosity often depends on the diameter of the syringe needle or catheter, e.g., lower viscosities are typically preferred at smaller diameters. On the other hand, if the viscosity is too low, the polymeric material may migrate away from the target vasculature prior to cooling and solidifying. In an embodiment, the polymeric material of the medical device has a viscosity in the range of about 50 cP to about 500 cP at the temperature above the melting point. In another embodiment, the polymeric material has a viscosity in the range of about 500 cP to about 5,000 cP at the temperature above the melting point. In another embodiment, the polymeric material has a viscosity in the range of about 5,000 cP to about 250,000 cP at the temperature above the melting point. In another embodiment, the polymeric material has a viscosity in the range of about 250,000 cP to about 1,000,000 cP at the temperature above the melting point.

In an embodiment, the polymeric material is configured to form a solid mass upon delivery to a body cavity. The solid mass may wholly or partially conform to an interior dimension of the body cavity. For example, the polymeric material may be configured to contain an amount of a polymer (e.g., an SCC polymer) that provides the polymeric material with a melting point of about 40° C. The polymeric material may be further configured to be deliverable to the body cavity, e.g., the polymeric material may be in the form of a rod that may be heated to a molten state to facilitate flow. The molten polymeric material may then be delivered to a body cavity by flowing through a delivery device in the molten state. Upon arrival in the body cavity, the molten polymeric material may at least partially conform to the interior dimension of the body cavity, then cool to form a solid mass. As another example, the polymeric material may be in the form of small particles suspended in a relatively low viscosity biocompatible carrier liquid such as water or saline. The polymeric material may then be caused to flow through a delivery device to the target body cavity. The small particle of polymeric material may be heated prior to delivery, during delivery and/or within the target cavity by, thereby causing the polymeric material to flow and conform to an interior dimension of the body cavity. Upon cooling, the polymeric material may form a solid mass that continues to conform to the interior dimension of the body cavity. It will be understood that polymeric materials of various configurations and formulations before heating may vary in their ability to conform to the body cavity once warmed and may therefore be selected for this reason to tailor the treatment. Further, it will be understood that the polymeric material need not be completely melted to achieve delivery. For example, a polymeric material may be formed into a particular shape, such as a coil, then implanted into the target body cavity while retaining the preformed shape. The polymeric material (e.g., coil) may be heated prior to and/or during implantation for various reasons, e.g., to render the coil more resilient and thus easier to deliver, and/or to enable the coil to better conform to the body cavity into which it is implanted. The polymeric material may also be caused to flow outside the body then be delivered to the body cavity in a flowable state.

An embodiment provides a shape memory polymeric material that comprises a polymer described herein. For example, a polymer (e.g., an SCC polymer) may be configured into a first shape such as a coiled shape by a standard thermoplastic formation process and crosslinked to fix the memory of the first shape. The formed polymer coil may then be heated to melt the polymer, allowing it to be re-configured into a second shape such as a rod shape. The cross-linking limits or prevents thermoplastic flow while the polymer is in the melted state. The polymer while still in the second shape may then be cooled to a temperature at which the polymer recrystallizes. The recrystallization of the polymer limits or prevents the second shape (e.g., the rod shape) from returning to the first shape (e.g., the coil shape). Upon re-heating to a temperature above the melting point of the polymer, the second shape returns to the first shape, e.g., the rod reverts to its memory state of a coil. Crosslinking of the polymer may be carried out in various ways known to those skilled in the art.

An embodiment provides a method of treatment that comprises introducing a medical device as described herein into a body cavity of a mammal in an amount that is effective to at least partially occlude the body cavity. In general, such a method may be used to occlude any type body cavity including, e.g., various body cavities that may commonly be referred to as tubes, tubules, ducts, channels, foramens, vessels, voids, and canals. In a preferred embodiment, the medical device is an embolotherapy product. Preferably, the medical device comprises a polymer comprising at least one recurring unit of the formula (I), (Ia), and/or (XI). In another preferred embodiment, the body cavity comprises vasculature, e.g., an arteriovenous malformation or a blood vessel such as a varicose vein. The medical device may be introduced to the body cavity in a variety of ways, including by injection, by catheter and by surgical implantation. For a particular body cavity, the medical device is preferably selected so that the polymeric material has a melting point that is sufficiently high that the polymer forms a solid mass at the normal temperature of the body cavity, and sufficiently low so that that softened or molten polymeric material may conform to a dimension of the body cavity with little or no thermal damage to the mammal into which it is introduced. Introduction of such a polymeric material into the body cavity thus may comprise heating the polymeric material to a temperature that is higher than the melting point and/or cooling it to a temperature that is lower than the melting point.

Various types of delivery devices may be used to introduce the medical device to the body cavity, e.g., plastic tubes, catheters, fine cannula, tapered cannula and various types of syringes and hypodermic needles which are generally known to and available to those in the medical profession. An embodiment provides a medical apparatus that comprises a polymeric material and a delivery device, where the polymeric material comprises at least one recurring unit of the formula (I), (Ia), and/or (XI), and where the polymeric material and the delivery device are mutually configured to facilitate delivery of the polymeric material to a body cavity by the delivery device. The polymeric material is preferably contained within the delivery device, in an amount that may vary somewhat depending on the particular body cavity to be occluded and the amount and type of occlusion desired. Those skilled in the art will be aware of the size of the cavity being occluded based on the size of the patient, general knowledge of anatomy, and thus use of diagnostic methods such as X-ray and MRI. Those skilled in the art will be able to determine the amount of polymer material to be included within the delivery device. In general, an excess amount of polymeric material should be included in the delivery device in order to provide for a certain margin of error. In an embodiment, the medical apparatus comprises an embolotherapy product and a tube, where the embolotherapy product comprises a polymer as described herein and where the tube is configured to facilitate flow of the embolotherapy product to a body cavity. For example, the tube may comprise a needle, cannula, syringe, and/or catheter, and may be equipped with a heater configured to heat the embolotherapy product to a temperature above its melting point, e.g., to a temperature in the range of about 30° C. to about 80° C. The polymeric material may be included within the delivery device in a solid form or heated separately and provided in the delivery device in a flowable form. In an embodiment, the medical apparatus may be prepackaged with the polymeric material present within the delivery device and may thereafter be heated in order to make the polymeric material flowable. Heating may be applied from an exterior source such as an air, water or oil bath or an electrical heater, in which case both the delivery device and the polymeric material may be heated. Heating can also be applied from an interior source, e.g., using a small electrical resistive element at the end of a catheter through which a thin rod of the solid polymeric material is passed, or using a small laser directed at the tip of a rod of polymeric material emerging from the end of a catheter.

The delivery device may include an extrusion nozzle which is preferably relatively small in diameter such that it will not seriously damage the tissue in the vicinity of the body cavity to be occluded, but sufficiently large such that the polymeric material can be readily extruded from the nozzle. For example, in application that involves the occlusion of a body channel, the size of the nozzle is generally related to the inside diameter of the channel into which it is placed. For example, a 24 gauge needle typically fits within the opening of the punctum which leads to the canaliculus. A 2 mm catheter is typically appropriate for introducing the polymeric material into the fallopian tubes. A ¼ inch cannula is preferred for introducing the polymeric material into the inner cavity of an adult humerus. When delivered in the molten state, the polymeric material is preferably selected to have a viscosity that facilitates passage of the polymeric material through the extrusion nozzle. In general, relatively lower viscosities are preferred for relatively smaller diameter nozzles.

It will be understood that the delivery device may include an extrusion nozzle with one or more delivery ports. The polymeric material may be dispensed through multiple ports serially or simultaneously. This approach may accommodate better packing and/or stabilization of the polymeric material that cools and it may allow for delivery of more polymeric material across a large surface area. That various configurations and formulations may be simultaneously delivered by the use of various delivery ports.

For example, in an embodiment, two or more polymeric materials may be delivered sequentially to a body cavity. In an embolotherapy embodiment, a first polymeric material is delivered to vascular structure. The first polymeric material may have a first configuration, such as a coil. The coil may be preformed, e.g., a shape memory coil as described above that is delivered in a rod shape (forming a coil upon delivery), or may be a coil that is formed during delivery by extruding the polymeric material through a delivery port of the delivery device having an appropriately configured die. The first polymeric material is preferably delivered at a temperature higher than its melting point (e.g., higher than the melting point of a first SCC polymer in the first polymeric material).

A coil may be a relatively open structure that partially occludes the vascular structure, reducing the blood flow without completely stopping it. Although such partial occlusion may be appropriate in some cases, in other cases further occlusion may be desired. Such further occlusion may be accomplished by delivering a second polymeric to the vascular structure in operable proximity to the first polymeric material. The second polymeric material is preferably delivered at a temperature higher than the its melting point (e.g., higher than the melting point of a second SCC polymer in the second polymeric material). The second polymeric material preferably has a lower viscosity than the first polymeric material, such that it may at least partially fill interstices or gaps in the first polymeric material and/or between the first polymeric material and the interior of the vascular structure. Thus, for example, the second polymeric material may have the consistency of a paste at a temperature above its melting point during delivery, allowing it to fill in the spaces of the first polymeric material coil.

One or more additional polymeric materials may be delivered to a location in operable proximity to the first and second polymeric materials. For example, the first and second polymeric materials may only partially occlude the vascular structure, although typically to a greater extend than the first polymer alone. In such a case, it may be desirable to deliver a third polymeric material to provide further occlusion. The third polymeric material is preferably delivered at a temperature higher than its melting point (e.g., higher than the melting point of a third SCC polymer in the third polymeric material). The third polymeric material preferably has a lower viscosity than the first polymeric material, and more preferably lower than the second polymeric material, such that it may at least partially fill interstices or gaps in the polymeric mass formed by the first and second polymeric materials and/or between the mass and the interior of the vascular structure.

Those skilled in the art will appreciate that multiple variations of the embodiments described above may be practiced. For example, a single polymeric material may be delivered in multiple doses or in different forms, e.g., as a coil in a first delivery and as a paste in a second delivery, or as a paste in both the first and second deliveries. Two or more polymeric materials may be delivered simultaneously, e.g., a first polymeric material in a coil shape may be coated or mixed with a second polymeric material in a paste or liquid form to form a composite that comprises both polymers, and the resulting composite may then be delivered to the body cavity. Various body cavities may be the target of the delivery, and/or the order in which the various polymeric materials and forms are delivered may be varied. Delivery of a polymeric material that comprises a polymer described herein may be combined, sequentially or simultaneously, with the delivery of a different material, e.g., a metal embolic coil. Thus, for example, a polymeric material may be delivered to a body cavity, and a metal embolic coil may be delivered to the body cavity in contact with the polymeric material. Various periods of time may pass between deliveries, e.g., a polymeric material coil may be delivered to provide partial occlusion of a body cavity, and a second polymeric material paste may be delivered to a location in operable proximity to the coil minutes, hours, days, weeks, months, or years later.

For embodiments in which the polymeric material is delivered in the molten state, once a polymeric material has been included within the delivery device and heated to a flowable state, the nozzle of the delivery device (e.g., such as the tip of a needle, catheter, and/or squirt nozzle) may be inserted into an opening of a channel (or through the wall of cavity) to be occluded and the polymer may be dispensed out of the nozzle into the body cavity. The injection is preferably continued until the desired amount of occlusion (e.g., vasculature blockage) is obtained. In some instances, it may be desirable to occlude only part of a cavity. Thereafter, the nozzle of the delivery device may be withdrawn.

After the polymeric material has been delivered, the method may continue without operator interaction. For example, in the case of embolotherapy, the circulatory system of the mammal will typically cause a cooling effect on the surrounding tissues which will cool the injected polymeric material. The polymeric material is preferably selected such that it cools and solidifies after losing only a small amount of energy, i.e., hardens after decreasing in temperature by only a few degrees centigrade. Usually, cooling takes only a few seconds or minutes to occur, although there are times when it may be desirable for cooling to occur more slowly, e.g., in the case where a bone is reset after delivery. After cooling has taken place, the polymer preferably solidifies within the cavity in a manner conforming to the shape of the cavity and the channel is at least partially filled or blocked. The polymeric material may remain in place in the cavity over long periods of time. For preferred medical devices comprising biocompatible, non-immunogenic material, little or no adverse reaction is obtained. In certain embodiment, the polymer is bioresorbable, and thus may diminish over time, in which case surrounding tissue may fill the previously occluded region.

An effective cavity occlusion may also be achieved through the use of the polymer material described herein and various excipients. For instance, the polymer material may be delivered with (1) a photopolymerizable material that cross links through the use of a light; (2) a blood reactive substance that stimulates clotting such as collagen or thrombin, and/or (3) a nucleating agent.

In an embodiment, the polymeric material may be readily removed so as to again provide a cavity which functions in a normal manner. For example, it may be desirable to remove the polymeric material from a vas deferens or fallopian tube to restore fertility. The polymeric material may be removed in various ways. For example, the polymeric material may be removed by simple mechanical extraction. In certain instances, devices such as forceps and/or catheters with various attachment prongs connected thereto can be inserted into the channel and used to attach to the polymeric material and pull the polymeric material out of the cavity or force it forward into a second cavity so that the first cavity is no longer occluded and the polymeric material will not cause any damage. Alternatively, a device such as a heated wire may be brought into contact with the solidified polymeric material. By heating the polymeric material with the heated wire, the temperature of the polymeric material is raised above the melting point of the polymeric material so that it again becomes flowable. In the case of a channel (such as a duct or vein), the heating may be continued until the flowable polymeric material flows from the channel and the channel is reopened to provide normal function. In certain circumstances, the liquid plug can be drawn, aspirated or forced out of a channel, e.g., by suction with a gentle vacuum or by using mild pressure created by air or a saline flow and/or by mechanical breakup along with trapping and aspiration.

A preferred method of removing the solidified polymeric material from a channel or other cavity is to inject a lipophilic material such as naturally occurring oil or a fatty acid ester into the channel in the area surrounding the solidified polymeric material. Preferably, a lipophilic material is selected that has a tendency to diffuse into the polymeric material, thereby reducing its melting point. The lipophilic material is preferably added in an amount that is effective to reduce the melting point of the polymeric material below body temperature to such an extent that the polymer becomes flowable. Once the polymer becomes flowable, the natural mechanical movement that occurs within channels of living beings will tend to move the polymer from the channel, thereby restoring the normal function of the channel.

A medical device that comprises a polymeric material may include one or more additional components, e.g., a plasticizer, a filler, a crystallization nucleating agent, a preservative, a stabilizer, a photoactivation agent, etc., depending on the intended application. For example, in an embodiment, a medical device comprises an effective amount of at least one therapeutic agent and/or a magnetic resonance enhancing agent. Non-limiting examples of preferred therapeutic agents include a chemotherapeutic agent, a non-steroidal anti-inflammatory, a steroidal anti-inflammatory, and a wound healing agent. Therapeutic agents may be co-administered with the polymeric material. In a preferred embodiment, at least a portion of the therapeutic agent is contained within the polymeric material. In another embodiment, at least a portion of the therapeutic agent is contained within a coating on the surface of the medical device.

Non-limiting examples of preferred chemotherapeutic agents include taxanes, taxinines, taxols, paclitaxel, dioxorubicin, cis-platin, adriamycin, and bleomycin. Non-limiting examples of preferred non-steroidal anti-inflammatory compounds include aspirin, dexamethasone, ibuprofen, naproxen, and Cox-2 inhibitors (e.g., Rofexcoxib, Celecoxib and Valdecoxib). Non-limiting examples of preferred steroidal anti-inflammatory compounds include dexamethasone, beclomethasone, hydrocortisone, and prednisone. Mixtures comprising one or more therapeutic agents may be used. Non-limiting examples of preferred magnetic resonance enhancing agents include gadolinium salts such as gadolinium carbonate, gadolinium oxide, gadolinium chloride, and mixtures thereof.

Nucleating agents are materials that, in the presence of a polymer, make crystallization of the polymer more thermodynamically favorable. For example, a nucleating agent may accelerate polymer crystallization at a given temperature and/or induce crystallization (e.g., of a supercooled polymer) at a higher temperature than in the absence of the nucleating agent. Non-limiting examples of preferred nucleating agents include low molecular weight analogs of SCC polymers with higher peak crystallization temperatures than the bulk polymer being crystallized, carboxylate salts (such as sodium benzoate), inorganic salts (such as barium sulfate) and various particulate materials with relatively high surface area to volume ratios.

The amounts of additional components present in the medical device are preferably selected to be effective for the intended application. For example, a therapeutic agent is preferably present in the medical device in an amount that is effective to achieve the desired therapeutic effect in the patient to whom the medical device is administered or implanted. Such amounts may be determined by routine experimentation. In certain embodiments, the desired therapeutic effect is a biological response. In an embodiment, the therapeutic agent in the medical device is selected to promote at least one biological response, preferably a biological response selected from the group consisting of thrombosis, cell attachment, cell proliferation, attraction of inflammatory cells, deposition of matrix proteins, inhibition of thrombosis, inhibition of cell attachment, inhibition of cell proliferation, inhibition of inflammatory cells, and inhibition of deposition of matrix proteins. The amount of magnetic resonance enhancing agent in a medical devices is preferably an amount that is effective to facilitate radiologic imaging, and may be determined by routine experimentation.

An optimized polymer for use in the fabrication of a stent should fulfill at least some of the following criteria:

Radiopacity is preferably sufficient to ensure visibility of the stent structure against the background of a human chest by X-ray fluoroscopy, the standard method used in the clinic.

Stents according to aspects of the present invention are preferably formed with walls for providing a low crossing profile and for allowing excellent longitudinal flexibility. In preferred embodiments, the wall thickness is about 0.0001 inches to about 0.0250 inches, and more preferably about 0.0010 to about 0.0100 inches. However, the wall thickness depends, at least in part, on the selected material. For example, the thickness may be less than about 0.0060 inches for plastic and degradable materials and may be less than about 0.0020 inches for metal materials. More particularly, for a 3.00 mm stent application, when a plastic material is used, the thickness is preferably in the range of about 0.0040 inches to about 0.0045 inches. However, a stent having various diameters may employ different thicknesses for biliary and other peripheral vascular applications. The above thickness ranges have been found to provide preferred characteristics through all aspects of the device including assembly and deployment. However, it will be appreciated that the above thickness ranges should not be limiting with respect to the scope of the invention and that the teachings of the present invention may be applied to devices having dimensions not discussed herein.

The stents are preferably hemocompatible to prevent acute thrombosis. Accordingly, the device surfaces are preferably resistant to protein adsorption and platelet/monocyte attachment. Further, the device surfaces ideally favor endothelial overgrowth but discourage attachment and growth of smooth muscle cells (which are responsible for the occurrence of restenosis).

Stents preferably maintain their mechanical strength (e.g., hoop strength) for a period of about 1-24 months, more preferably about 3-18 months, more preferably still about 3-12 months, and most preferably about 3-6 months.

Stents preferably have a desirable biodegradation and bioresorption profile such that the stents reside for a period of time in the body lumen such that at a later time any stent, bioresorbable or metal or other, may be used to re-treat the approximate same region of the blood vessel or allow for other forms of vessel re-intervention such as vessel bypass.

In an embodiment, the medical device comprises a stent and/or a catheter, and thus the medical device may be a stent, or a stent system comprising a stent and a delivery catheter. The polymer may be incorporated into such a medical device in various ways. For example, in various embodiments, the body of the stent and/or catheter may comprise or consist essentially of a polymer described herein; the stent and/or catheter may be coated with a polymer described herein; the polymer described herein may be located at an interface between parts of the medical device, e.g., a between a stent and a catheter. In some medical device embodiments, the polymer is preferably biocompatible, and preferably has a melting point in the in the range of about 30° C. to about 80° C.

Prior to, during and/or after appropriate positioning within the blood vessel, the expandable stent may be heated to a temperature above the melting point and expanded by, e.g., use of a balloon catheter positioned within the stent, in a manner generally known to those skilled in the art. Optionally, a heated liquid may be circulated through the balloon catheter to provide heating to the expandable stent. After expansion, the stent may be cooled, e.g., by allowing it to cool to the temperature of the surrounding blood and/or tissue, and/or by circulating a cooling liquid through the balloon catheter. Upon cooling below the recrystallization temperature of the polymer (which may be different from or the same as the melting temperature), the stent becomes much more rigid and thus capable of providing the desired function, e.g., support of the blood vessel. The amount and type of polymer in the stent may be selected based on the temperature-dependent flexibility properties desired for the stent, as determined by routine experimentation.

In an embodiment, the medical device is a catheter, e.g., a device having any of the catheter designs described above. The polymer may be incorporated into such a catheter in various ways, as discussed above. In an embodiment, at least a portion of the polymer is positioned at a surface of the catheter. It has been found that such positioning of the polymer at a surface of the catheter allows the surface properties of the catheter to be manipulated as a function of temperature, e.g., the polymer may function as a temperature-dependent lubricant and/or adhesive as discussed above.

In an embodiment, a medical device is formed in vivo by introducing a polymeric material into a body cavity, then forming a channel through the polymeric material. For example, a stent may be formed by introducing a polymeric material described herein into a blood vessel in a manner similar to that described above for embolization, then forming a channel through the polymeric material. The channel is preferably substantially coaxial to the blood vessel, thus allowing blood to flow through the channel. The channel may be formed in various ways. For example, in one embodiment, the polymeric material is formed around a cylindrical mold. The polymer in the polymeric material is selected so that the adhesion between the mold and the polymeric material is greater at temperatures below the melting point of the polymer. The mold and polymeric material are then inserted into the vasculature and positioned to at least partially occlude a blood vessel. The mold is then heated to a temperature slightly above the melting point of the polymeric material, thereby reducing adhesion between the polymeric material and the mold. The mold is then withdrawn, leaving behind a cylindrical hole in the polymeric material. Withdrawal of the mold without undesirable repositioning of the polymeric material is facilitated by the temperature-dependent adhesive properties of the polymer. Other methods may also be used to form channels in polymeric materials, e.g., other mold shapes and configurations and/or by heating a portion of the polymeric material to a temperature above the melting point of the polymer or polymeric material. The size, shape, number and configuration of the channels may be controlled in various ways. For example, heat energy may be applied at various levels and in various forms, e.g., by laser and/or by inserting heated implements (such as a heated wire) into the polymeric material.

The highly beneficial combination of properties associated with the preferred halogenated polymers in accordance with embodiments of the present invention are well-suited for use in producing a variety of medical devices besides stents, especially in medical applications whereby the devices and/or applications to treat, repair, reconstruct, cosmetically augment, and heal are preferably radiopaque, biocompatible, and have various times of bioresorption. The invention may be administered in vivo on, in or around a tissue or organ. Likewise it may administered ex vivo onto an excised tissue and organ surface and/or used with another device or device component and then placed into the body. The invention may be administered with other synthetic substrates and/or biologic or engineered substrates and/or therapeutics.

For example, applicants have recognized that, in certain embodiments, in addition to stents, the polymers described herein are suitable for use in producing implantable devices with and without therapeutic agents, device components and/or coatings with and without therapeutic agents for other cardiovascular and peripheral vascular devices (e.g., heart, valves, arterial and venous blood vessels and microvasculature and cardiac muscle). In some preferred embodiments, the present halogenated polymers may be advantageously used in making various products that include therapeutic delivery systems for annuloplasty rings, stent grafts, closure devices, vascular grafts, sutures, and vascular cuffs (external to the vessel used for various reconstructions, repairs or treatments), septal defect repair devices, heart valve components, valves, valve repair devices, and/or heart closure devices (e.g., patent foramen ovale). Another embodiment provides a medical device configured for delivery of at least one therapeutic agent such as stem cells, genetic material, and tissues, wherein the medical device comprises a polymer that comprises at least one recurring unit of the formula (I), (Ia), and/or (XI).

Further, the polymers described herein may be used in implantable medical devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), pancreas (exocrine functions, biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

Non-limiting examples of medical devices that may comprise a polymer that comprises at least one recurring unit of the formula (I), (Ia), and/or (XI) include biocompatible orthopedic devices of which examples are described in U.S. Pat. Nos. 6,689,153 B1 and 6,280,473 B1, both of which are hereby incorporated by reference in their entirety. The polymer embodiments may be used for such as biocompatible pins, screws, sutures, tacks, clamps, and anchors; hip prosthesis and repair components, porous membranes, plates and rails for reconstructive skeletal applications (e.g., maxillofacial fractures, bone fractures, and osteotomies). The plates may be generally H-, O-, T-, L-, X- and/or Y-shaped plates, or other geometries such as triangular and oblong, all of which may be of various profiles and dimensions; designs, profiles and dimensions of such embodiments are described by Sarver et al., in U.S. Pat. No. 5,868,747 which is hereby incorporated by reference in its entirety. The plates may be preformed with fastener openings or be designed for drilling and securement upon use. Likewise the biocompatible polymers may be used as membranes, fabrics, meshes and fibrous forms of various dimensions, geometries and design for use in any non-embolic application in the body. Non-limiting examples of medical devices that may comprise a polymer that comprises at least one recurring unit of the formula (I), (Ia), and/or (XI) include a device for reconstruction of a tendon, ligament, joint, ear, nose, and other cartilaginous tissues, vascular and hemostatic closure devices, skin repair and augmentation and wound healing, adhesion barriers and the like. Furthermore embodiments may comprise a polymer that comprises at least one recurring unit of the formula (I), (Ia), and/or (XI) for use in cosmetic applications (e.g., a tissue filler to minimize wrinkles) and as sealer for instance in vascular and dental indications.

Medical devices that comprise a polymer that comprises at least one recurring unit of the formula (I), (Ia), and/or (XI) may include one or more additional components. Non-limiting examples of such additional components include, e.g., a supplementary amount of a radiopacifying agent, e.g., selected from the group consisting of iodine, bromine, barium, bismuth, gold, platinum, tantalum, tungsten, and mixtures thereof, a magnetic resonance enhancing agent; and/or an effective amount of at least one therapeutic agent (for example, a pharmaceutical agent and/or a biologic agent) sufficient to exert a selected therapeutic effect (e.g., at least one agent to treat infection (antibiotic and antimicrobial and antiviral), provide local anesthetization, enhance wound healing and the like), depending on the intended application. In a preferred embodiment, at least a portion of the therapeutic agent is contained within the polymeric material. In another embodiment, at least a portion of the therapeutic agent is contained within a coating on the surface of the medical device.

Furthermore, the polymers described herein may also be used for treatment of tumors in any organ and tissue system of the body. Further implantable, radiopaque discs, plugs, and other devices could be used as a "marker" to track treated regions (for instance as in the case of tumor removal). In some embodiment, the polymer described herein is inherently radiopaque. The inherent radiopaque character coupled with the biocompatibility of the polymers allows for their use as an additive to other polymer products to monitor their location and possibly duration by means of radiopacity. For instance, the radiopaque polymer could be used as a marker band on a catheter, a coating on a guide wire, pacemaker lead or any other device requiring radiopacity. The radiopaque polymer may be admixed with non-radiopaque polymers, by means known to those skilled in the art, to create a composite polymer implant with radiopacity.

The polymers described herein may also be used for filling a body space or structure such as a traumatized tissue or organ, a surgical biopsy core which may be small to large, a region created due tumor tissue excision and for tissue and organ enlargement such as in cosmetic applications, breast and penile enhancements. Filling may be done using the polymer inventions in many embodiments for instance by means of halogenated gels, foams, particles, fibers, or solid or semi-solid (e.g., various consistency or as at least partially or wholly porous devices, laminates, and/or composites). A polymer having inherent radiopaque character coupled with the biocompatibility of the polymers of this invention may be particularly suitable for treating damaged, destroyed or removed structures which may be created with an injectable polymer or implantable device; such a product could be used to reconstruct papilla of a breast or an external ear as in cancer patients as two examples.

A polymer having inherent radiopaque character coupled with the biocompatibility of the polymers described herein may be particularly suitable for orthopedic and spinal applications. These embodiments may be of many forms, for example but not limited to a solid, semi-solid and/or nonsolid form. This allows for rigid forms to provide enough inherent mechanical strength to withstand pressure from adjacent musculature and not collapse whereas the flexible variations may be more ideal for regions of soft tissue repair or motion. Examples of halogenated moldable or preformed devices, gels, slurries putty and clays include internal and external bone fixation devices, bone pins and screws and interference screws, and anchors, wound closure staples, tacks, sutures, membranes and the like; plating systems, spinal fusion devices, bone replacement, prosthetic ligament/tendon repair and replacements, and even for sophisticated treatments using computer aided design to create customized patient specific devices for repair, augmentation or otherwise such as craniofacial plates, chin implant, check bones et cetera. Other examples of embodiments include use of the polymers as an injectable cement, such as for vertebroplasty whereby the injectable seeps through the interstices of bone and becomes embedded between the pores of the trabeculae and hardens thereby increasing bone density. Further the polymer may be used as a putty or paste whereby the polymer is mixed with demineralized bone, gelatin, other biomaterial or substrate with or without a therapeutic (for instance at least one of a growth factor, bone morphogenetic protein, growth hormone, osteogenic growth peptide and the like) which may be useful for bone replacement, reconstruction and repair.

As detailed herein, various methods and techniques may be used to fabricate or manufacture the medical device embodiments of the invention. These include injection molding, laser machining, laser cutting, laser ablation, die-cutting, chemical etching, plasma etching or other methods known in the art which are capable of producing components, and if necessary, assembling the resulting cut portions into devices. The embodiments described may be fabricated into devices using various rapid prototyping (RP) techniques described in U.S. Pat. Nos. 5,490,962 and 6,530,958 B1 and by Hutmacher et al., (2004) which is hereby incorporated by reference. RP techniques applied to the fabrication of polymer devices may achieve simple and complex geometries. RP methods may be computer automated and integrated with imaging techniques to produce devices that are customized in size and shape to be tailored for specific applications and for individual patients. Such devices may guide cells and tissue during healing. One may also achieve simultaneous addition of cells during the scaffold fabrication with robotic assembly and automated 3D cell encapsulation techniques to develop tissue-engineered constructs with the polymers described herein.

Examples of RP techniques that may be used with polymers described here include: 1) solid free-form fabrication (SFF) (solvent based, solvent-free and aqueous-based systems) that builds parts by selectively adding materials, layer by layer, as specified by a computer program. Each layer represents the shape of the cross-section of the model at a specific level. SFF techniques offer unique ways to precisely control matrix architecture (size, shape, interconnectivity, branching, geometry and orientation) yielding biomimetic structures varying in design and material composition, thereby enhancing control over mechanical properties, biological effects and degradation kinetics of the scaffolds. SFF also allows inclusion of therapeutic agents. 2) Stereolithography (SLA) is a selective laser sintering technique that uses a $CO_2$ laser beam to sinter thin layers of powdered polymeric materials, forming solid 3D objects. 3) 3-D printing (3DP) technology forms devices layer by layer using an 'ink jet' print head and a binder solution deposited onto the powder bed. 4) Shape deposition manufacturing (SDM) involves the fabrication of a layered scaffold in a customized geometry by processing the clinical imaging data and translating it to the desired scaffold layer by a computer-numerically-controlled cutting machine. 5) Extrusion technology-based systems such as fused deposition modelling (FDM), 3-D plotting, multiphase jet solidification (MJS) and precise extrusion manufacturing (PEM) employ extrusion of a material in a layered fashion to build a scaffold. And, 6) solid ground curing (SGC) in designing devices by use of photochemically driven gelation technology of biomacromolecules that are chemically modified with photodimerizable groups. In this later instance the medical device may be partially rather than wholly biodegradable, e.g., if comprising the polymer described herein and one or more of the following photoreactive agents: polyethyleneglycol-based macromers, acrylated polyethyleneglycol derivatives including polyethylene glycol-co-polyhydroxy acid diacrylate and polyethylene glycol-polylysine diacrylate, both of which are end-capped with acryloyl groups.

As detailed herein, various methods and techniques of device delivery may be used for the embodiments of the invention. In certain embodiments, the medical devices described herein are non-embolic devices that do not include the embolic devices described in U.S. application Ser. No. 10/952,274, filed Sep. 27, 2004, published on May 19, 2005 as U.S. Patent Publication No. 2005/0106119 A1, which is hereby incorporated by reference in its entirety. Devices may be configured to be deliverable by physical surgical insertion, catheter, injection, pouring, spraying and/or squirting, extruded through single or multiple ports into a body region of a mammal. Further the devices may be thermally altered (e.g., cold pak, water bath, microwave, hot plates, hotpak, and use of a device such as that described in U.S. Pat. No. 5,263,991 which is hereby incorporated by reference) and formed and shaped by moulding over a form or mandrel and trimmed for use in a body region. Likewise the polymers may be made flowable for delivery into a body region for all non-embolic indications. Devices may placed directly in or on a body tissue or organ for example in subcutaneous and intramuscular tissue.

Promotion or prevention of cell ingrowth or selective integration of cells and matrix to regions of the scaffold may be accomplished by scaffold design. For instance, pore size may regulate which cell types grow into a porous scaffold. Implantable devices or scaffolds may have a pore size of zero microns (non-porous) to microporous (e.g., 1-200 microns) and macroporous (e.g., 200-1000 microns) as we define here for cell and tissue ingrowth. Devices may also be designed with chambers with pores of 1-1000 microns and chambers that are infinitely larger (macroporous chambers pores 1000 microns or greater) for cell and tissue interactions and reconstitution. Further the device may have regions that are wholly porous, partially porous or both. Whang proposes the pore sizes for fibroblast ingrowth between 20 and 125 microns for regeneration of adult mammalian skin, and 100-250 microns for regeneration of bone (Whang et al., 1995). Smooth surfaces versus rough surfaces are known to effect cell metabolism (Salthouse and Matlaga). Further cellular adhesion, alignment and topographical guidance, migration, attachment and proliferation and matrix production may be modified by altering the porosity, surface roughness and texture (e.g., ridges, spiral, geodesic patterns, spheres, grooves, convex, concave (von Recum et al., 1996; Curtis and Clark 1990). Additionally release of a therapeutic, such as a protein, may be controlled by unique microarchitecture (Whang et al., 1996). Generally the larger the pore size, for instance those of 30 or more microns in diameter, there is a likelihood that immune cells may infiltrate the foreign scaffold and capillaries may form.

Such devices of the polymers described herein may have pores, chambers or apertures sufficient in size and distribution to allow and optimize a proliferation of vasculature and connective tissue cells, derived from adjacent hard and soft tissues, to permeate through and substantially into the defect to heal the region. Such devices may be chemically formulated and adapted to be biodegraded in the body within a period of approximately 2 or more months from an initial implantation.

Additionally the polymers described herein may be used for in vitro to develop tissue engineered implants or for use for direct implantation to a body region as a carrier or chamber to deliver cells (e.g., encapsulated islet cells and/or suspended cells), other materials (e.g., therapeutics, biologics) and/or tissue.

Furthermore, the polymers described herein may also be used for soft tissues. Some examples include anti-adhesion barriers for epicardial, abdominal and pelvic adhesions. In another preferred embodiment the polymers described herein may be used as an implantable mesh or substrate for soft organ reconstruction (e.g., intestine, liver, skin) and for topical sealants applied to any device used for implant, and administered to any incision and cauterization.

Moreover the polymers described herein may be used for in vitro as well, for instance, production and engineering of cells and tissues for transplantation, in vitro cell culture studies for cryopreservation, immunomodulation, immunoisolation, studies of cells (mature, differentiated, fetal, pluripotent stem cells) gene therapy, morphogenesis, for use in bioreactors, studies of kinetics, transport, and mechanics of cells, tissue, organs and engineered devices, cell interaction studies with polymers and scaffolds, and polymer biodegradation studies. Additionally the polymers described herein may be used for in vitro diagnostic testing. As a nonlimiting example, the polymer may be used as a support surface for reactive test agents (e.g., therapeutic agent, cells and other biologics).

In light of the disclosure herein, those of skill in the art will be readily able to fabricate a variety of medical devices that comprise one or more of the polymers described herein (e.g., a polymer comprising at least one recurring unit of the formula (I), (Ia), and/or (XI)). After polymerization, appropriate work up of the polymers in accordance with preferred embodiments may be achieved by any of a variety of known methods to produce a variety of stents or other medical devices, suitable for various applications. For example, in certain preferred embodiments, the present polymers are shaped into stents via methods comprising extrusion, compression molding, injection molding, solvent casting, spin casting, combinations of two or more thereof, and the like. Further, stents may be comprised of at least one fiber material, curable material, laminated material, and/or woven material.

Such processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms. In certain other embodiments, the polymers are formed into coatings on the surface of an implantable device, particularly a stent, made either of a polymer of the present invention or another material, such as metal. Such coatings may be formed on stents via techniques such as dipping, spray coating, combinations thereof, and the like.

A stent produced in accordance with preferred aspects of the present invention may be of any design (e.g., slide-and-lock stents, sheet stents (sometimes referred to as jelly-roll stents), deformable stents, and self-expanding stents) suitable for a given application. Preferably, the stents of the present invention are designed to be readily implantable in the artery or tissue of an animal, such as a human, and to be expandable and/or suitable for holding open an artery, after said artery is opened via a medical procedure, such as an angioplasty. Examples of suitable stent designs for use in the present invention include "slide-and-lock" stents, including those disclosed in U.S. Pat. Nos. 6,033,436; 6,224,626 and 6,623,521, and co-pending U.S. patent application Ser. No. 11/016,269 filed Dec. 17, 2004, all of which are incorporated herein by reference.

Other suitable designs adaptable for use herein include those used traditionally in metal and polymeric stents, including various mesh, jelly-roll, sheet, zigzag, and helical coil designs, e.g., the deformable stents by Palmaz such as U.S. Pat. No. 4,733,665 and its successors which have controllable expansion and a portion of the prosthesis that deforms with a force in excess of the elastic limit. Other stent designs include the following designs and their successors: U.S. Pat. No. 5,344,426 by Lau, U.S. Pat. Nos. 5,549,662 and 5,733,328 by Fordenbacher, U.S. Pat. Nos. 5,735,872 and 5,876,419 by Carpenter, U.S. Pat. No. 5,741,293 by Wijay, U.S. Pat. No. 5,984,963 by Ryan, U.S. Pat. Nos. 5,441,515 and 5,618,299 by Khosravi, U.S. Pat. Nos. 5,059,211; 5,306,286 and 5,527,337 by Stack, U.S. Pat. No. 5,443,500 by Sigwart, U.S. Pat. No. 5,449,382 by Dayton, U.S. Pat. No. 6,409,752 by Boatman, and the like.

The polymers described herein are further useful in the production of a wide variety of therapeutic delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body may be made, including devices for therapeutics delivery in the treatment of cancer, intravascular problems, dental problems, obesity, infection, control of reproduction and the like. In certain embodiments, any of the aforementioned devices described herein may be adapted for use as a therapeutic delivery device (in addition to any other functionality thereof). Controlled therapeutic delivery systems may be prepared, in which a biologically or pharmaceutically active and/or passive agent is physically embedded or dispersed within a polymeric matrix or physically admixed with a polycarbonate or polyarylate of the present invention. Controlled therapeutic delivery systems may also be prepared by direct application of the therapeutic to the surface of a bioresorbable stent device (comprised of at least one of the present polymers) without the use of these polymers as a coating, or by use of other polymers or substances for the coating.

One major advantage of using a radiopaque, bioresorbable polymer described herein in therapeutic delivery applications is the ease of monitoring the release of a therapeutic and the presence of the implantable therapeutic delivery system. Because the radio-opacity of the polymeric matrix is due to covalently attached halogen substituents, the level of radio-opacity is directly related to the residual amount of the degrading therapeutic delivery matrix still present at the implant site at any given time after implantation. In preferred embodiments, the rate of therapeutic release from the degrading therapeutic delivery system will be correlated with the rate of polymer resorption. In such preferred embodiments, the straightforward measurement of the residual degree of radio-opacity will provide the attending physician with a way to monitor the level of therapeutic release from the implanted therapeutic delivery system.

Stent surface coatings using polymers having functional properties that support biological responses: In addition to stents that may deliver a therapeutic agent, for instance delivery of a biological polymer on the stent such as a repellant phosphorylcholine, the stent may be coated with other bioresorbable polymers predetermined to promote biological responses in the vessel lumen desired for certain clinical effectiveness. The coating may be selected from the broad class of any biocompatible bioresorbable polymer which may include any one or combination of halogenated and/or non-halogenated tyrosine-derived polycarbonates, tyrosine-derived polyarylates, poly(ester amides), poly(amide carbonates), trimethylene carbonate, polycaprolactone, polydioxane, polyhydroxybutyrate, poly-hydroxyvalerate, polyglycolide, polylactides and stereoisomers and copolymers thereof such as glycolide/lactide copolymers. In a preferred embodiment, the stent is coated with a polymer that exhibits a negative charge that repels the negatively charged red blood cells' outer membranes thereby reducing the risk of clot formation. In another preferred embodiment, the stent is coated with a polymer that exhibits an affinity for cells, (e.g., endothelial cells) to promote healing. In yet another preferred embodiment, the stent is coated with a polymer that repels the attachment and/or proliferation of specific cells, for instance arterial fibroblasts and/or smooth muscle cells in order to lessen restenosis and/or inflammatory cells such as macrophages.

In preferred embodiments, the medical device is configured for placement in a region of the vascular, musculoskeletal/orthopedic, nervous, respiratory, reproductive, urinary, digestive, endocrine, hematopoietic and/or the integumentary system. In an embodiment, the medical device is configured for placement in the reproductive system for use other than the treatment of uterine fibroids.

In another embodiment, the medical device comprises a non-halogenated coating.

Described above are the bioresorbable polymer stents of the present invention that may be modified with a coating to achieve functional properties that support biological responses. Likewise, the other aforementioned medical devices and/or device components of inherently radiopaque bioresorbable polymers may also be modified with a coating as previously stated, to achieve functional properties that support biological responses.

Stent Design

Preferred embodiments of the invention described herein relate generally to expandable medical implants for maintaining support of a body lumen. Over the years, a wide variety of stent types have been proposed. Although the structures of stents may vary substantially, virtually all stents are configured to be expandable from a collapsed condition having a small diameter to an expanded condition having a larger diameter. While in the collapsed condition, the stent is delivered usually via catheter through the blood vessel, or other body lumen, to the treatment site. After the treatment site is reached, the stent is radially expanded to an implantable size for supporting the vessel wall. Expansion of the stent from the collapsed condition to the expanded condition may be achieved in a variety of different ways. Various types of stents are described below based on their configurations and means for expansion. For additional information, a variety of stents types are described by Balcon et al., "Recommendations on Stent Manufacture, Implantation and Utilization," European Heart Journal (1997), vol. 18, pages 1536-1547, and Phillips, et al., "The Stenter's Notebook," Physician's Press (1998), Birmingham, Mich.; the disclosures of which are incorporated herein by reference in their entirety.

Balloon expandable stents are manufactured in the collapsed condition and are expanded to a desired diameter with a balloon. During delivery, a balloon expandable stent is typically mounted on the exterior of an inflatable balloon located along the distal end portion of a catheter. After reaching the treatment site, the stent is expanded from the collapsed condition to the expanded condition by inflating the balloon. The stent is typically expanded to a diameter that is greater than or equal to the inner diameter of the body lumen. The expandable stent structure may be held in the expanded condition by mechanical deformation of the stent as taught in, for example, U.S. Pat. No. 4,733,665 to Palmaz. Alternatively, balloon expandable stents may be held in the expanded condition by engagement of the stent walls with respect to one another as disclosed in, for example, U.S. Pat. Nos. 4,740,207 to Kreamer, 4,877,030 to Beck et al., and 5,007,926 to Derbyshire. Further still, the stent may be held in the expanded condition by one-way engagement of the stent walls together with endothelial growth into the stent, as shown in U.S. Pat. No. 5,059,211 to Stack et al.

The term "radial strength," as used herein, describes the external pressure that a stent is able to withstand without incurring clinically significant damage. Due to their high radial strength, balloon expandable stents are commonly used in the coronary arteries to ensure patency of the vessel. During deployment in a body lumen, the inflation of the balloon may be regulated for expanding the stent to a particular desired diameter. Accordingly, balloon expandable stents may be used in applications wherein precise placement and sizing are important. Balloon expandable stents may also be commonly used for direct stenting, wherein there is no pre-dilation of the vessel before stent deployment. Rather, during direct stenting, the expansion of the inflatable balloon dilates the vessel while also expanding the stent.

One of the first self-expanding stents used clinically is the braided "WallStent," as described in U.S. Pat. No. 4,954,126 to Wallsten. The WallStent generally comprises a metallic mesh in the form of a Chinese finger cuff. The cuff provides a braided stent that is not superelastic, but technically still falls in the self-expanding stent family. Another example of a self-expanding stent is disclosed in U.S. Pat. No. 5,192,307 to Wall wherein a stent-like prosthesis is formed of polymeric or sheet metal that is expandable or contractible for placement. The stent may be biased in an open position and lockable in a closed position or, alternatively, may be biased towards a closed position and lockable in an open position. In the former case, a pin may be used to hold the stent in the collapsed condition. The pin is removed to allow the stent to assume the expanded condition. One or more hooks may be formed into the wall for locking the stent. The hooks engage complementary recesses formed in an opposing wall to mechanically interlock the rolled up sheet forming the stent.

Heat expandable stents are similar in nature to self-expanding stents. However, this type of stent utilizes the application of heat to produce expansion of the stent structure. Stents of this type may be formed of a shape memory alloy, such as Nitinol. Still other types of heat expandable stents may be formed with a tin-coated, heat expandable coil. Heat expandable stents may be delivered to the affected area on a catheter capable of receiving a heated fluid. Heated saline or other fluid may be passed through the portion of the catheter on which the stent is located, thereby transferring heat to the stent and causing the stent to expand.

It is desirable that a stent be balloon expandable for providing accurate placement and sizing at a treatment site. It is also desirable that such a stent has sufficient radial strength to maintain patency of the lumen while subjected to substantial external forces. It is also desirable that such a stent be configured to exhibit little or no longitudinal shortening during radial expansion. It is also desirable that such a stent be sufficiently flexible along the longitudinal axis to conform to the curved shape of a body lumen. It is also desirable that such a stent has the capability to conform to the interior of the body lumen.

While various stent configurations, including without limitation, sheet stents, braided stents, self-expanding stents, wire stents, deformable stents, and a slide-and-lock stents, are known in the art, it will be appreciated that the description is illustrative only and should not be construed in any way as limiting the invention. Indeed, the radiopaque, bioresorbable polymers described herein may be applicable to a variety of other stent designs that are known in the art. Furthermore, various applications of the invention, and modifications thereto, which may occur to those who are skilled in the art, are also encompassed by the general concepts described herein.

Some preferred embodiments relate to an expandable slide-and-lock stent having a plurality of modules. The modules have a plurality of sliding and locking elements permitting one-way sliding of the radial elements from a collapsed diameter to an expanded/deployed diameter, but inhibiting radial recoil from the expanded diameter. One advantage is that the stent design elements of the modules and interlocks may be varied to customize the functional features of strength, compliance, radius of curvature at deployment and expansion ratio. In some preferred embodiments, the stent comprises a polymer described herein, such that the stent comprises a radiopaque, bioresorbable material, which is adapted to vanish over time. In some embodiments, the stent serves as a therapeutic delivery platform.

Some embodiments relate to a radially expandable stent used to open, or to expand a targeted area in a body lumen. In some embodiments, the assembled stent comprises a tubular member having a length in the longitudinal axis and a diameter in the radial axis, of appropriate size to be inserted into the body lumen. The length and diameter of the tubular member may vary considerably for deployment in different selected target lumens depending on the number and configuration of the structural components, described below. The tubular member is adjustable from at least a first collapsed diameter to at least a second expanded diameter. One or more stops and engaging elements or tabs are incorporated into the structural components of the tubular member whereby recoil (i.e., collapse from an expanded diameter to a more collapsed diameter) is minimized to less than about 5%.

The tubular member in accordance with some embodiments has a "clear through-lumen," which is defined as having no structural elements protruding into the lumen in either the collapsed or expanded diameters. Further, the tubular member has smooth marginal edges to minimize the trauma of edge effects. The tubular member is preferably thin-walled (wall thickness depending on the selected materials ranging from less than about 635 to less than about 100 micrometers) and flexible (e.g., less than about 0.01 Newtons force/millimeter deflection) to facilitate delivery to small vessels and through tortuous vasculature. The thin walled design will also minimize blood turbulence and thus risk of thrombosis. The thin profile of the deployed tubular member in accordance with some embodiments also facilitates more rapid endothelialization of the stent.

The wall of the tubular member may comprise at least one module, which comprises a series of sliding and locking radial elements. Preferably, a plurality of modules are connected in the longitudinal axis via linkage elements which couple at least some of the radial elements between adjacent modules. The radial elements are preferably configured within each module so as to define the circumference of the tubular member. Each radial element within a module is preferably a structurally discrete, unitary structure, which is physically separate from other radial elements within the module, and comprises one or more circumferential ribs bowed in the radial axis to form a fraction of the total circumference of the tubular member. At least one of the ribs in each radial element has one or more stops disposed along the length of the rib. At least some of the radial elements also have at least one articulating mechanism for slideably engaging the rib(s) from adjacent, circumferentially offset radial elements. In one aspect of the invention, the articulating mechanism includes a tab for engaging the stops disposed along the slideably engaged adjacent rib. The articulating between the tab from one radial element and the stops from an adjacent radial element is such that a locking or ratcheting mechanism is formed, whereby the adjacent radial elements may slide circumferentially apart from one another, but are substantially prevented from sliding circumferentially toward one another. Accordingly, the tubular member may be radially expanded from a smaller diameter to a larger diameter, but recoil to a smaller diameter is preferably minimized by the locking mechanism.

Other preferred embodiments of slide-and-lock stents, include, but are not limited to, a non-actuating slide-and-lock stent with radial elements following a defined path geometry having both radial and axial translation; a slide-and-lock stent with longitudinal modules comprising both active (slide-and-lock) and passive radial elements wherein the radial elements have a variety of features including, but not limited to, spring elements, frangible deployment control mechanism and device overextension safety catches; a slide-and-lock stent with non-symmetric lockout geometries for enhanced sizing resolution; an actuating slide-and-lock stent with a positive lockout mechanism return; an actuating slide-and-lock stent with an active lockout system; a deformable slide-and-lock stent which provides additional device radial expansion and/or increases device safety; a slide-and-lock stent with two sided lockout features; a crimpable slide-and-lock stent for enhanced retention on a delivery balloon; and a slide-and-lock stent with optimized strut or wall configuration to reduce turbulence and create generally laminar flow of the blood. Further embodiments include a slide-and-lock stent with a region with a high surface area region for support; a slide-and-lock stent with a region with a side-branch vessel access port; and, a slide-and-lock stent with a graft covering. Further embodiments include a slide-and-lock stent comprised of layered materials and/or spatially localized materials.

With reference now to FIG. 1, a portion of a preferred stent embodiment 320 is illustrated wherein radial elements 320A(1), 320A(2) are slidably interconnected. Each radial element is provided with a rail 328 having a plurality of deflectable teeth 326. Each of the teeth is angled upward and is configured to deflect downward (i.e., in a radial direction). As the locking tabs 322, 324 slide along the deflectable teeth 326, the teeth are caused to deflect downward for allowing the tabs 322, 324 to pass over the teeth 326 during deployment. However, due to the angle of the teeth, the locking tabs may only move in one direction. More particularly, if a compressive force pushes the radial elements 320A(1), 320A(2) back toward the collapsed condition, the locking tabs 322, 324 will abut against the teeth 326, thereby preventing further relative movement.

Some aspects of additional embodiments of stents are disclosed in U.S. Pat. Nos. 6,033,436, 6,224,626 and 6,623,521 and co-pending U.S. application Ser. Nos. 10/897,235 filed on Jul. 21, 2004 and 11/016,269 filed on Dec. 17, 2004; all of which are hereby incorporated in their entirety by reference thereto.

Although a stent formed from a single integral element is described above as having particular mechanical characteristics for locking the stent in the expanded condition, a variety of other "slide and lock" mechanisms may be used. For example, other suitable locking mechanism may be found in U.S. Pat. No. 5,344,426 to Lau, U.S. Pat. Nos. 5,735,872 and 5,876,419 to Carpenter, U.S. Pat. No. 5,741,293 to Wijay, U.S. Pat. No. 5,984,963 to Ryan, U.S. Pat. Nos. 5,441,515 and 5,618,299 by Khosravi, U.S. Pat. No. 5,306,286 to Stack, U.S. Pat. No. 5,443,500 to Sigwart, U.S. Pat. No. 5,449,382 to Dayton, U.S. Pat. No. 6,409,752 to Boatman, and the like. Each of these references is incorporated by reference herein. In addition, many of the slide and lock mechanisms disclosed in the above patents may be suitable for use with stents embodiments comprising slidable interconnected elements of the type described above.

Therapeutic agents may be incorporated into the bioresorbable stent and/or coated on at least one region of the stent surface, thereby providing local release of such agents. In preferred embodiments, the therapeutic agent is contained within the stent as the agent is blended with the polymer or admixed by other means known to those skilled in the art. In other preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent.

The preferred therapeutic agent(s) control restenosis (including neointimal thickening, intimal hyperplasia and in-stent restenosis or limits vascular smooth muscle cell overgrowth) in the lumen of a stented vessel. Vascular stent applications and other body applications may require a different therapeutic or more than one therapeutic.

A variety of compounds are considered to be useful in controlling vascular restenosis and in-stent restenosis. Some of these preferred agents that improve vascular patency include without limitation paclitaxel, Rapamycin, ABT-578, everolimus, dexamethasone, nitric oxide modulating molecules for endothelial function, tacrolimus, estradiol, mycophenolic acid, C6-ceramide, actinomycin-D and epothilones, and derivatives and analogs of each.

The preferred therapeutic agent may also limit or inhibit thrombosis or affect some other state of the stented tissue, for instance, heal a vulnerable plaque, inhibit plaque rupture, stimulate endothelialization or limit other cell types from proliferating and from producing and depositing extracellular matrix molecules. The agent(s) may be selected from the group consisting of but not limited to: antiproliferative agents, anti-inflammatory, anti-matrix metalloproteinase, and lipid lowering, anti-thrombotic and antiplatelet agents, in accordance with preferred embodiments of the present invention.

In a preferred stent embodiment the device delivers a therapeutic agent(s) to treat the vulnerable plaque lesion such as an anti-inflammatory, a lipid lowering/matrix altering therapeutic and/or an antiproliferative. The anti-inflammatory may include aspirin, an effective neutralizer of inflammation, losartan, an angiotensin receptor blocker or pravastatin, a 3-Hydroxy-3-Methyl-Glutaryl Coenzyme A (HMG-CoA) reductase inhibitor. Further delivery of statins, such as pravastatin and fluvastatin, which are 3-HMG-CoA reductase inhibitors may interstitial collagen gene expression and lower matrix metalloproteinases (MMP-1, MMP-3, and MMP-9) expression to effectively stabilize the vulnerable plaque lesions. Local stent delivery of lipid-lowering agent, for example Pravastatin, may also improve plaque stability.

In a preferred stent embodiment the device delivers an antiplatelet agent that acts by glycoprotein IIb/IIIa receptor inhibition or other means such as but not limited to aspirin, Plavix (clopidogrel bisulfate), ticlopidine, integrelin, and dipyridamole. In another preferred stent embodiment the device delivers an antithrombin agent that acts by thrombin inhibition or other means such as heparin, low molecular weight heparin (LMWH), polyamine to which dextran sulfate and heparin are covalently bonded, heparin-containing polymer coating for indwelling implants (MEDI-COAT by STS Biopolymers), polyurethane urea/heparin, R-Hirudin, Hirulog, hirudin/prostacyclin and analogues, argatroban, efegatran, and tick anticoagulant peptide. Additional anti-thrombogenic substances and formulations may include but are not limited to endothelium-derived relaxing factor, prostaglandin $I_2$, plasminogen activator inhibitor, tissue-type plasminogen activator (tPA), ReoPro: anti-platelet glycoprotein IIb/IIIa integrin receptor, fibrin and fibrin peptide A, lipid-lowering drugs, e.g., Omega-3 fatty acids, and Chrysalin (aka TRAP-508) by Chrysalis Vascular Technologies.

Various compounds address other pathologic events and/or vascular diseases. Some of these therapeutic target compounds are agents to treat endothelial injury (e.g., VEGF; FGF), agents to modulate cell activation and phenotype (e.g., MEF-2 & Gax modulators; NFKB antagonists; cell cycle inhibitors), agents for dysregulated cell growth (e.g., E2F decoys; RB mutants; cell cycle inhibitors), agents for dysregulated apoptosis (e.g., Bax or CPP32 inducers; Bcl-2 inhibitors; integrin antagonists) and agents for abnormal cell migration (e.g., integrin antagonists; PDGF blockers; plasminogen activator inhibitors).

The therapeutic agents to be coated or incorporated within the stent polymer of embodiments of the invention may be classified in terms of their sites of action in the host. The following agents are believed to exert their actions extracellularly or at specific membrane receptor sites. These include corticoids and other ion channel blockers, growth factors, antibodies, receptor blockers, fusion toxins, extracellular matrix proteins, peptides, or other biomolecules (e.g., hormones, lipids, matrix metalloproteinases, and the like), radiation, anti-inflammatory agents including cytokines such as interleukin-1 (IL-1), and tumor necrosis factor alpha (TNF-α), gamma interferon (interferon-γ), and Tranilast, which modulate the inflammatory response.

Other groups of agents exert their effects at the plasma membrane. These include those involved in the signal transduction cascade, such as coupling proteins, membrane associated and cytoplasmic protein kinases and effectors, tyrosine kinases, growth factor receptors, and adhesion molecules (selectins and integrins).

Some compounds are active within the cytoplasm, including for example, heparin, ribozymes, cytoxins, antisense oligonucleotides, and expression vectors. Other therapeutic approaches are directed at the nucleus. These include gene integration, proto-oncogenes, particularly those important for cell division, nuclear proteins, cell cycle genes, and transcription factors.

Other therapeutic substances that may be useful as stent coatings and/or depot formulations incorporated within bioresorbable stents include: antibodies e.g., ICAM-1 antibodies for inhibition of monocyte chemotactic recruitment and adhesion, macrophage adhesion and associated events (Yasukawa et al, 1996, Circulation); toxin based therapies such as chimeric toxins or single toxins to control vascular SMC proliferation (Epstein et al., 1991, Circulation); bFGF-saporin to selectively stop SMC proliferation among those cells with a large number of FGF-2 receptors (Chen et al, 1995, Circulation), suramin inhibits migration and proliferation by blocking PDGF-induced and/or mitogen activated protein kinase (MAPK-AP-1)-induced signaling (Hu et al, Circulation, 1999); Beraprost Sodium, a chemically stable prostacyclin analogue ($PGI_2$), suppresses intimal thickening and luminal narrowing of coronary arteries. (Kurisu et al., Hiroshima J. Med Sci, 1997); Verapamil inhibits neointimal smooth muscle cell proliferation (Brauner et al., J Thorac Cardiovasc Surg 1997), agents that block the CD 154 or CD40 receptor may limit the progression of atherosclerosis (E Lutgens et al., Nature Medicine 1999), agents that control responses of shear stress response elements or mechanical stress or strain elements or heat shock genes; and anti-chemoattractants for SMC and inflammatory cells.

In addition or in the alternative, cells could be encapsulated in a bioresorbable microsphere, or mixed directly with polymer, or hydrogel. Living cells could be used to continuously deliver molecules, for instance, cytokines and growth factors. Cells of any origin may be used in accordance with this aspect of the present invention. Further, nonliving cells may be used and preserved or dehydrated cells which retain their purpose when rehydrated may be used. Native, chemically modified processed), and/or genetically engineered cells may be used.

Therapeutic agents may be polar or possess a net negative or positive or neutral charge; they may be hydrophobic, hydrophilic or zwitterionic or have a great affinity for water. Release may occur by controlled release mechanisms, diffusion, interaction with another agent(s) delivered by intravenous injection, aerosolization, or orally. Release may also occur by application of a magnetic field, an electrical field, or use of ultrasound.

In another aspect of the invention, the stent may also incorporate or deliver a hydrogel or other material such as phosphorylcholine (PC) that acts to prevent adhesions of blood cells, blood proteins or blood molecules, extracellular matrix or other cell types. The hydrogel may deliver a therapeutic agent.

Use of synthetic, natural (plant, microbial, viral or animal-derived) and recombinant agents having selected functions or chemical properties may be mixed with complementary substances (e.g., anti-thrombotic and anti-restenosis substances; nucleic acids and lipid complexes). Pharmacologic agents may also incorporate use of vitamins or minerals. For instance, those that function directly or indirectly through interactions or mechanisms involving amino acids, nucleic acids (DNA, RNA), proteins or peptides (e.g., RGD peptides), carbohydrate moieties, polysaccharides, liposomes, or other cellular components or organelles for instance receptors and ligands.

Genetic approaches to control restenosis include without limitation: use of antisense oligonucleotides to PDGFR-ββ mRNA to control PDGF expression; use of antisense oligonucleotides for nuclear antigens c-myb or c-myc oncogenes (Bauters et al., 1997, Trends CV Med); use of antisense phosphorothioate oligodeoxynucleotides against cdk 2 kinase (cyclin dependent kinase) to control the cell cycle of vascular smooth muscle cells (Morishita et al, 1993, Hypertension); use of VEGF gene (or VEGF itself) to stimulate reconstructive wound healing such as endothelialization and decrease neointima growth (Asahara et al 1995); delivery of the nitric oxide synthetase gene (eNOS) to reduce vascular smooth muscle cell proliferation (Von Der Leyen et al., 1995, Proc Natl Acad Sci); use of adenovirus expressing plasminogen activator inhibitor-1 (PAI-1) to reduce vascular smooth muscle cell migration and thereby diminish restenosis (Carmeliet et al., 1997, Circulation); stimulation of apolipoprotein A-1 (ApoA1) over-expression to rebalance serum levels of LDL and HDL; use of apoptosis gene products to promote cell death (e.g., of smooth muscle cells) and cytotactic gene products to that regulate cell division (tumor suppressor protein p53 and Gax homeobox gene product to suppress ras; p21 over expression); and inhibition of NF-κB activation (e.g., p65) to control smooth muscle cell proliferation (Autieri et al., 1994, Biochem Biophys Res Commun).

Described above are the polymer stents of the present invention that deliver a therapeutic agent. Likewise, the other aforementioned medical devices and/or device components of polymers described herein may also deliver a therapeutic agent as previously stated.

In addition to their usefulness in medical devices, the polymers described herein may also be useful for in vitro testing, diagnostics and production with cells, tissue, and/or organs and bioengineered materials.

In an embodiment, the stent is selected from the group consisting of a sheet stent, a braided stent, a self-expanding stent, a wire stent, a deformable stent, and a slide-and-lock stent. In an embodiment, the stent comprises a self-expanding stent. In an embodiment, the self-expanding stent comprises a heat expandable portion that is temperature-dependent-expandable. In an embodiment, the heat expandable portion is expandable at a temperature above a melting point of the polymer.

The medical devices, including the stents, described herein may be made radiopaque by incorporation of the polymer described herein. In an embodiment, the stents are bioresorbable and radiopaque. The stents, as disclosed in accordance with preferred embodiments of the present invention, may be used, for example, to temporarily treat a blood vessel as in traditional applications which generally include delivery through a catheter.

In an embodiment, at least a portion of the polymer is positioned at a surface of the stent. In an embodiment, the polymer described herein forms a coating on at least a portion of the medical device. In an embodiment, the medical device comprises the polymer described herein.

In an embodiment, the medical device further comprises an effective amount of at least one therapeutic agent. In an embodiment, the therapeutic agent is selected from the group consisting of antiproliferative agent, anti-inflammatory agent, anti-matrix metalloproteinase agent, lipid lowering agent, cholesterol modifying agent, anti-thrombotic agent, and antiplatelet agent. In an embodiment, the effective amount is sufficient to provide an effect selected from the group consisting of inhibition of restenosis, inhibition of thrombosis, inhibition of plaque formation, inhibition of plaque rupture, inhibition of inflammation, lowering of cholesterol, and promote healing.

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the preferred embodiments. At the very least, and not as an attempt to limit the application of the doctrine of equivalents to the scope of the claims, each numerical parameter should be construed in light of the number of significant digits and ordinary rounding approaches.

The above description discloses several methods and materials of the preferred embodiments. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A polymer that comprises a recurring unit of the formula (I):

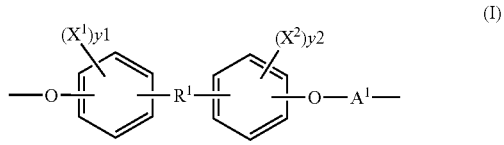

wherein:
$X^1$ and $X^2$ in formula (I) are each independently selected from the group consisting of Br and I;
$y^1$ and $y^2$ in formula (I) are each independently zero or an integer in the range of 1 to 4;
$A^1$ in formula (I) is selected from the group consisting of

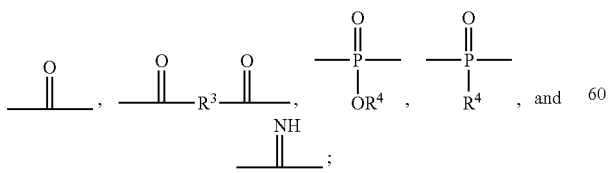

$R^3$ in formula (I) is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl;

$R^4$ in formula (I) selected from the group consisting of H, $C_1$-$C_{30}$ alkyl, and $C_1$-$C_{30}$ heteroalkyl;

$R^1$ in formula (I) is

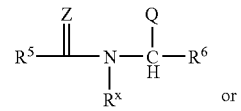

or

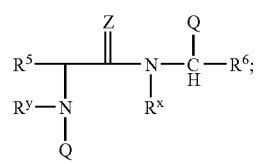

Z in formula (I) is O or S;
$R^5$ and $R^6$ in formula (I) are each independently selected from the group consisting of —CH=CH—, —CHJ$^1$-CHJ$^2$-, and —(CH$_2$)$_a$—;
a in formula (I) is zero or an integer in the range of 1 to 8;
$J^1$ and $J^2$ in formula (I) are each independently selected from the group consisting of H, Br, and I;
Q in formula (I) is a group comprising about 20 or more carbon atoms;
$R^x$ in formula (I) is selected from optionally substituted branched or unbranched $C_1$-$C_{30}$ alkyl and optionally substituted $C_6$-$C_{30}$ aryl; and
$R^y$ in formula (I) is selected from hydrogen, optionally substituted branched, or unbranched $C_1$-$C_{30}$ alkyl and optionally substituted $C_6$-$C_{30}$ aryl.

2. The polymer according to claim 1, wherein in formula (I) is a branched or unbranched $C_1$-$C_6$ alkyl.

3. The polymer according to claim 1, wherein $R^x$ in formula (I) is a methyl.

4. The polymer according to claim 1, wherein:
$X^1$ and $X^2$ in formula (I) are each I;
$A^1$ in formula (I) is

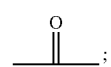

$R^1$ in formula (I) is

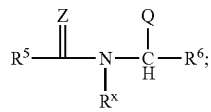

Z in formula (I) is O; and
$R^5$ and $R^6$ in formula (I) are each independently selected from the group consisting of —CH=CH— and —(CH$_2$)$_a$—.

5. The polymer according to claim 1, wherein Q in formula (I) comprises from about 20 to about 30 carbon atoms.

6. The polymer according to claim 1, wherein Q in formula (I) is a group that comprises the formula (VII):

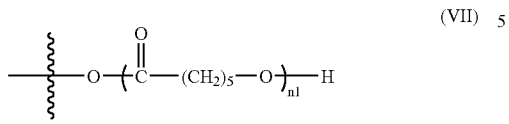

wherein n1 in formula (VII) is an integer in the range of about 1 to about 1,000.

7. The polymer to claim 1, wherein $R^5$ in formula (I) is —CH=CH— or —$(CH_2)_a$—; $R^6$ in formula (I) is —$(CH_2)_a$—; and Q in formula (I) is an ester group comprising from about 20 to about 30 carbon atoms.

8. The polymer to claim 1, wherein Z in formula (I) is O or S and $J^1$ and $J^2$ in formula (I) are each independently selected from the group consisting of Br and I.

9. The polymer according to claim 1, further comprising a recurring unit of the formula (II):

wherein $R^7$ in formula (II) is H or $CH_3$; $A^3$ in formula (II) is a chemical group having a molecular weight of about 500 or less; and $A^3$ in formula (II) bears at least one heavy atom attached to the polymer.

10. The polymer of according to claim 1, further comprising a recurring unit of the formula (III):

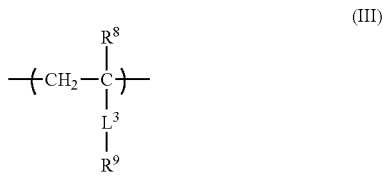

wherein $R^8$ in formula (III) is H or $CH_3$; $L^3$ in formula (III) is an ester or amide linkage; and $R^9$ in formula (III) comprises a $C_6$-$C_{30}$ hydrocarbon group.

11. The polymer according to claim 1, further comprising a recurring unit of the formula (IV):

wherein $A^4$ in formula (IV) represents H or a chemical group containing from about 1 to about 30 carbons; $A^3$ in formula (IV) is a chemical group having a molecular weight of about 500 or less; and $A^3$ in formula (IV) bears at least one heavy atom attached to the polymer.

12. The polymer according to claim 1, further comprising a recurring unit of the formula (V):

wherein $R^{10}$ in formula (V) comprises a $C_6$ to $C_{30}$ hydrocarbon group and $R^{11}$ in formula (V) represents H or a $C_1$ to $C_{30}$ hydrocarbon group.

13. The polymer according to claim 1, further comprising a recurring unit of the formula (VI):

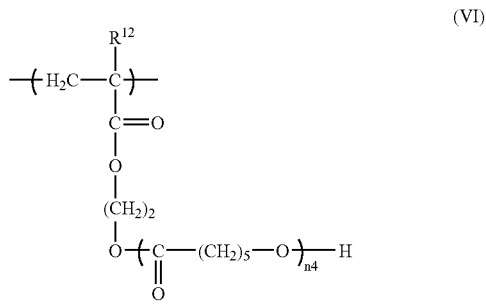

wherein $R^{12}$ in formula (VI) is H or $CH_3$ and n4 in formula (VI) is an integer in the range of about 1 to about 1,000.

14. A method for making a polymer of claim 1 comprising attaching an N-substituent during the synthesis of a corresponding monomer.

15. A method for making a polymer of claim 1 comprising attaching an N-substituent after polymerization of a corresponding monomer.

16. A medical device comprising a polymer of claim 1.

17. The medical device of claim 16, wherein the medical device comprises a stent.

18. The medical device of claim 17, wherein the stent is selected from the group consisting of a sheet stent, a braided stent, a self-expanding stent, a wire stent, a deformable stent, and a slide-and-lock stent.

19. The medical device of claim 18, wherein the self-expanding stent comprises a heat expandable portion that is temperature-dependent-expandable.

20. The medical device of claim 19, wherein the heat expandable portion is expandable at a temperature above a melting point of the polymer.

21. The medical device of claim 17 wherein at least a portion of the polymer is positioned at a surface of the stent.

22. The medical device of claim 16, wherein the polymer forms a coating on at least a portion of the medical device.

23. The medical device of claim 16 that further comprises an effective amount of at least one therapeutic agent.

24. The medical device of claim 23, wherein the therapeutic agent is selected from the group consisting of antiproliferative agent, anti-inflammatory agent, anti-matrix metalloproteinase agent, lipid lowering agent, cholesterol modifying agent, anti-thrombotic agent, and antiplatelet agent.

25. The medical device of claim 23, wherein the effective amount is sufficient to provide an effect selected from the group consisting of inhibition of restenosis, inhibition of thrombosis, inhibition of plaque formation, inhibition of plaque rupture, inhibition of inflammation, lowering of cholesterol, and promote healing.

26. An inherently radiopaque, biocompatible, bioresorbable polymer comprising one or more recurring units of the formula (Ia):

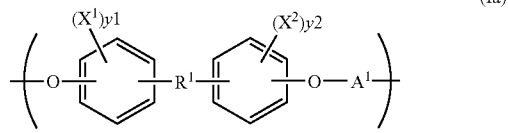

wherein:
$X^1$ and $X^2$ in formula (Ia) are each independently selected from the group consisting of Br and I;
y1 and y2 in formula (Ia) are each independently zero or an integer in the range of 1 to 4, with the proviso that the sum of y1 and y2 in formula (Ia) is at least 1;
$R^1$ in formula (Ia) is

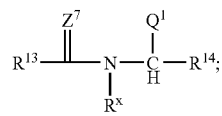

$R^x$ in formula (Ia) is selected from optionally substituted branched or unbranched $C_1$-$C_{30}$ alkyl and optionally substituted $C_6$-$C_{30}$ aryl;
$R^{13}$ and $R^{14}$ in formula (Ia) are each independently selected from the group consisting of —CH=CH—, —(CH$_2$)$_c$—, —CHJ$^2$-CHJ$^3$-, —CH=CH—(CHJ$^1$)-, and —(CH$_2$)$_c$—(CHJ$^1$)-;
c in formula (Ia) is zero or an integer in the range of 1 to 8;
$J^1$, $J^2$ and $J^3$ in formula (Ia) are each independently selected from the group consisting of H, Br, I, —NH-$Q^2$ and —C(=$Z^8$)—O$Q^3$;
$Q^1$, $Q^2$ and $Q^3$ in formula (Ia) are each independently H, a group comprising from about 1 to about 30 carbons, or a group that comprises the formula (VIIa):

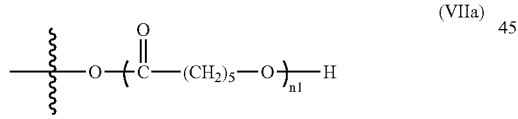

wherein n1 in formula (VIIa) is an integer in the range of about 1 to about 1,000;
$Z^7$ and $Z^8$ in formula (Ia) are each independently O or S;
$A^1$ in formula (Ia) is selected from the group consisting of

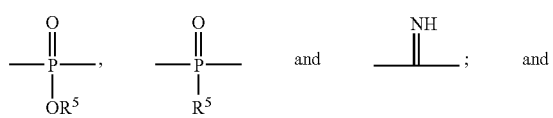

$R^5$ in formula (Ia) is selected from the group consisting of H, $C_1$-$C_{30}$ alkyl, and $C_1$-$C_{30}$ heteroalkyl.
27. The polymer according to claim 26, wherein $R^x$ in formula (Ia) is a branched or unbranched $C_1$-$C_6$ alkyl.
28. The polymer according to claim 26, wherein $R^x$ in formula (Ia) is methyl.

29. The polymer according to claim 26, wherein $Q^1$, $Q^2$ and $Q^3$ in formula (Ia) are each independently H or a non-crystallizable group comprising from about 1 to about 30 carbons.
30. The polymer according to claim 26, wherein at least one of $Q^1$, $Q^2$ and $Q^3$ in formula (Ia) is a group comprising from about 20 to about 30 carbons.
31. The polymer according to claim 26, wherein at least one of $Q^1$, $Q^2$ and $Q^3$ in formula (Ia) is a group comprising the formula (VIIa):

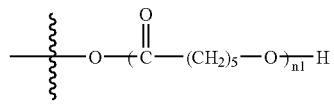

wherein n1 in formula (VIIa) is an integer in the range of about 1 to about 1,000.
32. The polymer according to claim 26, wherein:
$X^1$ and $X^2$ in formula (Ia) are each I;
$R^1$ in formula (Ia) is

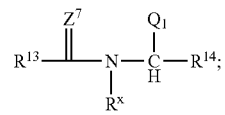

$Z^7$ in formula (Ia) is O; and
$R^{13}$ and $R^{14}$ in formula (Ia) are each independently selected from the group consisting of —CH=CH— and —(CH$_2$)$_c$—.
33. The polymer according to claim 26, further comprising one or more recurring units of the formula (IIa):

wherein:
B in formula (IIa) is —O—((CHR$^6$)$_p$—O)$_q$—;
$R^6$ in formula (IIa) is H or $C_1$ to $C_3$ alkyl;
p and q in formula (IIa) are each individually an integer in the range of about 1 to about 100;
$A^2$ in formula (IIa) is selected from the group consisting of

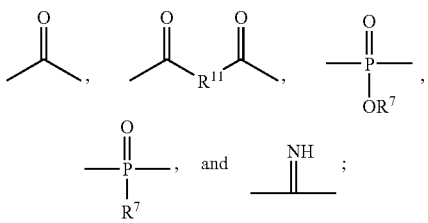

$R^7$ in formula (IIa) is H or a $C_1$-$C_{30}$ hydrocarbon; and
$R^{11}$ in formula (IIa) is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl.

34. The polymer of claim 26, further comprising one or more recurring units of the formula (Ib):

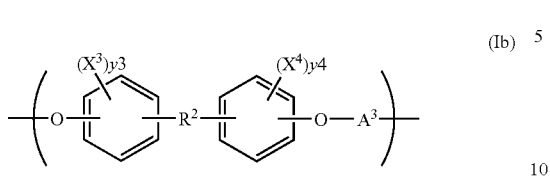

wherein:

$X^3$ and $X^4$ in formula (Ib) are each independently selected from the group consisting of Br and I;

y3 and y4 in formula (Ib) are each independently zero or an integer in the range of 1 to 4;

$R^2$ in formula (Ib) is selected from the group consisting of:

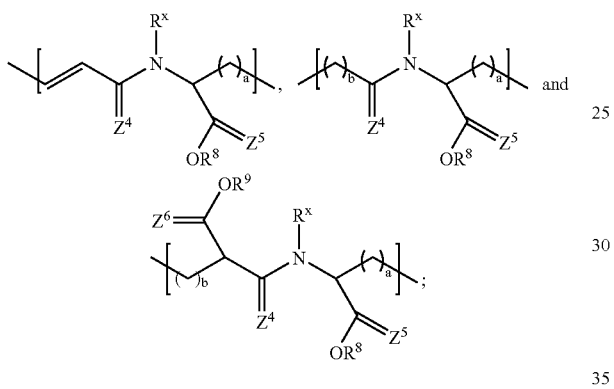

$R^x$ in formula (Ib) is selected from optionally substituted branched or unbranched $C_1$-$C_{30}$ alkyl and optionally substituted $C_6$-$C_{30}$ aryl;

$R^8$ and $R^9$ in formula (Ib) are each independently H or a non-crystallizable $C_1$ to $C_{30}$ hydrocarbon;

$Z^4$, $Z^5$ and $Z^6$ in formula (Ib) are each independently O or S;

a and b in formula (Ib) are each independently an integer in the range of 1 to 8;

$A^3$ in formula (Ib) is selected from the group consisting of

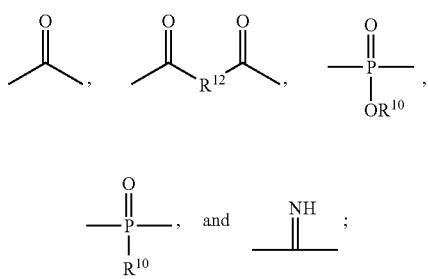

$R^{10}$ in formula (Ib) is selected from the group consisting of H, $C_1$-$C_{30}$ alkyl, and $C_1$-$C_{30}$ heteroalkyl; and $R^{12}$ in formula (Ib) is selected from the group consisting of $C_1$-$C_{30}$ alkyl, $C_1$-$C_{30}$ heteroalkyl, $C_5$-$C_{30}$ aryl, $C_6$-$C_{30}$ alkylaryl, and $C_2$-$C_{30}$ heteroaryl.

35. The polymer of claim 26, wherein $R^1$ in formula (Ia) is

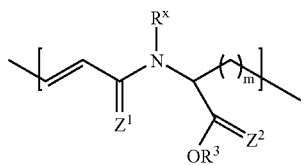

wherein $R^x$ in formula (Ia) is selected from optionally substituted branched or unbranched $C_1$-$C_{30}$ alkyl and optionally substituted $C_6$-$C_{30}$ aryl;

$R^3$ in formula (Ia) is H or a non-crystallizable $C_1$ to $C_{29}$ hydrocarbon;

$Z^1$ and $Z^2$ in formula (Ia) are each independently O or S; and m in formula (Ia) is an integer in the range of 1 to 8.

36. The polymer of claim 26, wherein $R^1$ in formula (Ia) is

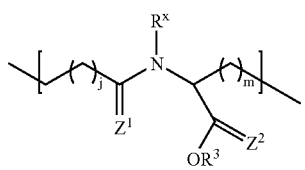

wherein $R^x$ in formula (Ia) is selected from optionally substituted branched or unbranched $C_1$-$C_{30}$ alkyl and optionally substituted $C_6$-$C_{30}$ aryl;

$R^3$ in formula (Ia) is H or a non-crystallizable $C_1$ to $C_{29}$ hydrocarbon;

$Z^1$ and $Z^2$ in formula (Ia) are each independently O or S; and j and m in formula (Ia) are each independently an integer in the range of 1 to 8.

37. The polymer of claim 26, wherein $R^1$ in formula (Ia) is

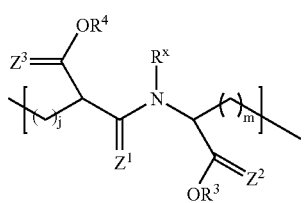

wherein $R^x$ in formula (Ia) is selected from optionally substituted branched or unbranched $C_1$-$C_{30}$ alkyl and optionally substituted $C_6$-$C_{30}$ aryl;

$R^3$ and $R^4$ in formula (Ia) are each independently H or a non-crystallizable $C_1$ to $C_{29}$ hydrocarbon;

$Z^1$, $Z^2$ and $Z^3$ in formula (Ia) are each independently O or S; and j and m in formula (Ia) are each independently an integer in the range of 1 to 8.

38. A method for making a polymer of claim 26 comprising attaching an N-substituent during the synthesis of a corresponding monomer.

39. A method for making a polymer of claim 26 comprising attaching an N-substituent during polymerization of a corresponding monomer.

40. A method for making a polymer of claim 26 comprising attaching an N-substituent after polymerization of a corresponding monomer.

41. A medical device comprising a polymer of claim 26.

42. The medical device of claim 41, wherein the medical device comprises a stent.

43. The medical device of claim 42, wherein the stent is selected from the group consisting of a sheet stent, a braided stent, a self-expanding stent, a wire stent, a deformable stent, and a slide-and-lock stent.

44. The medical device of claim 43, wherein the self-expanding stent comprises a heat expandable portion that is temperature-dependent-expandable.

45. The medical device of claim 44, wherein the heat expandable portion is expandable at a temperature above a melting point of the polymer.

46. The medical device of claim 42 wherein at least a portion of the polymer is positioned at a surface of the stent.

47. The medical device of claim 41, wherein the polymer forms a coating on at least a portion of the medical device.

48. The medical device of claim 41 that further comprises an effective amount of at least one therapeutic agent.

49. The medical device of claim 48, wherein the therapeutic agent is selected from the group consisting of antiproliferative agent, anti-inflammatory agent, anti-matrix metalloproteinase agent, lipid lowering agent, cholesterol modifying agent, anti-thrombotic agent, and antiplatelet agent.

50. The medical device of claim 48, wherein the effective amount is sufficient to provide an effect selected from the group consisting of inhibition of restenosis, inhibition of thrombosis, inhibition of plaque formation, inhibition of plaque rupture, inhibition of inflammation, lowering of cholesterol, and promote healing.

51. A polymer that comprises a recurring unit of the formula (XI):

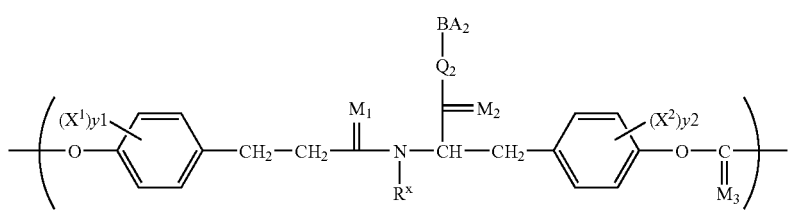

wherein $X^1$ and $X^2$ in formula (XI) are each independently selected from the group consisting of Br and I;

$y^1$ and $y^2$ in formula (XI) are each independently zero or an integer in the range of 1 to 4 (XI);

$M_1$, $M_2$, and $M_3$ in formula (XI) are each independently selected from O or S;

$Q_2$ in formula (XI) is selected from O or $NR^y$;

Rx in formula (XI) is optionally substituted branched or unbranched $C_1$-$C_{30}$ alkyl or optionally substituted $C_6$-$C_{30}$ aryl;

$R^y$ in formula (XI) is selected from hydrogen, optionally substituted branched, or unbranched $C_1$-$C_{30}$ alkyl and optionally substituted $C_6$-$C_{30}$ aryl; and $BA_2$ in formula (XI) is an optionally substituted branched or unbranched $C_1$-$C_{20}$ alkyl or aryl, or comprises a bioactive moiety selected from the group consisting of polyethylene glycol (PEG), poly(propylene glycol) (PPG), poly(tetramethylene glycol), dihydroxy polyvinylpyrrolidone (PVP), dihydroxy poly(styrene sulfonate) (HPSS), poly(2-hydroxyethyl methacrylates) (PHEMA), poly(3-hydroxypropyl methacrylates), poly (3-hydroxypropyl methacrylamide) (PHPMA), poly (alkoxy methacrylates), poly(alkoxy acrylates), polyarginine peptides (PAP), phosphoryl choline (PC), dextran, dextrin, sulfonated dextran, dermatan sulfate, heparin (HEP), chondroitan sulfate, glycosaminoglycans, chitosan, sodium hyaluronate, and hyaluronic acid (HA).

52. The polymer according to claim 51, wherein $R^x$ in formula (XI) is a branched or unbranched $C_1$-$C_6$ alkyl.

53. The polymer according to claim 51, wherein $R^x$ in formula (XI) is methyl.

54. The polymer according to claim 51, wherein $M_1$, $M_2$, and $M_3$ in formula (XI) are each independently selected from O or NH.

55. The polymer according to claim 51, further comprising one or more recurring units of the formula (XII):

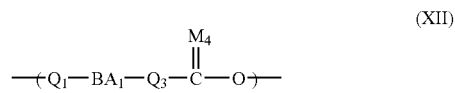

wherein $M_4$ in formula (XII) is O, NH, or S;

$Q_1$ and $Q_3$ in formula (XII) are each independently selected from O or $NR^y$;

$R^y$ in formula (XII) is selected from hydrogen, optionally substituted branched, or unbranched $C_1$-$C_{30}$ alkyl and optionally substituted $C_6$-$C_{30}$ aryl; and $BA_1$ in formula (XII) is an optionally substituted branched or unbranched $C_1$-$C_{20}$ alkyl or aryl, or comprises a bioactive moiety selected from the group consisting of polyethylene glycol (PEG), poly(propylene glycol) (PPG), poly(tetramethylene glycol), dihydroxy polyvinylpyrrolidone (PVP), dihydroxy poly(styrene sulfonate) (HPSS), poly(2-hydroxyethyl methacrylates) (PHEMA), poly(3-hydroxypropyl methacrylates), poly (3-hydroxypropyl methacrylamide) (PHPMA), poly (alkoxy methacrylates), poly(alkoxy acrylates), polyarginine peptides (PAP), phosphoryl choline (PC), dextran, dextrin, sulfonated dextran, dermatan sulfate, heparin (HEP), chondroitan sulfate, glycosaminoglycans, chitosan, sodium hyaluronate, and hyaluronic acid (HA).

56. The polymer according to claim 51, further comprising one or more recurring units of the formula (XIII):

wherein r in formula (XIII) is an integer in the range of from about 1 to about 12.

57. The polymer according to claim 51, further comprising one or more recurring units of the formula (XIV):

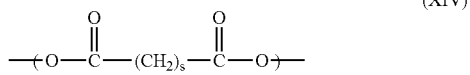 (XIV)

wherein s in formula (XIV) is an integer in the range of from about 2 to about 30.

58. A method for making a polymer of claim 51 comprising attaching an N-substituent during the synthesis of a corresponding monomer.

59. A method for making a polymer of claim 51 comprising attaching an N-substituent during polymerization of a corresponding monomer.

60. A method for making a polymer of claim 51 comprising attaching an N-substituent after polymerization of a corresponding monomer.

61. A medical device comprising a polymer of claim 51.

62. The medical device of claim 61, wherein the medical device comprises a stent.

63. The medical device of claim 62, wherein the stent is selected from the group consisting of a sheet stent, a braided stent, a self-expanding stent, a wire stent, a deformable stent, and a slide-and-lock stent.

64. The medical device of claim 63, wherein the self-expanding stent comprises a heat expandable portion that is temperature-dependent-expandable.

65. The medical device of claim 64, wherein the heat expandable portion is expandable at a temperature above a melting point of the polymer.

66. The medical device of claim 62 wherein at least a portion of the polymer is positioned at a surface of the stent.

67. The medical device of claim 61, wherein the polymer forms a coating on at least a portion of the medical device.

68. The medical device of claim 61 that further comprises an effective amount of at least one therapeutic agent.

69. The medical device of claim 68, wherein the therapeutic agent is selected from the group consisting of antiproliferative agent, anti-inflammatory agent, anti-matrix metalloproteinase agent, lipid lowering agent, cholesterol modifying agent, anti-thrombotic agent, and antiplatelet agent.

70. The medical device of claim 68, wherein the effective amount is sufficient to provide an effect selected from the group consisting of inhibition of restenosis, inhibition of thrombosis, inhibition of plaque formation, inhibition of plaque rupture, inhibition of inflammation, lowering of cholesterol, and promote healing.

* * * * *

UNITED STATES PATENT AND TRADEMARK OFFICE
CERTIFICATE OF CORRECTION

PATENT NO. : 8,034,365 B2
APPLICATION NO. : 11/873362
DATED : October 11, 2011
INVENTOR(S) : Ernest G. Baluca Page 1 of 2

It is certified that error appears in the above-identified patent and that said Letters Patent is hereby corrected as shown below:

| Column | Line | |
|---|---|---|
| 5 | 35 | Change "substitutent" to --substituent--. |
| 6 | 7 | Change "unstubstituted." to --unsubstituted.--. |
| 6 | 15 | Change "substitutent" to --substituent--. |
| 12 | 56 | Change "—CONH—$C_{n1+1}$," to -- —CONH—$C_{n1}H_{2n+1}$,--. |
| 12 | 57 | Change "—$CO_2H_{2n1}$—$(CH_2)_{n1}$—Br," to -- —$CO_2$—$(CH_2)_{n1}$—Br,--. |
| 12 | 61 | Change "=$(CH_2)_a$—;" to -- —$(CH_2)_a$—;--. |
| 16 | 13 | Change "Polm." to --Poly.--. |
| 19 | 3 | Change "(I)," to --(II),--. |
| 19 | 43 | Change "trom" to --from--. |
| | (Approx.) | |
| 25 | 1-6 | Change |
| | (Approx.) | |

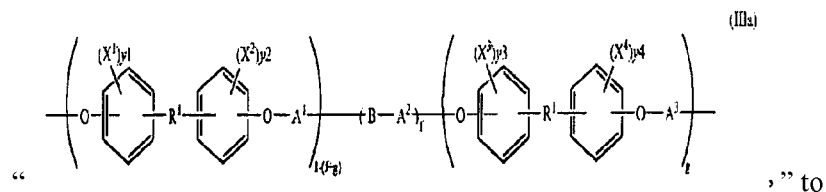

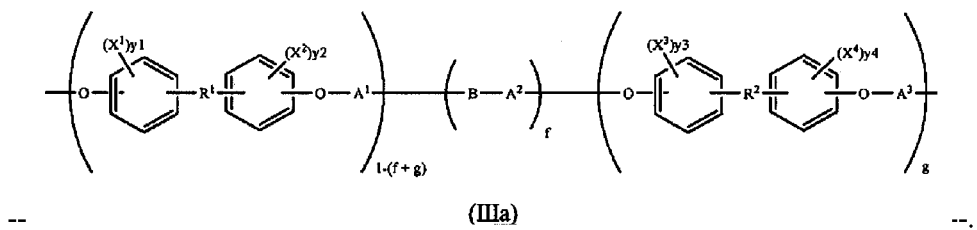

Signed and Sealed this
First Day of May, 2012

David J. Kappos
*Director of the United States Patent and Trademark Office*

CERTIFICATE OF CORRECTION (continued)
U.S. Pat. No. 8,034,365 B2

| | | |
|---|---|---|
| 30 | 48 (Approx.) | Change "of" to --d--. |
| 30 | 53 (Approx.) | Change "sidechain," to --side chain,--. |
| 38 | 42 | Change "poly(imono" to --poly(imino--. |
| 39 | 40 | Change "(polyethylene" to --polyethylene--. |
| 39 | 41 | Change "polypropylene" to --poly(propylene--. |
| 41 | 53 | Change "dicylohexylcarbodiimide" to --dicyclohexylcarbodiimide--. |
| 41 | 64-65 | Change "mPEG amide" to --mPEG--. |
| 42 | 67 | Change "50%" to --50%.--. |
| 51 | 32 (Approx.) | Change "Schlenck" to --Schlenk--. |
| 51 | 34 (Approx.) | Change "Schlenck" to --Schlenk--. |
| 60 | 22 | Change "the its" to --its--. |
| 62 | 37-38 | Change "dioxorubicin," to --doxorubicin--. |
| 62 | 41 | Change "Rofexcoxib," to --Rofecoxib,--. |
| 66 | 32 | Change "thereof," to --thereof;--. |
| 71 | 29 | Change "thereof" to --thereof,--. |
| 76 | 21 | Change "integrelin," to --integrilin,--. |
| 77 | 2 | Change "cytoxins," to --cytotoxins,--. |
| 77 | 41 | Change "processed)," to --(processed),--. |
| 80 | 38 (Approx.) | In Claim 2, change "wherein" to --wherein $R^x$--. |
| 81 | 13 (Approx.) | In Claim 7, change "to" to --according to--. |
| 81 | 18 (Approx.) | In Claim 8, change "to" to --according to--. |
| 81 | 37 (Approx.) | In Claim 10, change "polymer of" to --polymer--. |
| 83 | 33 (Approx.) | In Claim 26, change "—$(CH_2)_c$—," to -- —$(CH_2)_c$—, —$(CHJ^1)$—,--. |
| 84 | 9 | In Claim 31, change "Q'," to --$Q^1$,--. |